United States Patent
Buell et al.

(10) Patent No.: US 10,575,999 B2
(45) Date of Patent: Mar. 3, 2020

(54) PACKAGE ASSEMBLY FOR OR WITH A TAMPON APPLICATOR

(71) Applicant: Edgewell Personal Care Brands, LLC, Chesterfield, MO (US)

(72) Inventors: Sezen Buell, Waldwick, NJ (US); Richard Timmers, Saddie Brook, NJ (US); Pankaj Nigam, Ridgewood, NJ (US); Ricardo de Oliveira, New Hope, PA (US); Scott Osiecki, Skaneateles, NY (US); Philip Burkhardt, Magnolia, DE (US); Adeyinka Abdul, Newark, DE (US); Kyle Hillegass, Milltown, NJ (US); Peter Preisner, Quinton, VA (US); Hassan Mohamed, Bayonne, NJ (US); Joseph Fedora, South Acworth, NH (US)

(73) Assignee: EDGEWELL PERSONAL CARE BRANDS, LLC., Chesterfiled, MO (US)

( * ) Notice: Subject to any disclaimer, the term of this patent is extended or adjusted under 35 U.S.C. 154(b) by 319 days.

(21) Appl. No.: 15/191,647

(22) Filed: Jun. 24, 2016

(65) Prior Publication Data
US 2017/0128286 A1 May 11, 2017

Related U.S. Application Data

(60) Continuation-in-part of application No. 14/943,207, filed on Nov. 17, 2015, now abandoned, which is a
(Continued)

(51) Int. Cl.
*A61F 13/26* (2006.01)
*A61F 13/34* (2006.01)
(Continued)

(52) U.S. Cl.
CPC ...... *A61F 13/55185* (2013.01); *A61F 13/263* (2013.01); *A61F 13/266* (2013.01);
(Continued)

(58) Field of Classification Search
CPC .................. A61F 13/263; A61F 13/266; A61F 13/55175; A61F 13/5518; A61F 13/55185; A61F 13/26–13/28; A61F 13/34

See application file for complete search history.

(56) References Cited

U.S. PATENT DOCUMENTS

| 2,501,972 A | 7/1946 | Seider |
| 2,770,358 A | 10/1951 | Keith |

(Continued)

FOREIGN PATENT DOCUMENTS

| AU | 2005100489 | 7/2005 |
| DE | 10015678 | 10/2001 |

(Continued)

OTHER PUBLICATIONS

The Non-Final Office Action of U.S. Appl. No. 13/926,875, dated Apr. 15, 2015.
(Continued)

*Primary Examiner* — Susan S Su

(57) ABSTRACT

Disclosed is a tampon applicator package assembly having a tampon applicator and a cap having a closed end and an open end. The tampon applicator has a barrel for housing a pledget and a plunger. The plunger has an end portion that is a cap cover that connects to a remainder of the plunger and mates with the cap at the open end to provide a seal with the cap that completely encloses the tampon applicator in the cap. Also disclosed is an assembly having a tampon applicator, a cap having both a closed end and open end, and a cap cover for covering the open end of the cap. When the cap
(Continued)

cover is placed on the open end, the open end is sealed and the tampon applicator is completely enclosed in the cap.

16 Claims, 42 Drawing Sheets

Related U.S. Application Data division of application No. 13/926,875, filed on Jun. 25, 2013, now Pat. No. 9,427,361.

(60) Provisional application No. 61/663,946, filed on Jun. 25, 2012.

(51) Int. Cl.
  *A61F 13/551* (2006.01)
  *B65D 39/00* (2006.01)
  *B65D 43/14* (2006.01)

(52) U.S. Cl.
  CPC .......... *A61F 13/34* (2013.01); *A61F 13/5518* (2013.01); *A61F 13/55175* (2013.01); *B65D 39/0005* (2013.01); *B65D 43/14* (2013.01)

(56) References Cited

U.S. PATENT DOCUMENTS

| | | | |
|---|---|---|---|
| 4,881,644 A | 11/1989 | Norquest et al. |
| 4,973,302 A | 11/1990 | Armour et al. |
| 5,041,080 A | 8/1991 | Shimatani et al. |
| 5,988,386 A | 11/1999 | Morrow |
| 6,129,471 A | 10/2000 | Lang |
| 6,217,542 B1 | 4/2001 | Stevens et al. |
| 6,393,614 B1 | 5/2002 | Eichelbaum |
| 6,687,911 B2 | 2/2004 | Fitz |
| 7,722,099 B2 | 5/2010 | Bland |
| D618,905 S | 7/2010 | Watson |
| 7,854,317 B1 | 12/2010 | Hebert et al. |
| 2003/0036721 A1 | 2/2003 | Zhao |
| 2003/0080119 A1 | 5/2003 | Chisholm et al. |
| 2005/0098466 A1 | 5/2005 | Thomas |
| 2005/0109663 A1 | 5/2005 | Krey |
| 2005/0109786 A1 | 5/2005 | Krey |
| 2005/0228355 A1 | 10/2005 | Briggs |
| 2006/0212015 A1 | 9/2006 | Peele |
| 2006/0247571 A1 | 11/2006 | Hayes et al. |
| 2006/0283751 A1 | 12/2006 | Rhea |
| 2007/0179466 A1 | 8/2007 | Tremblay et al. |
| 2007/0191805 A1 | 8/2007 | Kramer |
| 2008/0167598 A1 | 7/2008 | Gann et al. |
| 2008/0167599 A1* | 7/2008 | Osborn ................ A61F 13/266 604/14 |
| 2009/0112148 A1 | 4/2009 | Morrow |
| 2009/0247930 A1* | 10/2009 | Fung ...................... A61F 13/26 604/16 |
| 2009/0247981 A1 | 10/2009 | Glaug et al. |
| 2009/0294315 A1 | 12/2009 | Silcott |
| 2010/0078348 A1 | 4/2010 | Kondo et al. |
| 2010/0094238 A1 | 4/2010 | Scarano |
| 2010/0122709 A1 | 5/2010 | Janatpour et al. |
| 2010/0252559 A1 | 10/2010 | Watson |
| 2011/0105830 A1* | 5/2011 | Hou ....................... A61F 2/005 600/30 |
| 2012/0097576 A1 | 4/2012 | Dold |
| 2013/0165843 A1* | 6/2013 | Hou ....................... A61F 2/005 604/11 |
| 2013/0319890 A1 | 12/2013 | Davis et al. |
| 2014/0238588 A1 | 8/2014 | Karsenti |
| 2014/0276522 A1 | 9/2014 | Thompson |
| 2017/0231286 A1* | 8/2017 | Borkovec ............. A24F 47/008 131/329 |

FOREIGN PATENT DOCUMENTS

| | | |
|---|---|---|
| DE | 10105428 | 8/2002 |
| DE | 202005007449 | 8/2005 |
| DE | 102010050479 | 5/2012 |
| GB | 2424641 | 10/2006 |
| GB | 2449126 | 11/2008 |
| JP | 2005259773 | 9/2005 |
| JP | 2014128429 | 7/2014 |
| WO | 0064778 | 11/2000 |
| WO | 2004000664 | 12/2003 |
| WO | 2008068739 | 6/2008 |

OTHER PUBLICATIONS

Examiners Report of Australian Application No. 2013280462, dated Oct. 18, 2016.

* cited by examiner

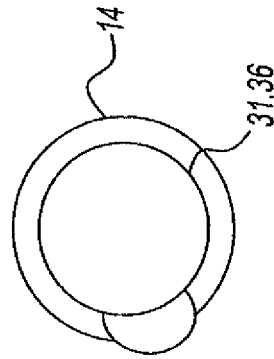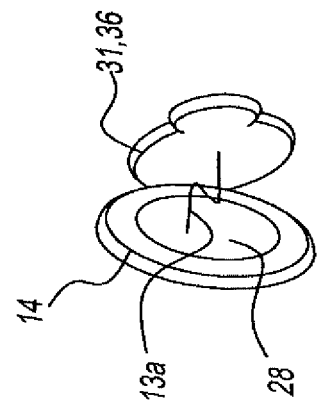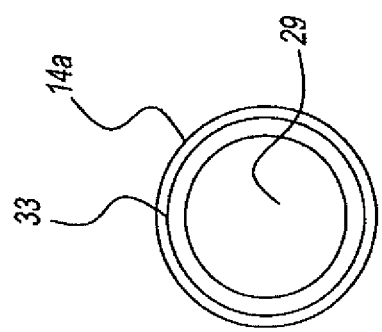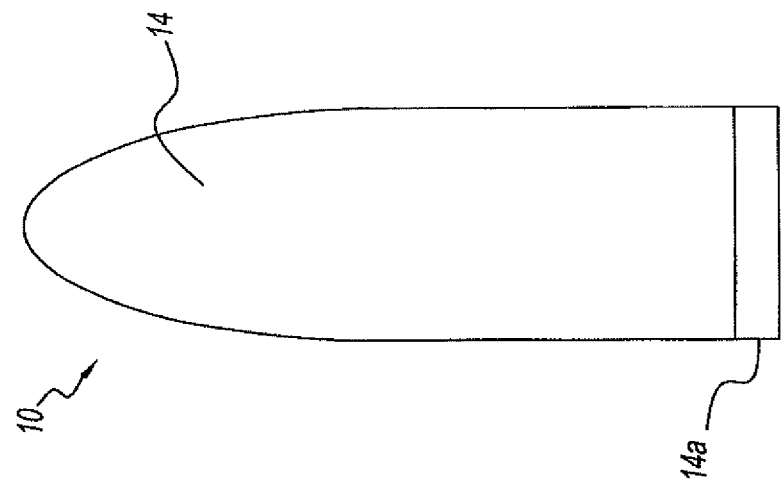

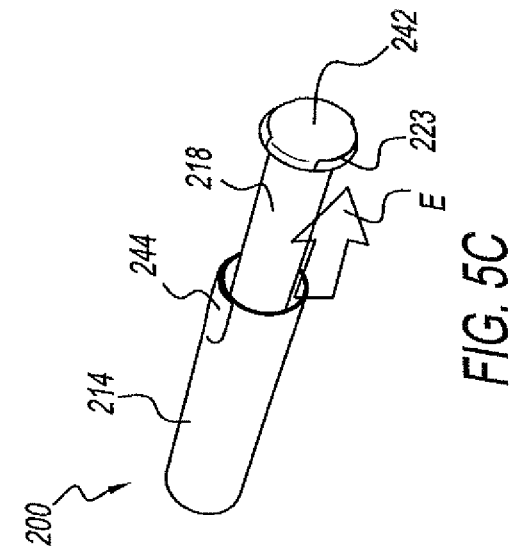
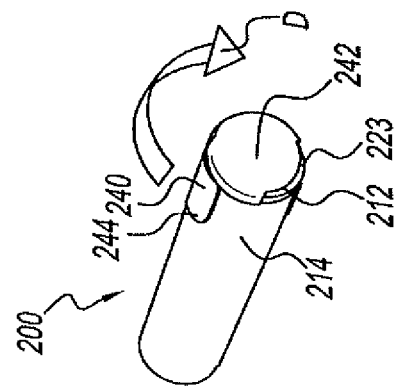
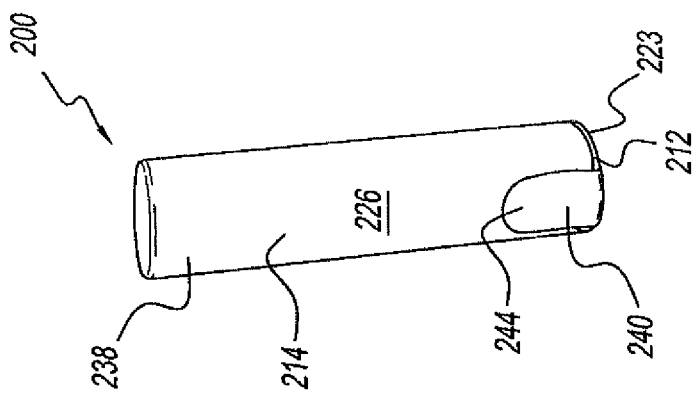
FIG. 5C
FIG. 5B
FIG. 5A

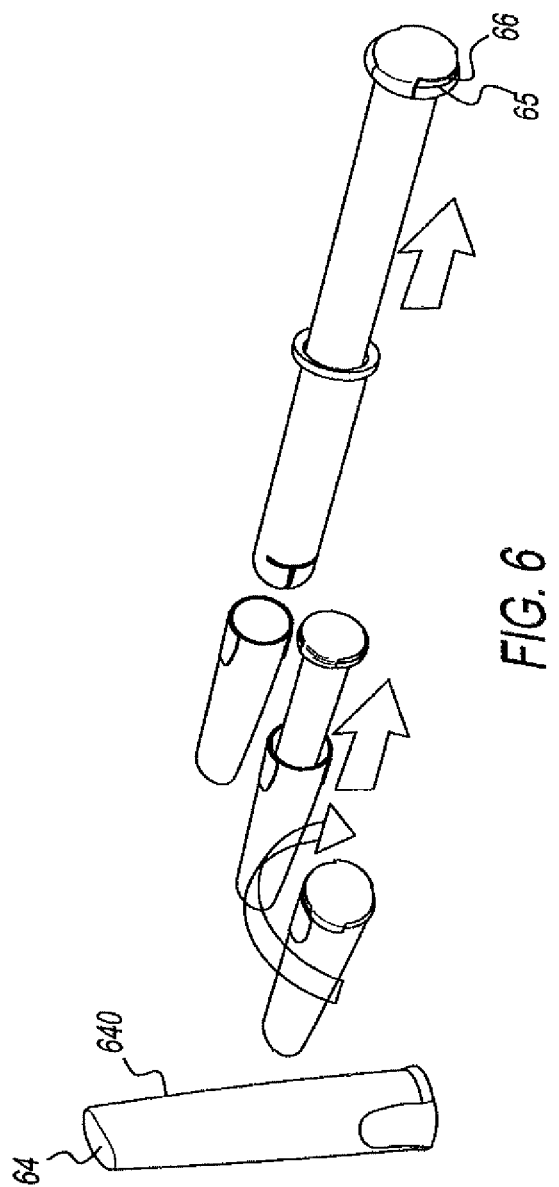

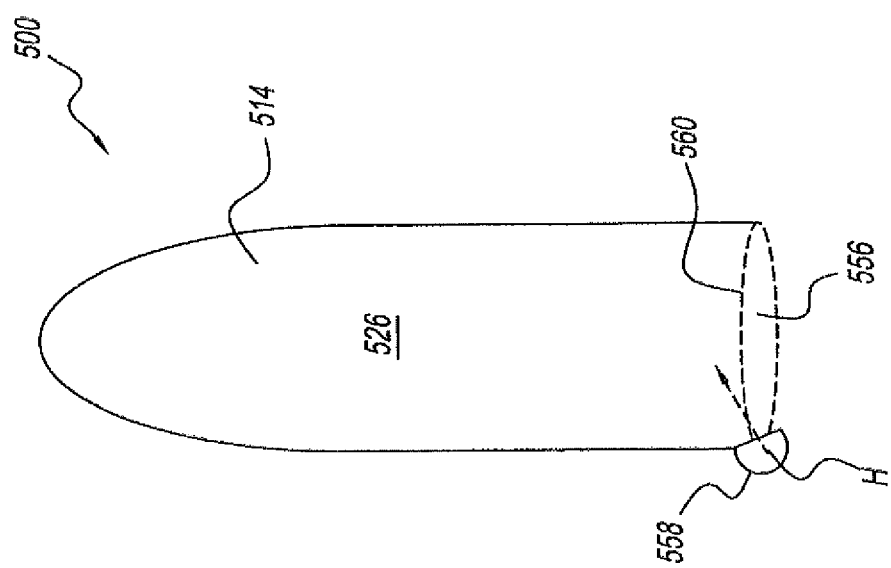
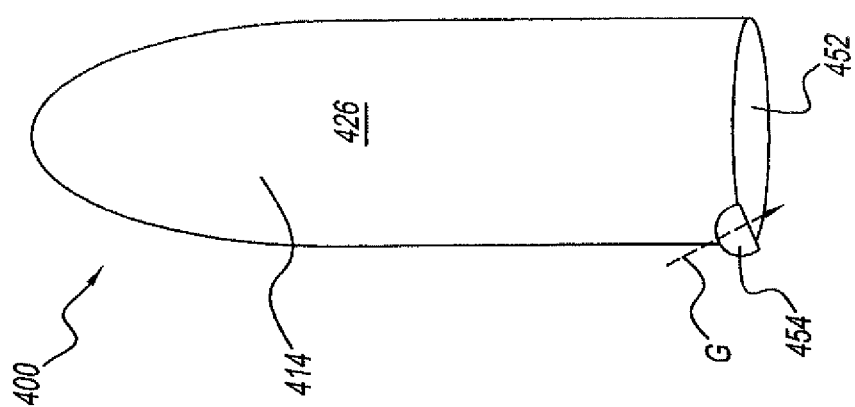
FIG. 14A
FIG. 14B

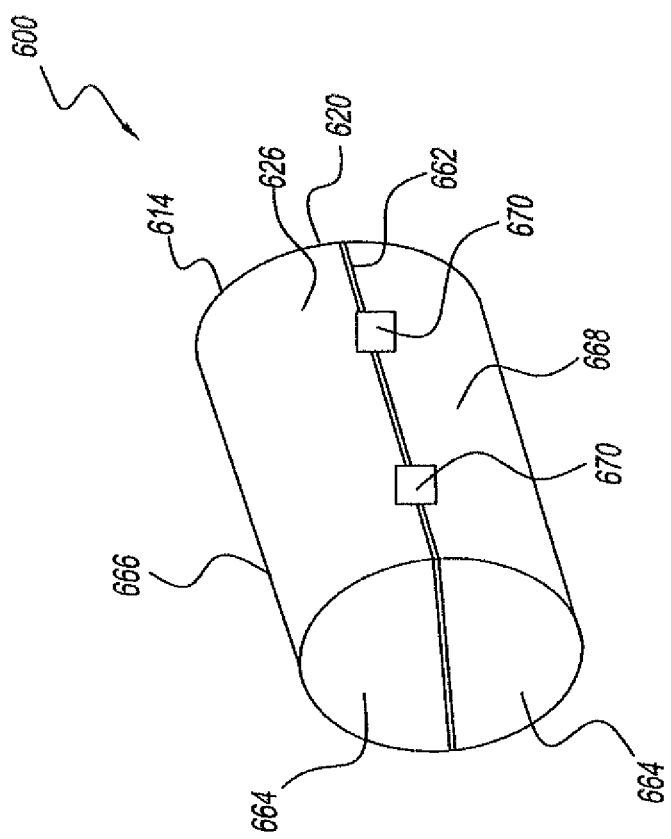
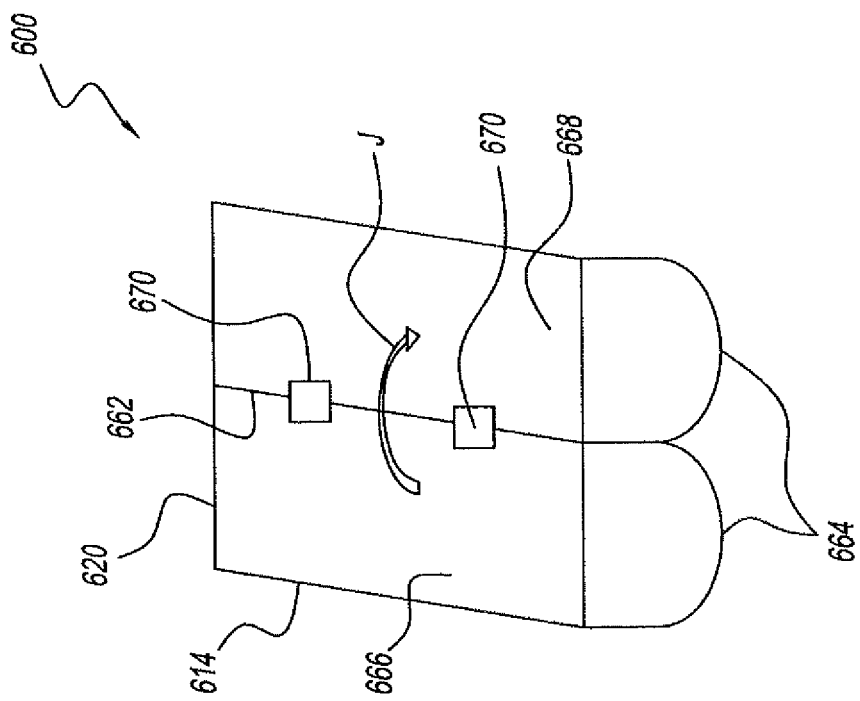
FIG. 15B
FIG. 15A

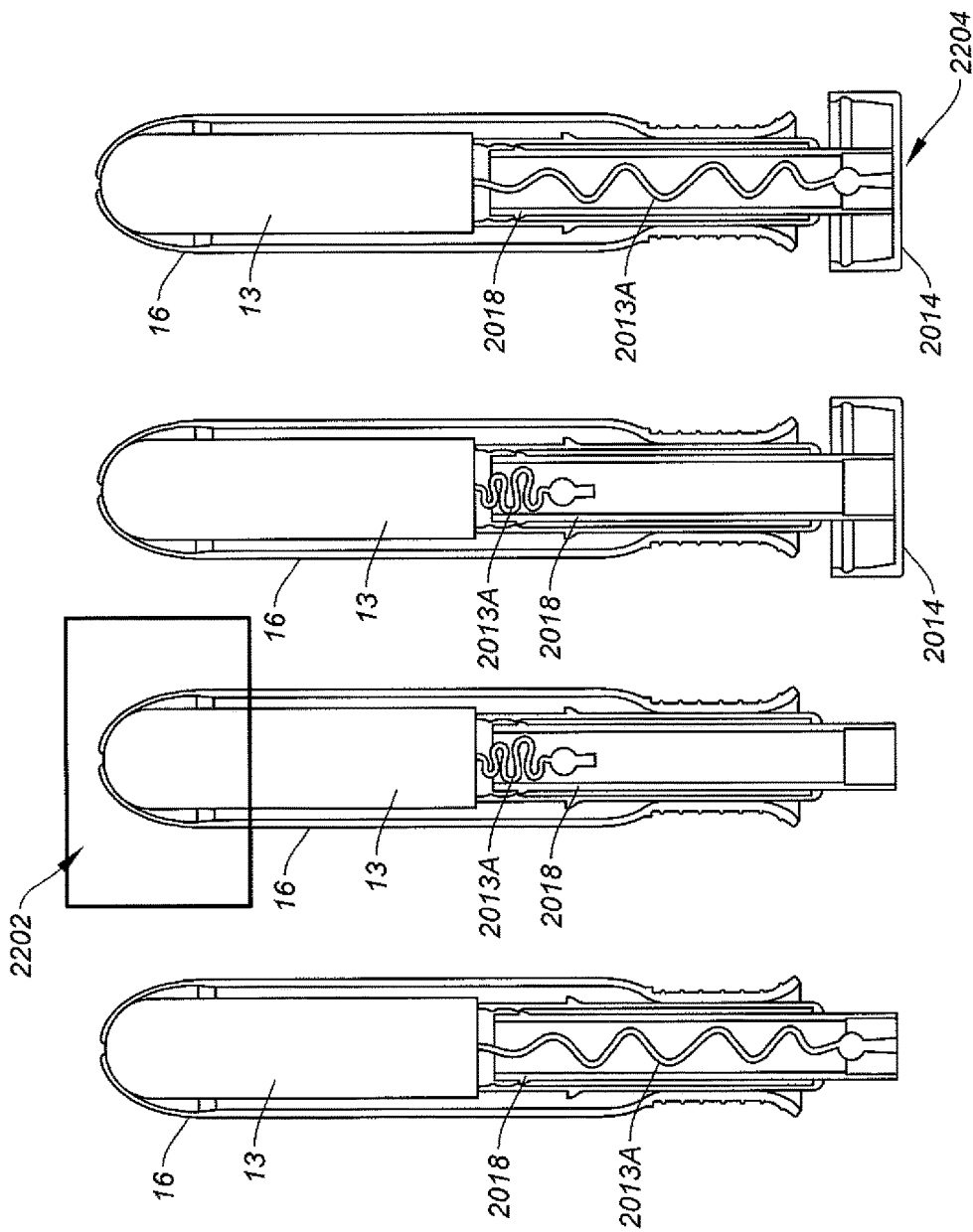

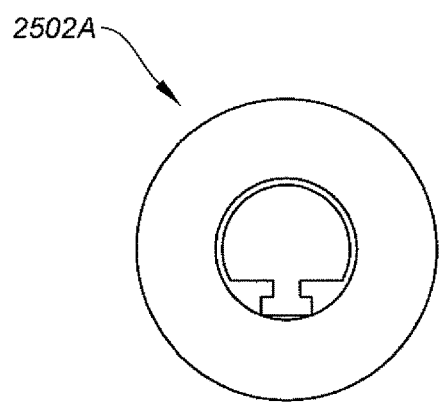
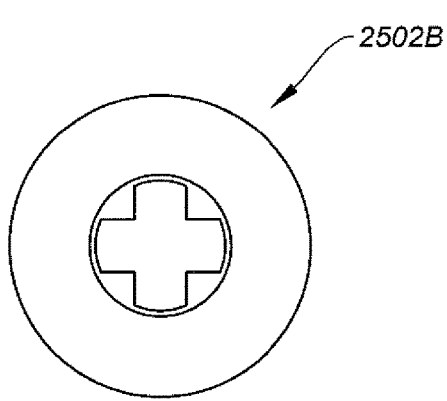
FIG. 26A    FIG. 26B
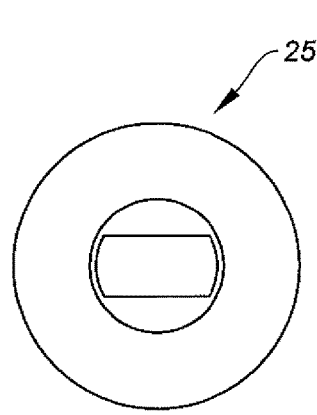
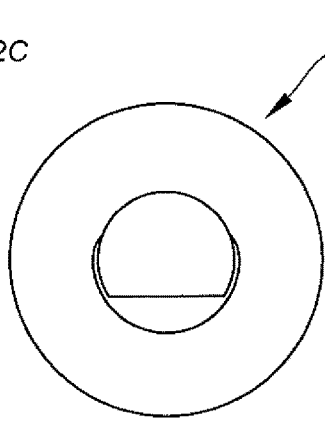
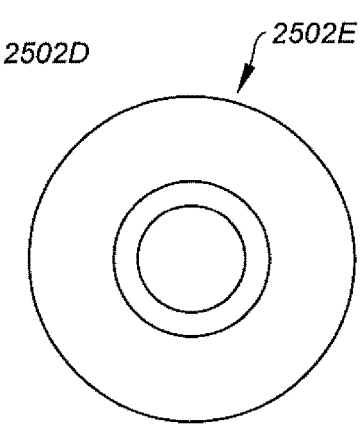
FIG. 26C    FIG. 26D    FIG. 26E
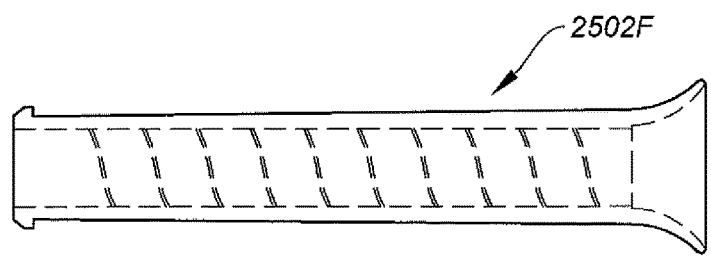
FIG. 26F

PACKAGE ASSEMBLY FOR OR WITH A TAMPON APPLICATOR

CROSS-REFERENCE TO RELATED APPLICATIONS

This application is related to, and is a continuation-in-part of U.S. patent application Ser. No. 14/943,207, filed Nov. 17, 2015, which is a continuation of U.S. patent application Ser. No. 13/926,875, filed Jun. 25, 2013, which claims the benefit of U.S. Provisional Patent Application No. 61/663,946, filed on Jun. 25, 2012, the disclosures of which are incorporated in their entirety by reference herein.

BACKGROUND OF THE DISCLOSURE

1. Field of the Disclosure

The present disclosure relates to a package assembly for or with a tampon applicator or other feminine hygiene device. More particularly, the present disclosure relates to a cap for a tampon applicator and, in particular, a cap for a tampon applicator that eliminates the need for separate packaging and also, preferably, functions to disguise the tampon from recognition as a tampon, both before and after use, and is durable.

2. Description of Related Art

Feminine hygiene devices, and other devices for insertion into the body, such as, for example, tampons, pessaries, suppositories and other vaginal insertion devices are used, for example, by women within the vagina for feminine needs, such as, for example, to absorb menstrual flow. Many women almost always carry a feminine hygiene product with them, i.e., in their purse, in their pockets or in other quickly accessible locations, since the beginning of menstrual flow can be unexpected.

Current tampons are typically individually packaged in wrappers that are usually made of plastic film, such as polypropylene and polyethylene, or paper. It is important for this package to stay intact as tampons can get soiled by dust, upon coming in contact with other objects, unintended touching and the like.

Using dirty and damaged tampons can result in injury, infection or illness. Currently available wrappers tend to tear, break open and/or puncture when they travel in the purse or pocket for an extended amount of time. The exposed, and possibly damaged, tampons may cause infection and can result in pain and discomfort during insertion. It is also very inconvenient to the user as she may not be able to use the product and have to find an alternative.

Another drawback of the current wrappers is that the shapes are very traditional and colors of the wrappers are either very feminine or very vibrant, making it very easy to identify tampons from a distance. This can be embarrassing for some women, especially a teenager who is just starting to have menstrual cycles.

Yet another drawback of the current tampon and wrapper assemblies is the number of steps needed to remove the tampon from the wrapper and thereafter insert the tampon, and dispose of one or more or all of the used tampon, applicator, wrapper, and other hygiene product. For instance, current tampon and wrapper assemblies require (1) tearing or opening the wrapper, typically involving two hands (i.e. one hand to grip a first portion of the wrapper and the other hand to move another portion of the wrapper in an opposite direction from the first edge, thereby causing the wrapper to tear, break or open), (2) removing the tampon from the wrapper, also typically requiring two hands (i.e. one hand to hold the opened wrapper and the other hand to remove the tampon from the wrapper), (3) positioning the tampon applicator for use, which may also typically require two hands (i.e. reorienting the tampon in one's hand for proper insertion orientation, withdrawing the plunger (with one hand) from the applicator (by holding the applicator in the other hand) such that the tampon applicator is positioned and ready to apply a force to the pledget in the applicator for insertion into the body, putting the plunger, with one hand, into the applicator (being held by the other hand) such that the plunger can be used to apply a force to the pledget in the applicator for insertion into the body), (4) inserting the tampon into the body, (5) removing the applicator from the body (for systems employing an applicator), (6) re-opening the wrapper for placement of the used tampon and/or applicator, which also requires two hands: one hand to hold the used tampon and the other to hold the wrapper open, (7) placing the used tampon and/or applicator into the opened wrapper, which also requires to hands: one hand to hold the used tampon and the other to hold the wrapper open, and (8) disposing of the wrapper containing the used tampon and/or applicator. Accordingly, current wrapper and tampon assemblies typically require five (5) to six (6) steps to open, prepare, insert the tampon, and remove the used tampon and/or applicator, and seven (7) to eight (8) steps if including the steps of disposing of the used tampon. Further, many of these steps require the use of two hands.

Yet another drawback of the current tampon and wrapper assemblies is the difficulty of disposal. Since the wrapper does not tear consistently, it makes it very difficult to place the used applicator back into the torn wrapper. In most instances, the user needs to find alternative ways for disposal such as wrapping the used applicator with toilet paper and/or disposing the applicator and wrapper separately.

Yet another drawback of the current wrappers is that they are bulky, especially for full-sized applicators, and thus occupy a rather large amount of space. The larger size also makes the wrapper difficult and indiscrete to carry about or carry to the bathroom as the wrapper does not fit in the palm of the user's hand.

Therefore, it has been determined that there is a need for a tampon applicator and package assembly that will provide small, durable packaging and provide discrete user experience.

SUMMARY OF THE DISCLOSURE

The present disclosure provides a tampon applicator package assembly that includes a cap and a tampon applicator having a barrel and a plunger. The tampon applicator has a barrel with an insertion tip and a plunger receiving end opposite the insertion tip. The plunger has a first end in the barrel and a second end, opposite the first end, at least partially outside of the barrel. The cap has a cap wall that encloses the barrel and connects to the second end of the plunger or the plunger receiving end of the barrel.

In one embodiment, the present disclosure provides a tampon applicator package assembly comprising a cap and a tampon applicator having a barrel and a plunger, with the tampon applicator disposed in the cap. The plunger has an end portion that mates with the cap to provide an at least partial seal that completely encloses the barrel and the plunger in the cap.

In another embodiment, the present disclosure provides a tampon applicator package assembly comprising a tampon applicator having a barrel and a plunger with a grippable area, a cap having a closed end and an open end, and a cap cover for sealing the open end of the cap. The tampon applicator is disposed in the cap. The cap cover has an inner end and an outer end. The inner end is disposed proximal the tampon applicator. When the cap cover is placed on the open end of the cap, an at least partial seal is provided with the cap that completely encloses the barrel and the plunger. When the cap cover is removed from the open end of the cap, the grippable area of the plunger is exposed.

In still another embodiment, the present disclosure provides a tampon applicator package assembly comprising a tampon applicator having a barrel and a plunger with a grippable area, a cap having a closed end and an open end, and a cap cover for placing over and sealing the open end of the cap. The tampon applicator is disposed in the cap. The cap cover has an inner end and an outer end. The inner end is disposed proximal the tampon applicator. When the cap cover is placed on the open end of the cap, an at least partial seal is provided with the cap that completely encloses the tampon applicator and the cap cover matingly engages at or near the grippable area of the plunger. When the cap cover is removed from the open end of the cap, the grippable area is withdrawn at least partially from the cap.

In yet another embodiment, the tampon package assembly further comprises a string attached to the pledget in the tampon applicator that is enclosed in the tampon applicator package. When the cap cover is removed from the open end of the cap, the string is exposed.

In a further embodiment, the tampon package assembly comprises a string attached to the pledget and the string is folded and enclosed in the tampon applicator package when the cap cover is placed on the cap. When the cap cover is removed from the cap, the string is at least partially unfolded. The string maybe at least partially unfold by attachment to the cap cover by, e.g., mechanical attachment such as through the use of adhesive, or by other physical attachment to the cap cover.

In a still further embodiment, the tampon package assembly has the string attached to the pledget and affixed to the plunger, and the string is immediately exposed when the cap cover is removed.

In an additional embodiment, the cap and/or cap cover is made of a foil or paper (or other flexible material) cap cover and is peelable away from the cap to expose the plunger or grippable area of the plunger. The foil or paper (or other flexible material) may be peelable away from the open end of the cap due to attachment by an adhesive or through the use of perforations. In a further additional embodiment, the cap can be a flexible material and the cap cover can be a more rigid material. The cap cover can at least partially connect to either the cap, the grippable area of the plunger, or both.

In a further embodiment, the cap has two covers, one disposed at or near the pledget-containing end of the barrel and one disposed at or near the grippable area of the plunger.

In a still further embodiment, the tampon applicator package assembly has two caps. In a yet further embodiment, the two caps can be at least partially attached by a connector and/or ring.

In another embodiment, a tampon applicator package assembly enables the user to open, prepare, insert, and remove the tampon applicator in four steps. In a further embodiment, a tampon applicator package assembly enables the user to dispose of the tampon applicator package assembly in one further step.

In a still further embodiment, a tampon applicator package assembly is discrete in that the tampon applicator package assembly obfuscates the appearance of a feminine hygiene device.

In a yet further embodiment, a tampon applicator package assembly that has increased durability is provided, so that the tampon applicator package assembly cannot be torn or punctured during a storage position at any time including while being transported.

The above-described and other features and advantages of the present disclosure will be appreciated and understood by those skilled in the art from the following detailed description, drawings, and appended claims.

BRIEF DESCRIPTION OF THE DRAWINGS

FIG. 3A is a side view of another embodiment of a tampon applicator package assembly of the present disclosure having a bottom cap.

FIG. 3B is a bottom view of the cap cover of FIG. 3A.

FIG. 3C is a bottom view of the cap cover of FIG. 3A connected to a seal or a sticky tab.

FIG. 3D is a perspective view of the cap cover of FIG. 3C partially disconnected from the seal or the sticky tab with a pledget string attached to the sticky tab.

FIG. 5A is a side view of another embodiment of a tampon applicator package assembly of the present disclosure with a tampon applicator having a plunger in a stored position and a cap connected to the tampon applicator.

FIG. 5B is a rear perspective view of the tampon applicator package assembly of FIG. 5A.

FIG. 5C is a rear perspective view of the tampon applicator package assembly of FIG. 5A with the tampon applicator having the plunger partially in a use position.

FIGS. 6, 7, 8, 9 and 10 are exploded, perspective views of alternative embodiments of the tampon applicator package assembly of FIGS. 5A-5D.

FIG. 14A is a side perspective view of a cap of another embodiment of a tampon applicator package assembly of the present disclosure.

FIG. 14B is a side perspective view of a cap of another embodiment of a tampon applicator package assembly of the present disclosure.

FIG. 15A is a schematic side perspective view of a cap of another embodiment of a tampon applicator package assembly of the present disclosure having the cap in an open position.

FIG. 15B is a schematic perspective view of the cap of FIG. 15A in a closed position.

FIG. 22A-E illustrate a tampon applicator package assemblies including a cap and a barrel configured to manage a string.

FIGS. 26A-F illustrate various designs and geometries for an obstruction.

DETAILED DESCRIPTION OF THE DISCLOSURE

Figure 1A:
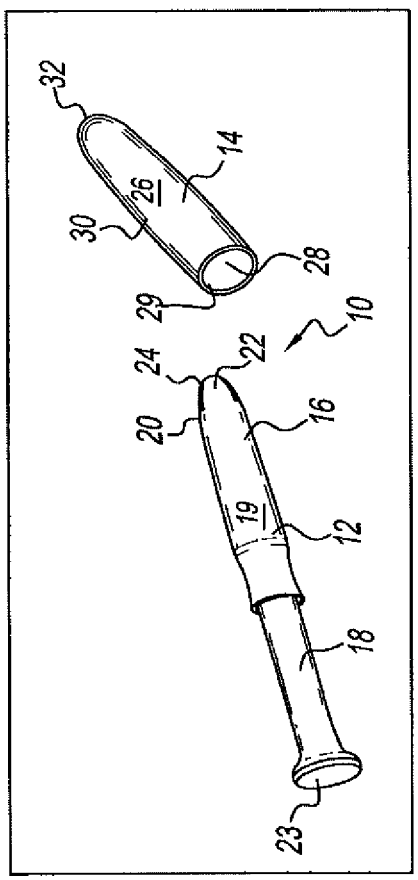
FIG. 1A is an exploded top view of an exemplary embodiment of a tampon applicator package assembly of the present disclosure with a tampon applicator having a plunger in a use position and a cap disconnected from the tampon applicator.

Referring to the drawings and in particular to FIGS. 1A-1D, an exemplary embodiment of a tampon applicator package assembly according to the present disclosure is shown and generally referred to by reference numeral 10. The terms "tampon applicator package assembly" and "tampon package applicator assembly" are synonymous and interchangeable for purposes of the present disclosure, and are both generally referred to by reference numeral 10. Tampon applicator package assembly 10 has a tampon applicator 12 and a cap 14. Tampon applicator 12 is shown in a use position in FIG. 1A. Tampon applicator 12 has a barrel 16 for housing a pledget 13 (shown in FIG. 2) and a plunger 18 in a telescoping configuration. Pledget 13 is an absorbent material. Barrel 16 has a barrel wall 19 with an insertion tip 20. Insertion tip 20 has a plurality of petals 22 separated by cuts 24 through barrel wall 19. Plunger 18 has a telescoping portion 21 and an end portion 23. End portion 23 may be a cap cover that connects to a remainder of plunger 18. As with tampon applicators, barrel 16 can be inserted into a body of a user to eject the pledget into the body, such as, for example, to absorb menstrual flow. When barrel 16 is inserted into the user's body, the user applies a force to end portion 23 of plunger 18 to move telescoping portion 21 of plunger 18 in a direction shown by arrow A further into barrel 16 that moves the pledget through the opening and, thus, through insertion tip 20 into the body.

Figure 1B:
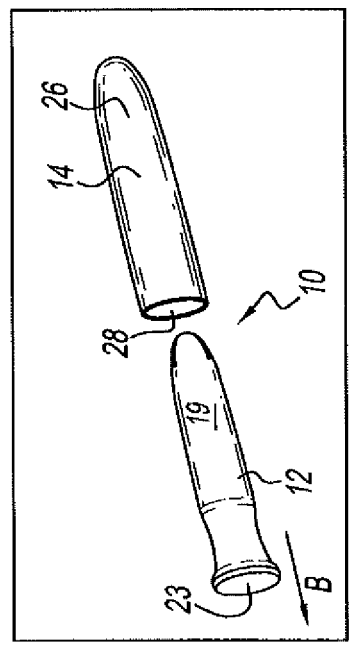
FIG. 1B is an exploded perspective view of the tampon applicator package assembly of FIG. 1A.

Referring to FIG. 1B, cap 14 has a cap body 26 with a cap opening 29 and a cavity 28 in cap body 26. Cap 14 is sized and shaped to cover barrel 16. For example, cap body 26 has a cylindrical wall 30 and a top portion 32 that has a similar or mating shape to insertion tip 20.

Figure 1C:
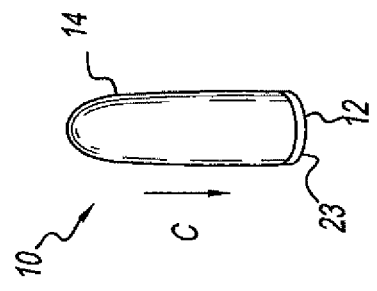
FIG. 1C is an exploded perspective view of the tampon applicator package assembly of FIG. 1A having the plunger in the stored position and the cap disconnected from the tampon applicator.

Referring to FIG. 1C, tampon applicator package assembly 10 is shown with cap 14 disconnected from tampon applicator 12. Tampon applicator 12 has plunger 18 in a stored position. Prior to use, telescoping portion 21 of plunger 18 and pledget 13 (FIG. 2) are housed in barrel 16. Plunger 18 is moved to the use position by applying a force to end portion 23 in a direction shown by arrow B in FIG. 1C moving end portion 23 away from barrel 16. When plunger 18 is in the use position, plunger 18 is adjacent pledget 13 and the user can apply the force to end portion 23 to move telescoping portion 21 in the direction shown by arrow A in FIG. 1A to move the pledget through insertion tip 20 into the body of the user. In another embodiment, cap 14 may be connected to a plunger receiving end 17 instead of end portion 23 of plunger 18. In this latter embodiment, plunger receiving end 17 and/or cap 14 will be provided with one or more structures 11. "Structures" is hereinafter defined to include, without limitation, one or more protrusions, slits, ridges or other type structure(s) that will, amongst other things, become apparent to one skilled in the art based upon the disclosure that follows. The Structures provide plunger receiving end 17 and cap 14 with an at least partial mating engagement. "Mating engagement" is hereinafter defined to include, without limitation, a friction-fit, snap-fit, button-fit, a detent, a threaded connection, a bayonet connection, and other connections, or any combinations thereof that will become apparent to one skilled on the art based upon the disclosure that follows.

Figure 1D:
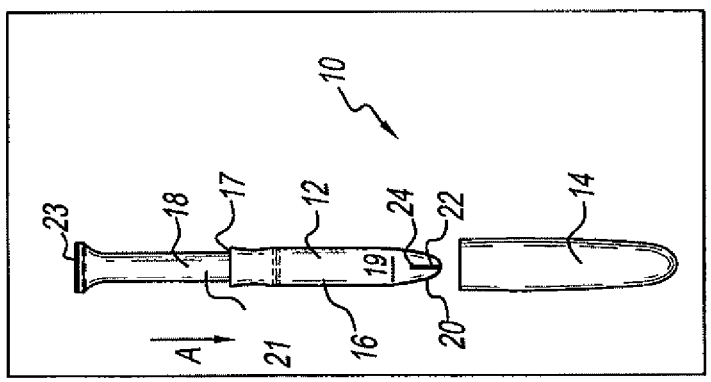
FIG. 1D is an inverted top view of the cap of FIG. 1A.

Referring to FIG. 1D, tampon applicator package assembly 10 has tampon applicator 12 connected to cap 14 and plunger 18 in the stored position. End portion 23 of plunger 18 may be sized so that, when cap 14 is connected to tampon applicator 12, at least a portion of end portion 23 is flush with cap 14. Tampon applicator 12 is connected to cap 14 so that barrel 16 is housed in cap 14. For example, cap 14 and end portion 23 are sized to form a friction fit, or end portion 23 has groove and cap 14 has a Structure that fits in the groove forming a snap fit so that a predetermined force applied by user to end portion 23 in a direction shown by arrow C disconnects cap 14 from end portion 23.

Figure 2:
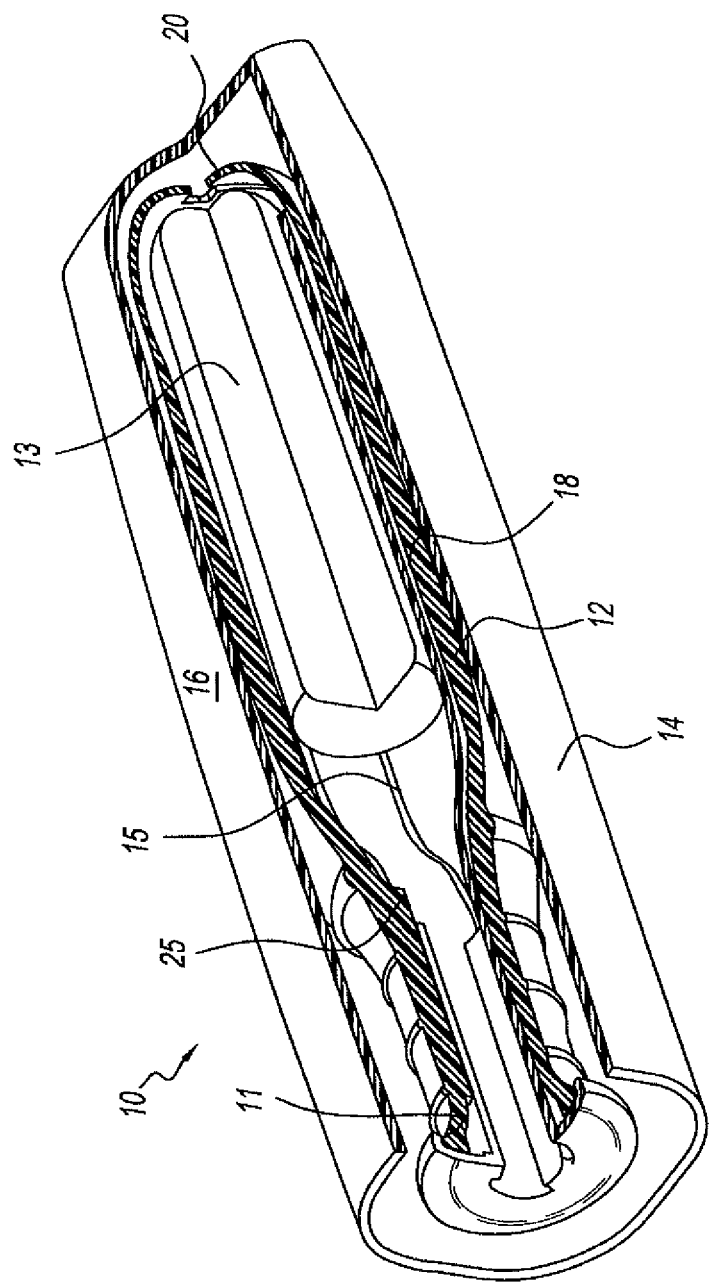
FIG. 2 is a cutaway perspective view of the tampon applicator package assembly of FIG. 1A having the plunger in the stored position and the cap connected to the tampon applicator.

Referring to FIG. 2, plunger 18 may have a slit 15 on one side or both sides to enclose a pledget 13 in barrel 16. In other embodiments, there may be a plurality of slits 15 along at least a portion of the length of the plunger 18 such that the plunger 18 with a plurality of slits 15 encloses pledget 13 in barrel 16. In other words, plunger 18 may have one or more slits 15 along at least a portion of the length of the plunger such that the plunger 18 at least partially encloses pledget 13, where the plunger is enclosed within barrel 16. Pledget 13 can be inserted through insertion tip 20 urging and opening plunger 18 to open along slit 15. Alternatively, pledget 13 can be inserted through insertion tip 20 and thereafter plunger 18 can be forced to open around pledget 13 via one or more slits 15. Structure 11 can further function as a stopping mechanism 25, that may be shaped similar to a shelf, can be added to barrel 16 to keep pledget 13 forward when plunger 18 is pulled out of barrel 16 to the use position. Plunger 18 shown in FIG. 2 may have end portion 23 as shown in FIG. 1A. There are alternative stopping mechanisms, such as ridges inside the barrel 16 or outside the plunger, to keep pledget 13 in place until the user deploys the plunger 18 as desired. Once plunger 18 is pulled out, there are other stopping mechanisms 25, such as inside ridges or shelves on the inner surface of barrel 16 or outside ridges or shelves on the outer surface of the plunger 18, to keep the plunger 18 from disengaging from the barrel 16.

Referring to FIGS. 3A-3D, cap 14 is connected to a cap cover 14A instead of end portion 23. Cap cover 14A can be made so that opening 29, shown in FIG. 3B, is disposed in the middle of the cap cover 14A. This structure allows a perforated seal or sticky tab 31 to be placed at a bottom of cap cover 14A to at least partially seal and keep cap 14 closed, ensuring the user that the tampon applicator package assembly's 10 contents are clean and that the tampon applicator package assembly 10 has not been opened previously. As used herein, the term "sticky tab" is defined to include, without limitation, a sticker, label, an adhesive-backed sheet, a heat-sealed or ultrasonically welded paper or laminate, or any other material providing at least partial seal and/or visual indication that the assembly has not been tampered with. In some embodiments, a full seal is provided. In some embodiments, adhesive on seal or sticky tab 31 may be provided or placed so as to stick to a string 13A connected to pledget 13 (see, e.g., FIG. 2) and threaded through plunger 18, and the adhesive on seal or sticky tab 31 pulls out at least a portion of string 13A as an at least partial seal or sticky tab 31 is opened, thereby making string 13A visible and reachable to the user. This enables string 13A to stay in tampon applicator package assembly 10, keeping the string 13A discrete and sanitary. Alternatively, plunger 18 can be manufactured closed at end portion 23 to protect string 13A from contamination. Plunger 18 can be made from a transparent material to enable the user to view string 13A before use to alleviate worries about the presence and reachability of string 13A. String 13A can be made from a springy material or can be wax coated that enables it to be easily packed into plunger 18. Referring to FIG. 3B, a fragrance strip 33 can placed in or on cap cover 14A to give a "scented" product experience to users who do not like placing scented pledgets into their bodies. Fragrance strip 33 placed in or on cap cover 14A also gives assurance to the user that the package has not been opened before. Further, fragrance strip 33 also provides a clean and fresh user experience. One skilled in the art understands that fragrance strip 33 can be placed almost anywhere on tampon package applicator assembly 10 and, furthermore, that in the alternative to fragrance strip 33, fragrance can be manufactured, added or molded into one or more portions of the tampon package applicator assembly 10. Alternatively, cap cover 14A can be a part of the plunger 18 (i.e. a one-piece plunger 18 (see, e.g., FIG. 1)) or snap onto the end portion 23. Similar to adding fragrance strip 33 to the bottom cap 14A (FIG. 3B), fragrance strip 33 can be placed in cap 14 (FIG. 1A), on at least partial seal or sticky tab 31 and/or on all other variations of the cap cover 14A to provide a scented product experience to users who do not like using scented tampons (i.e. because the fragrance is too much for the length of time the tampon is in the body, the user is allergic to the fragrance, and other like factors). Fragrance strip 33 also provides a fresh, hygienic and clean experience as the scent is released as the user opens tampon applicator package assembly 10.

In alternative embodiments of tampon applicator package assembly shown and described with respect to FIGS. 3A-3C, cap cover 14A may connect to end portion 23 via at least partial mating engagement, or similar design while cap 14 and plunger 18 can at least partially, matingly engage via similar means. Still alternatively, bottom cap 14A at least partially, matingly engages cap 14 and also at least partially, matingly engages plunger 23. One embodiment of such a connection is shown in, and described with respect to, FIG. 12C.

Referring again to FIGS. IA-1D, plunger 18 can be moved from the stored position to the use position once cap 14 is at least partially disconnected from tampon applicator 12, or while tampon applicator 12 is still connected to cap 14. Once cap 14 is disconnected from tampon applicator 12 and plunger 18 is moved from the stored position to the use position, tampon applicator 12 can be used to insert pledget 13 into the body of the user. After pledget 13 is inserted, the user may re-connect cap 14 to tampon applicator 18 to form the same configuration as prior to use for disposal of tampon applicator 12 and cap 14.

The present disclosure provides the user the advantage of removing the tampon applicator package assembly 10 from a stored position to a use position with virtually one hand and/or in a minimal number of actions. For instance, the tampon package applicator assembly 10 can be held and opened in one hand of the user (see the embodiments described throughout the present disclosure for ways of opening cap 14). Once the cap 14 is opened to reveal at least the end portion 23 of plunger 18, the user can grasp or touch the end portion 23 of plunger 18 to enable the telescoping portion 21 of plunger 18 to be at least partially exposed from the barrel 16 that, in turn, is at least partially contained in cap 14. Once the plunger 18 is sufficiently exposed so that the plunger 18 is still at least partially contained in tampon applicator 12 but oriented so that plunger 18 is adjacent the pledget 13, tampon applicator 12 and plunger 18 are in a prepared position. The user can remove the tampon applicator 12 and plunger 18 in the prepared position and thereafter insert the tampon applicator 12 containing pledget 13 into the user's body. The user can accomplish the acts of preparing the tampon applicator 12 and plunger 18 and removing tampon applicator 12 and plunger 18 from cap 14 in a single motion, and thus in just one step. The user can thereafter remove the tampon applicator 12 from the body. In a further embodiment, the user can thereafter, with one hand and with a minimal number of steps or actions, place the used tampon applicator back into cap 14. In another embodiment, a soiled feminine hygiene product or other hygiene product such as, for example, another tampon, a wipe, a pledget, pessaries and/or suppository can also be placed into the cap 14 for discreet and/or hygienic disposal. In further embodiments comprising one or more cap covers 36 as shown in FIGS. 3C and 3D, the cap cover 26 that is at least partially disengaged from the cap 14 can be replaced thereby further containing the soiled article for more discreet and/or more hygienic disposal.

In other words, the user can accomplish the task of opening the tampon applicator package assembly 10, preparing the tampon applicator 12 for insertion, inserting the tampon applicator 12 into the body, and removing the used tampon applicator from the body in just four (4) steps. Further, the user can thereafter dispose of the tampon and/or tampon applicator 12 in just two additional steps for a total of six (6) steps. For instance and as described throughout the present disclosure, once the tampon package applicator assembly 10 is at least partially opened, the user can remove the tampon applicator 12 so that it is removed and prepared for insertion into the body in one further step; this avoids the user having to prepare the pledget 13 and/or tampon applicator 12 in several steps. Additionally, due to the present disclosure's tampon applicator package assembly 10, the used tampon applicator 12 can be, in one step, easily replaced into the vacated tampon applicator package assembly 10 (thereby eliminating the need of the prior art wrappers of re-opening and/or holding the wrappers open in order to permit replacing the used tampon and/or tampon applicator into the vacated prior art wrapper). As such, the present disclosure's tampon applicator package assembly 10 can reduce the number of steps or actions the user must accomplish in order to utilize a tampon. Furthermore, this utilization is accomplished virtually or almost solely with one hand.

Cap 14, amongst other components of tampon applicator package assembly 10, can be made from one or more plastics, such as polyethylene, polypropylene, polybutylene, polystyrene, polyvinylchloride, polyacrylate, polymethacrylate, polyacrylonitrile, polyacrylamide, polyamide, nylon, polyimide, polyester, polycarbonate, polylactic acid, polyhyroxyalkanonate, ethylene vinyl acetate, polyurethane, silicone, thermoplastic elastomers, thermoplastic starch, t-polyisoprene, derivatives thereof, copolymers thereof, mixtures thereof, or any other suitable plastic material. Alternatively, cap 14, amongst other components of tampon applicator package assembly 10, can be made from a non-polymer material such as paper, paperboard, cardboard, cellulose (such as molded cellulose), metal, textile, wood or any combination thereof. Cap 14, amongst other components of tampon applicator package assembly 10, can be laminated, as opposed to single layer. In certain embodiments, additives can be included to alter or enhance certain material properties. Suitable additives include, but are not limited to, one or more mold release agents, anti-slip agents, surface energy modifiers, non-organic fillers, and/or any other suitable additives, or any combination thereof. Cap 14, amongst other components of tampon applicator package assembly 10, can have different coatings applied thereto for ease of use and decorating purposes. The material of cap 14, amongst other components of tampon applicator package assembly 10, can be biodegradable, compostable or flushable. The material of cap 14, amongst other components of tampon applicator package assembly 10, can be made using various manufacturing techniques including, but not limited to, injection molding, extrusion molding, blow forming and thermoforming, injection blow molding, rotational molding, transfer molding, co-molding, over-molding, casting, calendaring, coating, compression molding, laminating, pultrusion, slush molding, transfer molding, contact molding, metal forming processes and dipping, or any combination thereof. Barrel 16, plunger 18 and cap 14 can be made from different materials, and/or can be made up of different colors. A cross-sectional shape of cap 14 can be, without limitation, round having a constant or changing diameter, semicircular, rectangular, polyhedral, prismatic, triangular, may have a perimeter that is undulating, toothed or other geometry, or any combination of any of the foregoing. Cap 14 can be shaped so that it prevents tampon applicator package assembly 10 from rolling when placed horizontally. Cap 14 can be opaque or transparent, can be printed/decorated, and can be manufactured with relief surfaces to control and improve the visual appearance and appeal, or any combinations of the foregoing. Cap 14 can be decorated using several different methods including, but not limited to, in-mold texture change, printing, in-mold labeling, heat transfer foil, applying a printed label, embossing, etching, shrink wrapping, selective polymer addition, co-molding, bleaching, over-molding, or any combination thereof. The shape and decoration (or look) on cap 14 can be chosen obfuscate that it is a tampon. For example, cap 14 can have the look of a cosmetic object, such as a lipstick or of any ordinary object, such as, but not limited to, a flashlight or a lighter. One skilled in the art understands that the present disclosure is directed to a tampon package applicator assembly 10 whose aesthetics and/or otherwise visual appearance are other than that of a tampon package. In other words, the look of tampon applicator package assembly 10 serves to alleviate or eliminate the apprehension or embarrassment felt by the user due to being seen with a tampon by another. Also, all variations of cap 14 can look shiny, matte, contain a graphic or image, or a combination thereof, to further the desired aesthetics.

Figure 4:
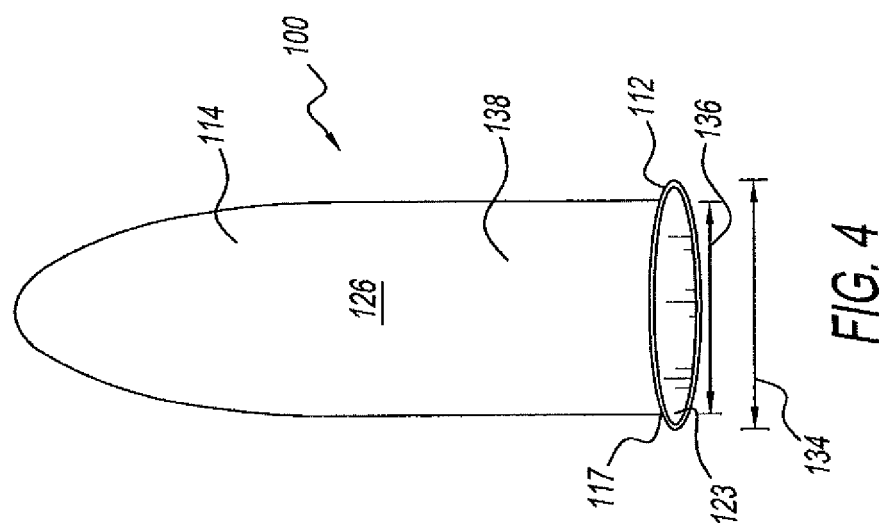
FIG. 4 is a side view of another embodiment of a tampon applicator package assembly of the present disclosure with a tampon applicator having the plunger in a stored position and a cap cover of a diameter greater than the cap connected to the tampon applicator.

Referring to FIG. 4, a tampon applicator package assembly 100 is modified from tampon applicator package assembly 10. Tampon applicator package assembly 100 has a tampon applicator 112 and a cap 114 having a cap body 126. Tampon applicator 112 has a plunger 118 having an end portion 123. Tampon applicator package assembly 100 is similar to tampon applicator package assembly 10; however, at least a portion of end portion 123 of a plunger 118 has a greater diameter 134 than the diameter 136 of cap 114. Cap body 126 has an outer surface 138 opposite an inner surface (not shown). In the embodiment shown in FIG. 4, end portion 123 has threads (not shown) that mate with threads (not shown) on cap 114. A portion of the inner surface 124 of cap wall 126 has internal first threads. A portion of end portion 123 has external second threads. The second threads mate and connect to the first threads to connect end portion 123 to cap 114 so that the portion of end portion 123 having the second threads is in cap 114 when cap 114 is connected to tampon applicator 112. Alternatively, cap 114 and end portion 123 can be connected by a hinge, quarter-turn stopped similar to a bottle cap, be otherwise at least partially matingly engageable, or otherwise mechanically fit together. Cap 114 can be similarly connected to a plunger receiving end 117 disposed inside of cap 114 instead of to end portion 123 of plunger 118. In this latter embodiment, the plunger receiving end 117 and/or cap 114 will be provided with a Structure, such as, one or more protrusions, slits, ridges or other type structure(s) that will provide the plunger receiving end 117 and cap 114 with an at least partially mating engagement or other connection(s) as will become apparent to one skilled on the art based upon the disclosure that follows. End portion 123 can alternatively be a part of the plunger 118 (one-piece plunger) or can have a cap cover 36 (see FIGS. 3A-3D) that can be snap-fit onto the end portion 123. The cap cover 36 can be larger in size than the diameter of cap 114. The cap cover 36 can have second threads such as described with respect to end portion 123 that connect to the first threads on cap wall 126 when cap 114 is connected to the tampon applicator 112. One skilled in the art understands that the cap 114, cap cover 36 and/or plunger receiving end 117 can at least partially have a mating engagement as shown and described throughout the present disclosure, any combinations thereof and/or equivalents of those shown and described herein.

Figure 5D:
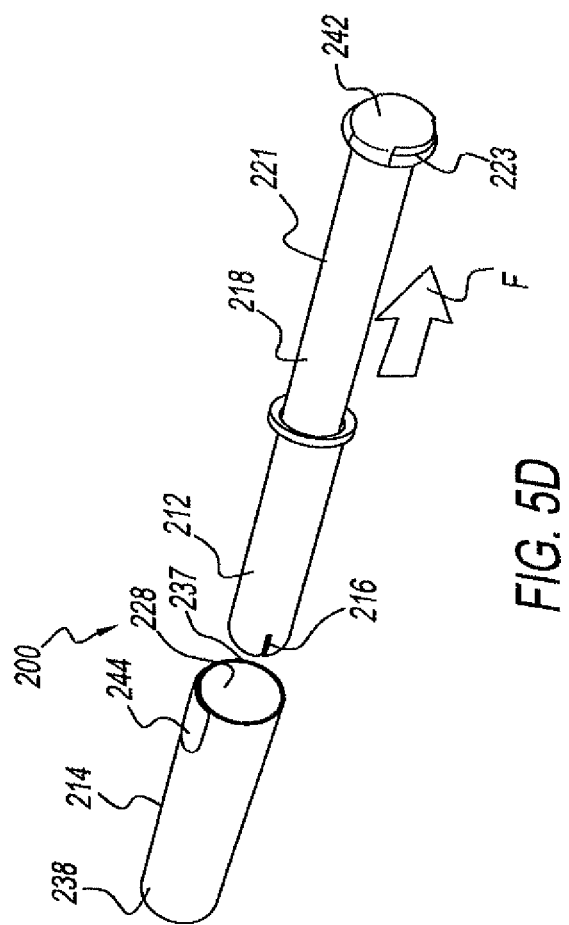
FIG. 5D is an exploded, rear perspective view of the tampon applicator package assembly of FIG. 5A with the tampon applicator having the plunger in the use position and the cap separated from the tampon applicator.

Referring to FIG. 5A, a tampon applicator package assembly 200 is modified from tampon applicator package assembly 10. Tampon applicator package assembly 200 has a tampon applicator 212, a cap 214 having a cap body 226 and cap opening 228 (shown in FIG. 5D), and a connector 240. Connector 240) has a middle portion 242 (shown in FIGS. 5B-5D) and side portions 244. Connector 240 can comprise a sticky tab. For instance, middle portion 242 and/or one or more of side portions 244, and any combinations thereof, can comprise a sticky tab. Connector 240 can, in some embodiments, provide at least a partial seal so that tampon applicator 212 is enclosed in the cap 214. In some embodiments, a full seal can be provided. As shown in FIG. 5D, tampon applicator 212 has a barrel 216 and a plunger 218. Plunger 218 has a telescoping portion 221 and an end portion 223. End portion 223 may have a cross-sectional shape that may be, without limitation, circular, semicircular, rectangular, polyhedral, and/or triangular, may have a perimeter that is undulating, toothed or other geometry, or any combinations thereof. End portion 223 may have ridges or another feature that prevents tampon applicator package assembly 200 from rolling when placed horizontally. Tampon applicator package assembly 200 is similar to tampon applicator package assembly 10; however, connector 240 is connected to end portion 223 and cap 214 to connect cap 214 to tampon applicator 212 so that cap 214 encloses barrel 216 prior to use. Connector 240 is a flexible material that connects to cap 214 and end portion 223, for example, by adhesive. Connector 240 may be integrally molded with either or both of cap 214 and applicator 212. In other embodiments, connector 240 may connect a cap 214 and cap cover (not shown in FIGS. 5A-5D), or a cap 214 and a plunger 218, or any combinations thereof.

Figure 11A:
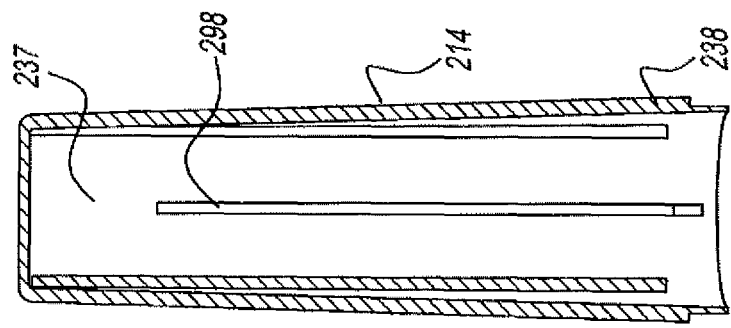
FIGS. 11A and 11B are schematic views of a cap of tampon applicator package assemblies of the present disclosure showing rib(s) disposed on the interior surface of the cap.

Referring to FIG. 5B, to go from "stored" position to a "prepared" position, the user disconnects cap 214. To disconnect cap 214 and tampon applicator 212, the user rotates cap 214 and end portion 223 relative to one another as shown by arrow D. One skilled in the art understands the present disclosure is not limited to embodiments where the cap 214 is connectable to and/or removable from the end portion 223 by rotatable and/or threaded means, and that this embodiment is merely exemplary. End portion 223 can be the size of or larger than cap 214 for ease of holding. Middle portion 242 of connector 240 maintains connection to end portion 223 and side portion(s) 244 maintain connection to cap 214 so that during rotation middle portion 242 is separated from side portion(s) 244 to allow end portion 223 of plunger 218 to move away from cap 214 as shown by arrow E in FIG. 5C. Barrel 216 can be maintained in cap 214 while end portion 223 is moved away from cap 214 to a "use" position by a built in Structure acts as a stopping point and/or stopping mechanism 298, such as a protrusion, as exemplified in FIG. 11, that extends from an inner surface 237 that is opposite to an outer surface 238 of cap 214 as shown in FIG. 11A.

Figure 11:
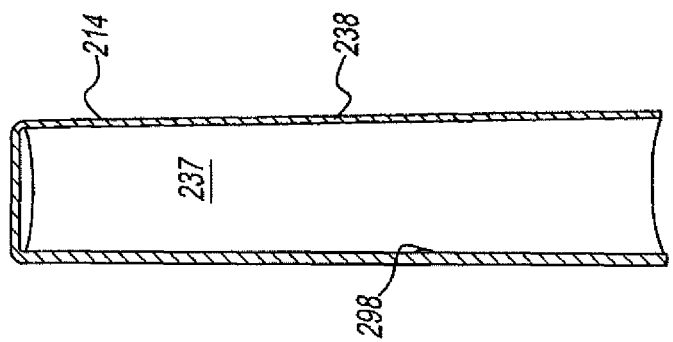
FIG. 11 is a schematic view of a cap of a tampon applicator package assembly of the present disclosure showing a protrusion disposed on the interior surface of the cap.

Referring to FIG. 5D, after plunger 218 is in the "prepared" position, the user moves plunger 218 to a "use" position by continuing to apply a force to move end portion 223 of plunger 218 away from cap 214 as shown by arrow F, move barrel 216 past a protrusion 298, as shown in FIG. 11, and move barrel 216 out of cap 214 so that tampon applicator 212 is ready for use by the user. The user can accomplish the "prepared" position in one single movement, thereby providing a tampon applicator 212 in a "use" position quickly and easily. After the pledget (not shown in FIGS. 5A-5D) is used, cap 214 is connected to tampon applicator 218, and thus provide the same configuration as prior to use, for disposal of tampon applicator 212 and cap 214. Alternatively, cap 214 connects to a cap cover that is separate from end portion 223 so that cap 214 and the separate cap cover entirely surround tampon applicator 212.

Referring to FIGS. 6-10, there are shown alternative embodiments of the tampon applicator package assembly of FIGS. 5A-5D. For the sake of clarity, the element numbers in FIGS. 6-10 that are similar to those of FIGS. 5A-5D have not been repeated. Only elements of FIGS. 6-10 that are particularly described therein are indicated with element numbers.

Figure 6A:
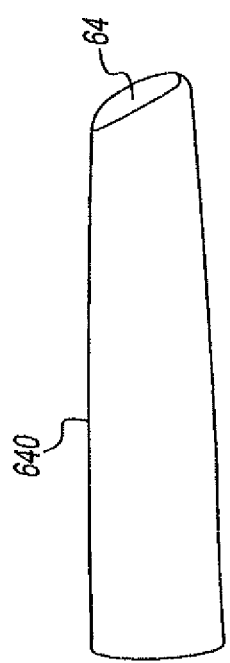
FIGS. 6A, 7A, 7B, 8A, 9A and 10A are close up views of certain elements and features of FIGS. 6, 7, 8, 9 and 10, respectively.
Figure 7:
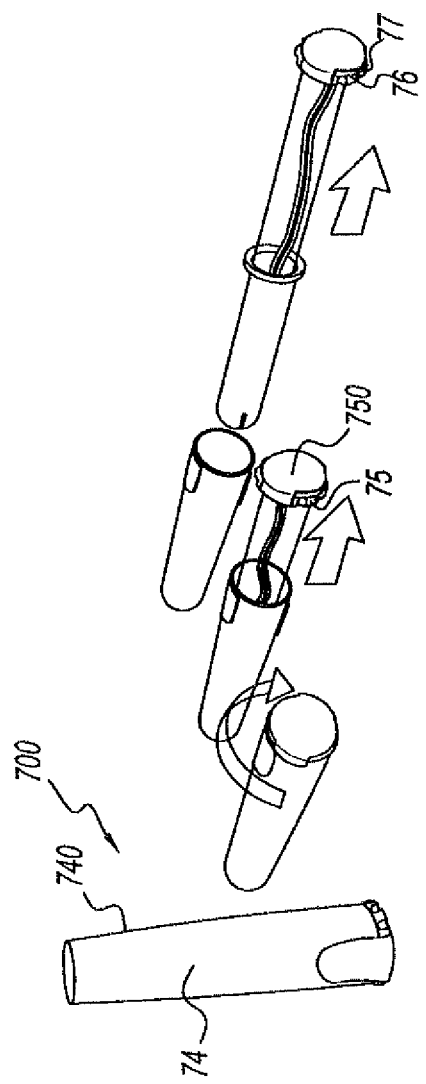
Figure 8:
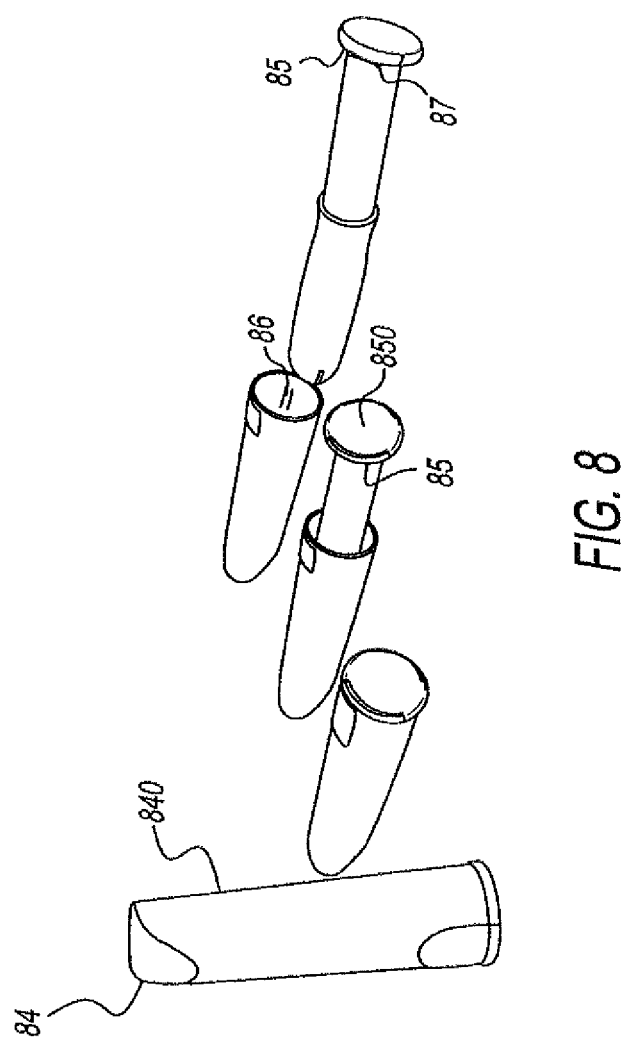
Figure 9:
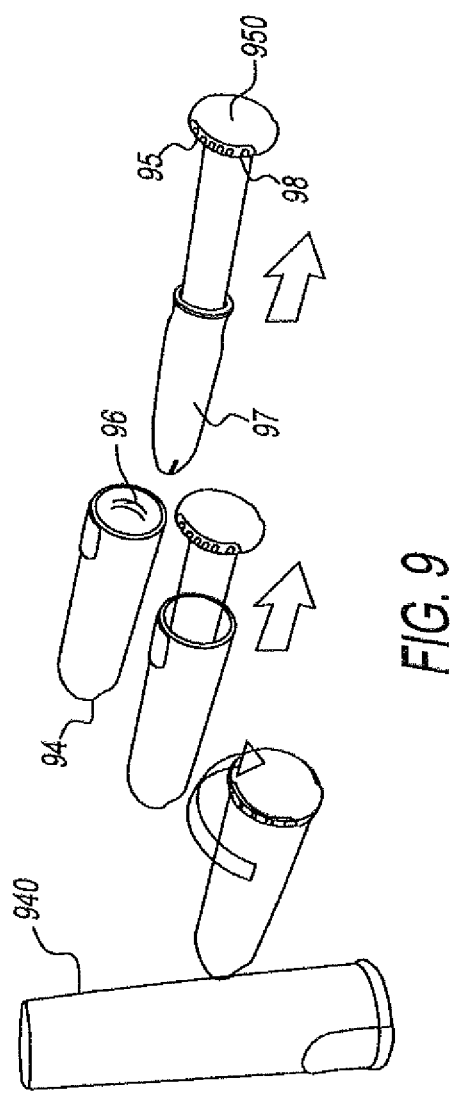
Figure 10:
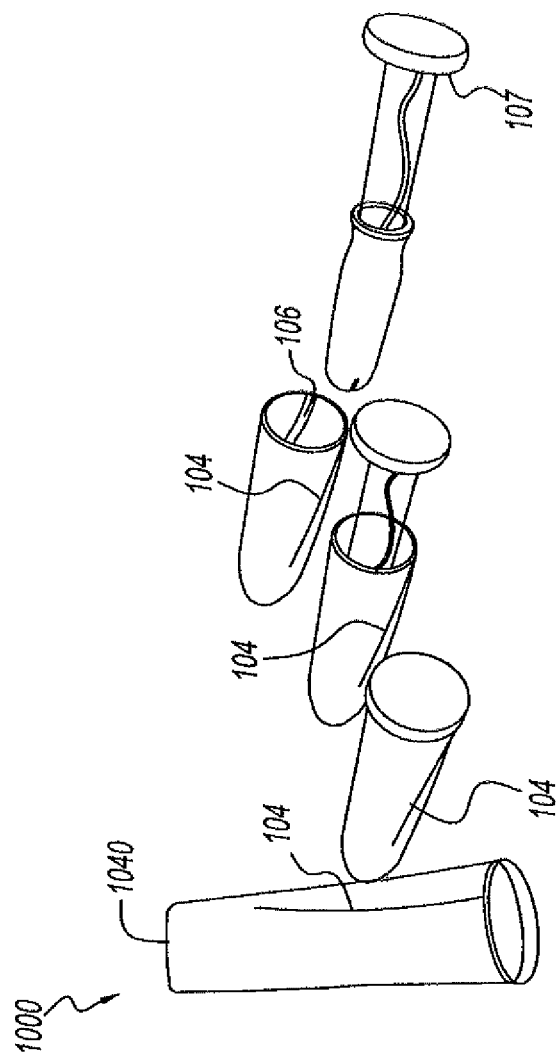

FIGS. 6-7 show different shapes and decorations of the caps. FIGS. 8-10 show different shapes and decorations of the caps as well as an alternative compact applicator with a tapered barrel and transparent plunger. One skilled in the art understands plungers can be translucent, solid, patterned, have other visual stylistic elements, and any other shape or decorative effect. Although compact applicators have been heretofore described in detail, one skilled in the art that will recognize that both regular tampon applicators and compact tampon applicators are in the scope of the present disclosure. FIGS. 6-10 are shown additionally for the purpose of demonstrating different pledget string attachments that make the pledget string accessible to the user but, at the same time, keep the pledget string from being visible outside of the tampon applicator package assembly. This feature adds to the discreet appearance of the tampon applicator package assembly.

Referring FIGS. 6 and 8, top cap 640, 840, respectively, can have an angled top 64, 84, respectively, and can be shaped like a lipstick, any other cosmetic object, or any other object that is similarly sized to accommodate one or more feminine care devices or other hygiene devices used for insertion into the body that may be found in a hand-bag, purse, pocket book, briefcase, backpack, tote bag, or satchel.

Figure 8A:
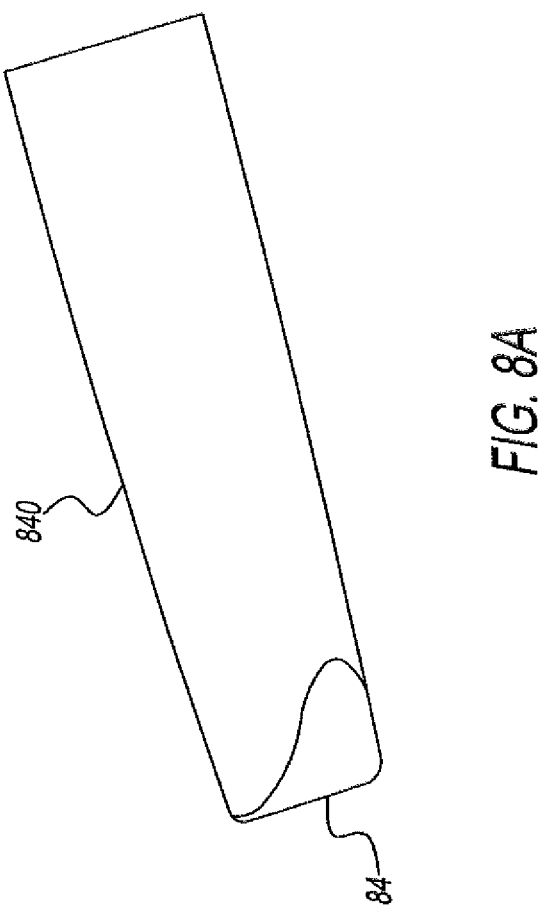

"Personal Item" is hereinafter defined to encompasses, without limitation, any cosmetic object or any other object found in a carrying vessel, as defined below, so that a tampon package applicator assembly 10 could be fashioned after such object and accommodate one or more feminine care devices or other hygiene devices used for insertion into the body. "Carrying vessel" is hereinafter defined and encompasses, without limitation, any hand-bag, purse, pocket book, clutch, briefcase, backpack, tote bag or satchel that is similarly-sized and/or similarly-shaped to accommodate Personal Items. One skilled in the art understands that the tampon package applicator assembly 10, 100, 200 of the present disclosure can be geometrically modified such that it emulates the typical size and shape of any Personal Item as described herein that is found in a carrying vessel. Preferably, the tampon applicator package assembly is geometrically sized and shaped so that it emulates the typical size and shape of a Personal Item that a woman carries with her into a restroom. The angle of angled top 64, 84, respectively, defines an angle that is between 0.10 to 90°, and preferably between 5°-40°. FIGS. 6A and 8A are close up views of angled top 64, 84.

Figure 7B:
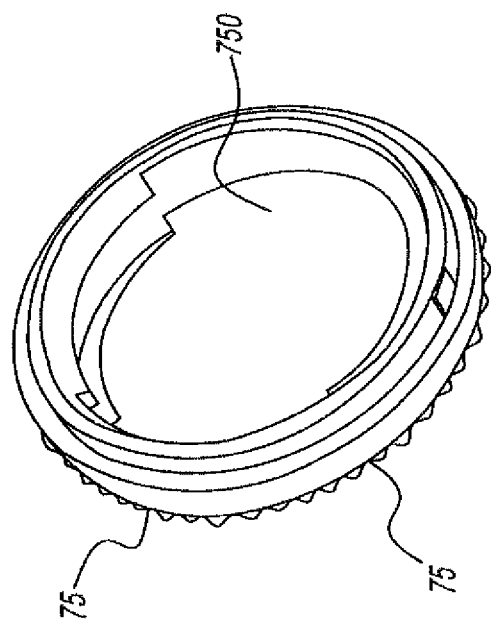
Figure 7A:
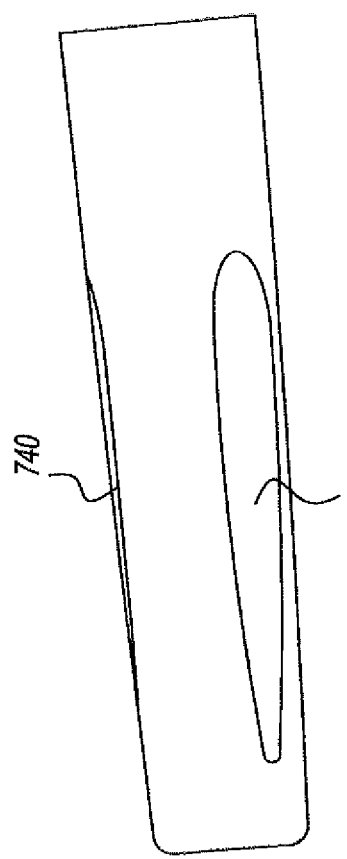
Figure 10A:
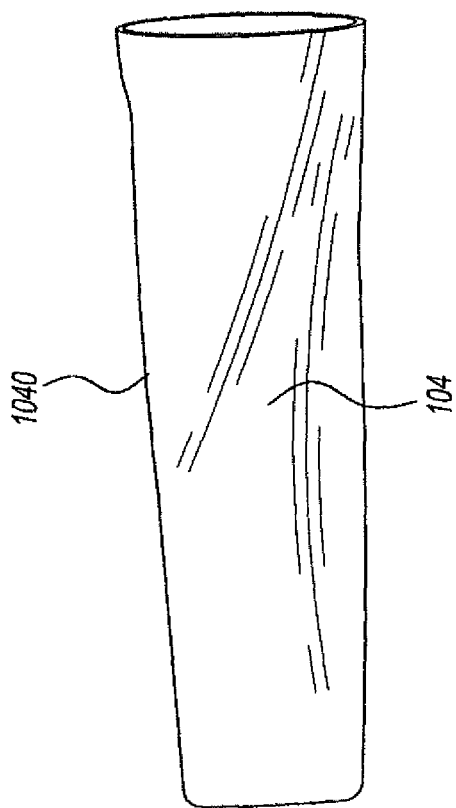

Referring to FIGS. 7 and 10, top cap 740, 1040, respectively, can be provided with an undulating surface, indents or raised features (including, but not limited, to one or more swirls, ridges, dents and strips 74,104, respectively) to prevent the top cap from rolling when placed on its side, and, preferably, to enhance aesthetics. FIGS. 7A and 10A are close up views of indents/raised features 74, 104.

Figure 9A:
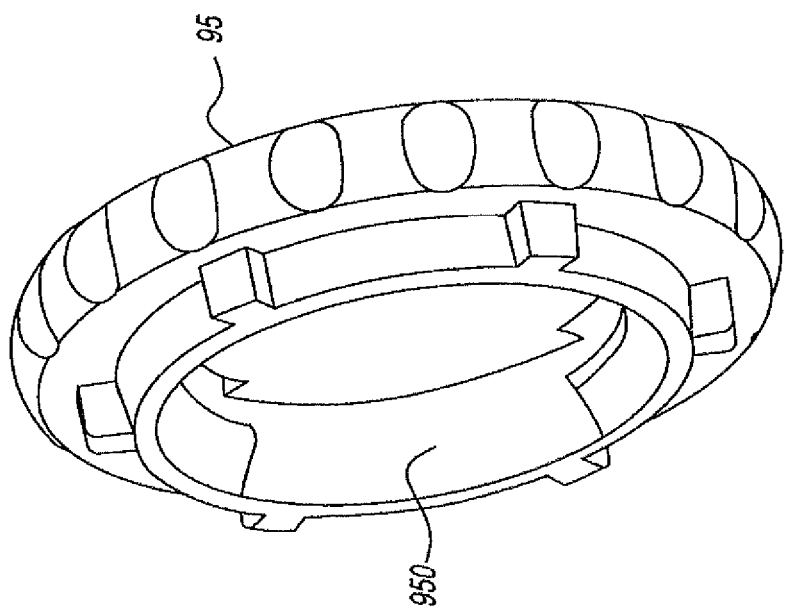

Referring to FIGS. 7 and 9, cap cover 750, 950, respectively, has ridges 75, 95, respectively, to enhance the gripability of the cap cover 750, 950 by the user and also to assist in preventing rolling of tampon applicator package assembly 700, 900 when placed on a flat surface. The number of ridges 75, 95 on the cap covers 750, 950 can range from 1 to 50, preferably from about 10 to 20. Likewise, the number of recesses/grooves 85 between ridges 75, 95 on the cap cover 750, 950 can also range from 1 to 50, preferably from about 10 to 20. The depth of the recess/groove 85 between each pair of ridges 75, 95 can be between 0.001" to 1", preferably between 0.01-0.1". FIGS. 7B and 9A are close up views of ridges 75,95. One skilled in the art understands that the ridges 75, 95 and recesses/grooves 85 can be convex and thus extend from the perimeter of cap cover 750, 950, can be concave and thus extend into the perimeter of cap cover 750, 950, or any combinations thereof.

Referring to the tampon applicator package assembly of the present disclosure, but specifically to FIGS. 6-10, tampon applicator package assembly 700, 1000, can be sized so that it fits comfortably in places where the user will place and carry it, such as, for example, in a carrying vessel, a female hand and/or a jean pocket. In all embodiments of the present tampon applicator package assemblies, the diameter of the cap can be from about 0.1 to 2 inches, preferably from about 0.4 to 0.9 inches. Similarly, in all embodiments of the present disclosure, the length of the cap for a compact applicator can be from about 0.2 to 6 inches, preferably from about 1 to 3 inches. The wall thickness of the cap can be from about 0.001 to inches, preferably from about 0.01 to 0.5 inch for durability. The elastic modulus of the cap can be from about 0.001 to 1000 GPa, preferably from about 0.008 to 100 GPa. If the cap is made of plastic, the surface roughness can be from about 0.1 to 1000 micron inches, preferably from about 1 to 100 micron inches. The surface roughness can be adjusted to enhance the aesthetics and user appeal, as well as application of designs.

Figure 11B:
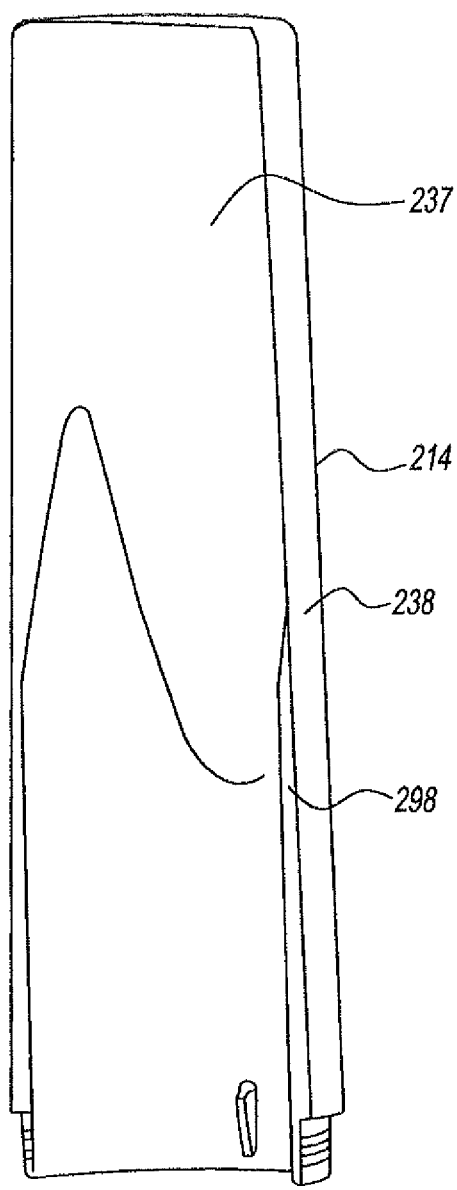

Referring again to FIGS. 8-10, a Structure (such as, for example, one or more ribs or grooves along a longitudinal axis direction) e.g., 86, 96, 106, respectively, can be built on the inner wall of the cap to help guide and/or position the applicator into the cap (see. e.g., FIG. 11B). In other embodiments, the inner wall of the cap can be an undulating surface, have teeth or other projections and recesses that help guide and/or position the applicator in the cap. The barrel can have structures, such as, opposing grooves or ribs, e.g., 97, that, in some embodiments, are designed and configured to at least partially, matingly engage with the ribs (i.e. 86, 96 and/or 106) or grooves on the inner wall of the cap. This design makes it easier for the user to place the applicator back into the cap for disposal. A cap cover can be attached to the plunger (rather than being end portion 223 of the plunger (see FIG. 5A)). The cap cover can attach to the plunger end portion by an at least partial mating engagement, or any combination thereof. The force to remove the cap cover from the plunger is from about 0.1 to 100 N, preferably from about 1 to 50 N, more preferably from about 1 N to 10 N. and most preferably from about 5 N to 10 N, to prevent the user from pulling off the cap cover rather than removing the plunger from the cap. Cap can attach to the cap cover in several ways including, but not limited to, a mating engagement, mechanical fit, magnetically, or any combination thereof. Similar to end portion 223, shown in FIG. 5A, of the plunger, the cap cover can have a cross-sectional shape that can be, without limitation, circular, semicircular, rectangular, polyhedron, triangular, or any combination thereof, for ease of holding by the consumer and to prevent tampon applicator package assembly from rolling when placed horizontally.

Referring again to 5A-5D and FIGS. 6-10, to disconnect the cap cover from the cap, the user rotates the cap and cap cover relative to one another as shown by the arrow D in FIG. 5B and similar arrows shown in FIGS. 6-10, to provide a twist-off force. This twist-off force is from about 0.01 lb.-in. to 100 lb.-in, preferably from about 0.1 lb.-in. to 10 lb.-in. The user removes the plunger as shown by the arrows E and F in FIGS. 5C-5D and similar arrows shown in FIGS. 6-10. During this step, the barrel remains in the cap due to a Structure (element 298 in FIG. 11) until sufficient force is applied to extract or remove plunger entirely from the barrel. The force to remove plunger from the barrel can be adjusted, depending on the size and location of the Structure 298, to between 0.01 N to 200 N, preferably from about 0.1 N to 30 N, more preferably from about 1 N to 10 N. Once the plunger is in the use position, the cap cover is moved away from the cap and applies a force from about 0.01 N to 200 N, preferably from about 0.1 N to 20 N, and more preferably from about 1 N to 10 N, to move the barrel past the protrusion so that the tampon applicator is ready for use. After the pledget is inserted into the body, the cap can be connected to the cap cover to form the same configuration as prior to use, and thus for disposal of tampon applicator package assembly. The force needed to place the applicator back into the cap is from about 0.01 N to 100 N, preferably from about 0.1 N to 20 N. and more preferably from about 1 N to 10 N. The cap cover can be snapped into the cap to form a lock mechanism. The lock mechanism can be designed so that the user hears a click sound once the assembly is closed (similar to a lip balm such as Chapstick®). The force to replace (i.e. such as by snapping the cap cover back onto the cap) the cap cover onto the cap is from about 0.01 N to 200 N, preferably from about 0.1 N to 40 N, and more preferably from about 1 N to 10 N. This ensures that the applicator will not fall out of the cap thereby assuring an improved and more sanitary disposal, and provides a tactile cue to the consumer that the tampon assembly is securely closed.

Referring once again to FIGS. 5A-5D and 6-10, the diameter of the cap cover is from about 0.01% to 50% smaller than the cap or from about 0.001% to 80%, preferably from about 1% to 30% larger than the cap, to provide easier gripping and holding. When the cap cover is larger than the cap, such a configuration provides for easy holding. The wall thickness of the cap cover is from about 0.001 to 1 inch, and preferably from about 0.01 to 0.1 inch. The length of the cap cover can be: from about 0.001% to 90% longer than the cap, or approximately the same as the cap, or from about 0.001% to 90% and preferably from about 0.01% to 50% shorter than the top cap. The cap cover can have one or more holes for the string attached to the pledget to be pulled through as shown in FIGS. 3B-3D. Alternatively, as shown in FIGS. 6-10, the cap cover can have a "notch" 65, 76, 87, 98 and 107, respectively, into which the pledget string is attached after from traversing a hollow plunger from the pledget to the bottom cap. Still further, the pledget string may be wrapped around a groove on the cap cover as shown as elements 66, 77 in FIGS. 6 and 7, respectively. Each embodiment described above provides for easy gripping of the pledget string by the user, while at the same time providing discreet storage of the pledget string in the tampon applicator package assembly. Also, it will be appreciated by one of ordinary skill in the art that all information including materials, manufacturing techniques, decoration techniques, mentioned in paragraph [0063] with respect to the cap apply as well to the cap cover.

Still further embodiment, cap and cap cover have different colors to enhance the "non-tampon-like" appearance of tampon applicator package assembly 10. Cap cover can be opaque or transparent, and/or can have printing and/or decorations to control and improve its visual appearance and appeal. Cap cover can be decorated using several different methods including in-mold labeling, heat transfer foil, applying a printed label, embossing, in-mold texture change, printing, etching, shrink wrapping, selective polymer addition, co-molding, over-molding, bleaching, or any combination thereof. The shape and decoration, as well as the color, on the cap cover can be similar to the cap and/or the barrel and/or the plunger and can be chosen to look like an everyday object in the purse, such as a lipstick, mascara, flashlight and lighter.

Referring once again to FIGS. 5A-5D, connector 240 is placed at the bottom of the end portion 223 to at least partially seal the tampon applicator package assembly 200. This ensures that the contents of the tampon applicator package assembly 200 is clean and has not been previously opened. In some embodiments, end portion 223 comprises a cap cover, or in other embodiments, end portion 223 at least partially matingly engages a cap cover. Connector 240 can be designed so that it completely seals the area between the cap 214 and end portion 223 and/or cap cover. This sealing will make tampon applicator package assembly 200 water-resistant and/or waterproof. As shown in FIG. 5A, connector 240 can be attached to the cap 214 and cap cover with adhesive or by other methods, such as shrink wrap and ultrasonic welding or a combination thereof. If connector 240 comprises a sticky tab (i.e. so that connector 240 is attached with an adhesive or has an adhesive backing), the adhesive strength is from about 0.01 N to 100 N, and preferably from about 0.1 N to 20 N, to prevent unintended pulling away from cap 214 and/or cap cover. Alternatively, connector 240 can be shrink-wrapped to at least partially seal the area between the cap 214 and the cap cover. The shape of the connector 240 can be similar to those shown in FIGS. 5A-5D and 6-10. Although directed specifically to the embodiments shown and described in FIGS. 5A-5D and 6-10, it will be appreciated and understood by one of ordinary skill in the art that the foregoing description applies equally to all connectors and sticky tabs mentioned previously, including those referred to in FIGS. 3A-3D, 13A-13B and 14A-14B.

Referring to FIGS. 5B-5C, the diameter of the middle portion 242 of connector 240 can be equal to the diameter of the cap, or from about 0.001% to 90% and preferably from about 0.1% to 50% smaller than the diameter of the cap, or from about 0.001% to 90% and preferably from about 0.001% to 5% larger than the diameter of the cap. Referring to FIG. 5A, the length of side portions 244 can be from about 0.1 to 10 inches, and preferably from about 0.2 to 1 inches. Alternatively, side portion 244 can be, without limitation, circular, semicircular, rectangular, polyhedron, triangular, or combinations thereof. The location of connector 240 can be similar to that shown in FIGS. 5A-5D and 6-10. Alternatively, connector 240 can be parallel to (i.e., along a circumference or perimeter of the tampon applicator package assembly) the line joining the cap 214 to the cap cover. Connector 240 that is placed along a circumference or perimeter of the tampon applicator package assembly can have perforations for twist open or can be peeled along the circumference or perimeter to open as shown in FIG. 14B. Alternatively, connector 240 can be placed perpendicular to the line joining the cap to the cap cover, or any other angle generally between parallel and perpendicular to the line joining the top cap to the bottom cap. A second connector similar to connector 240 can be attached anywhere on the cap 214 or the cap cover to enhance the aesthetics and help disguise tampon applicator package assembly 10.

Connector 240 can be made from various different materials including, but not limited to, flexible and rigid plastics, foil, cellulose-based films and paper, derivatives thereof, copolymers thereof, any mixtures thereof, or any other material known to those of skill in the art of making such connectors. Connector 240 can have a portion that can be peeled open along the circumference or perimeter and separated, in a manner similar to a milk jug peel away ring, at its lid. Connector 240 can be any color or any combination of colors including, but not limited to, gold and silver, and can have different decorations including, but not limited to, shiny and matte, or any combination thereof, to match the aesthetics of the cap and cap cover as well as disguise the tampon applicator package assembly as an ordinary object in the purse. Connector 240 can be perforated for ease of opening. The location of the perforation(s) (see, e.g., element 560 in FIG. 14B) can be anywhere between the cap 214 and the cap cover but, preferably at the line joining the cap 214 and the cap cover. The perforation(s) can be vertical or perpendicular to the cap 214 and cap cover or at an angle therebetween, or can have swirls, or can be a combination thereof. When present, the perforation(s) strength is from about 0.01 lb.-in to 100 lb.-in, and preferably from about 0.1 to 10 lb.-in. The tensile strength of connector 240 is from about 0.01 N to 500 N, and preferably from about 0.1 N to 100 N. The thickness of the connector is from about 0.00001 to 1 inch, and preferably from about 0.0001 to 0.1 inches.

Referring to FIG. 11, one or more protrusions 298 can be on one side or on opposite sides of cap 214. Each protrusion or the one or more protrusions 298 can be a small bump to maintain barrel in cap 214 while end portion of barrel is moved away from cap 214 to the use position. In alternative embodiments, cap 214 can have from about 2 to 20 protrusions. Preferably, cap 214 has from 5 to 10 protrusions 298. Protrusions 298 can be connected on the inside surface of cap 214, to form a ring-like structure. Protrusions 298 can extend from about 0.0001% to 40% of the maximum diameter of cap 214 to inhibit the premature expulsion of the barrel from cap 214. The protrusions 298 can be located from about 0.001 to 5 inches, and preferably from about 0.1 to 1 inch from the top end of the cap. Alternatives to the protrusions include a single thread that is located in the inner wall of the cap or a springy tab that can be pushed from outside to allow the barrel assembly easily be deployed. Any one of these alternatives, as well as the protrusions, can be used alone or in combination. Of course, it will be appreciated by one of ordinary skill in the art that, although protrusion 298 has been discussed specifically in conjunction with FIG. 11, all possible embodiments of protrusion including those as described herein may be used with any embodiment of tampon applicator package assembly 10.

Referring to FIGS. 11A and 11B, cap 214 can have structures, such as, for example, one or more long, extended strip(s), ribs and/or ridges to maintain barrel in cap 214 as shown in FIGS. 8, 9 and 10 as elements 86, 96 and 106, respectively, thereby functioning in a manner similar to protrusion(s) 298 described with respect to FIG. 11. In addition, strip(s) 86, 96, 106 can serve the additional function of providing "guides" for re-insertion of barrel 212 and plunger 218 into cap 214 for disposal after insertion of the pledget into the body of the user.

Figure 12C:
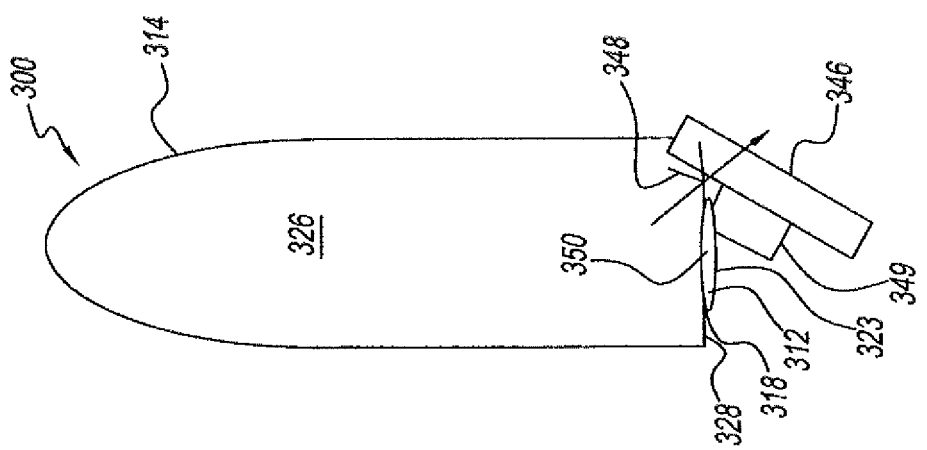
FIG. 12C is a side view of an alternative embodiment of the tampon applicator package assembly of FIG. 12A with the tampon applicator having the plunger in the stored position and the cap having an alternative cap cover in an open position.
Figure 12B:
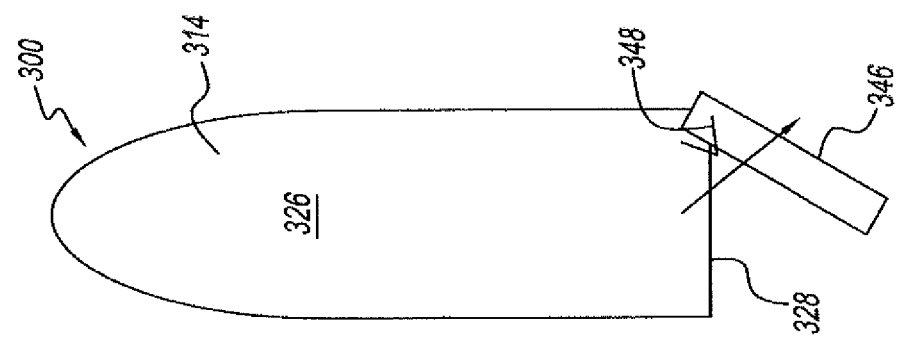
FIG. 12B is a side view of the tampon applicator package assembly of FIG. 12A with the tampon applicator having the plunger in the stored position and the cap having a cap cover in an open position.
Figure 12A:
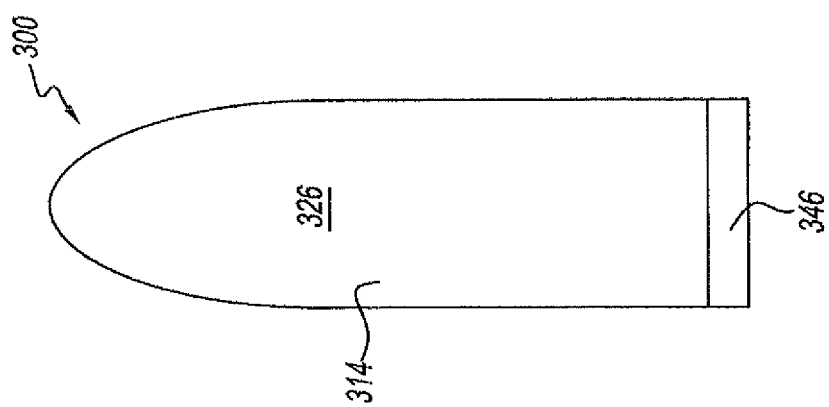
FIG. 12A is a side view of a cap of another embodiment of a tampon applicator package assembly of the present disclosure.

Referring to FIG. 12A, a tampon applicator package assembly 300 is modified from tampon applicator package assembly 10. Tampon applicator package assembly 300 has a tampon applicator 312 (shown in FIG. 12C), a cap 314 having a cap wall 326, and a cap cover 346 comprised of a door or flip top 346 connected to cap 314 by a hinge 348. Hinge 348 can include, without limitation, an articulation, an engagement mechanism or any other mechanism that provides at least partial attachment of one component to another. Hinge 348 can be integrally molded with one or more of the cap cover 346, cap 314, and/or plunger 318. Tampon applicator 312 has a plunger 318 with an end portion 323. Tampon applicator package assembly 300 is similar to tampon applicator package assembly 10, however, cap 314 and cap cover 346 entirely house tampon applicator 312. To access tampon applicator 312, cap cover 346 is moved from a closed position, as shown in FIG. 12A, away from cap 314 to an open position shown in FIG. 12B, so that tampon applicator 312 can be moved via cap opening 328 through cap wall 326. Cap cover 346 can be maintained in a closed position. For example, cap cover 346 and a portion of cap 314 adjacent cap opening 328 are sized to form a friction-fit between cap cover 346 and cap opening 328, or cap cover 346 can have groove and the portion of cap 314 adjacent cap opening 328 can have a protrusion that fits in the groove forming a snap-fit so that a predetermined force applied by the user moves cap cover 346 away from cap 314.

Referring to FIG. 12C, cap cover 346 has a cap cover protrusion 349, and end portion 323 of plunger 318 has a plunger opening 350. Cap cover protrusion 349 is inserted into plunger opening 350. Cap cover protrusion 349 and plunger opening 350 are sized so that cap cover protrusion 349 and plunger opening 350 form a friction fit. Alternatively, plunger opening 350 has a groove so that a protrusion on cap cover protrusion 349 fits within plunger opening 350 to form a snap fit or other at least partial mating engagement, so that moving cap cover 346 away from cap 314, end portion 323 is moved outside of cap 314 and cap cover protrusion 349 is disconnected from plunger opening 350 of end portion 323, to allow the user to withdraw tampon applicator 312 out of cap 314. Cap cover 346 with cap cover protrusion 349 is desirable when plunger 318 is moved out of cap cover 346 is simultaneously opens in one step (eliminating the normal extra step of reaching for and removing tampon applicator 312 from cap 314 and the telescoping of plunger 318 after removal of tampon applicator 312). Cap 314 can have a cut out that matingly engages with cap cover protrusion 349. Cap cover protrusion 349 is inserted into the cut out. Cap cover protrusion 349 and the cut out can be sized so that the cap cover protrusion 349 forms at least partial mating engagement with cover 314. When cap cover 346 is opened, the cut out enables the user to place her hands easily at the plunger end portion 323.

Figure 13B:
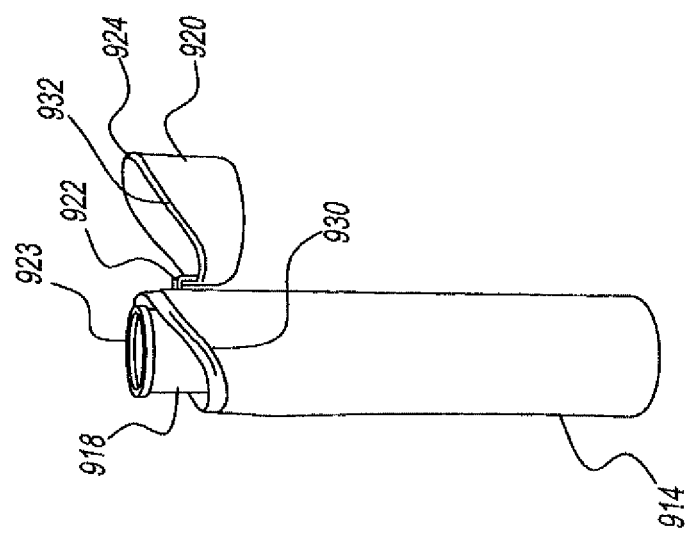
FIGS. 13A and 13B are side perspective-type views of alternative embodiments of a tampon applicator package assembly of the present disclosure.
Figure 13A:
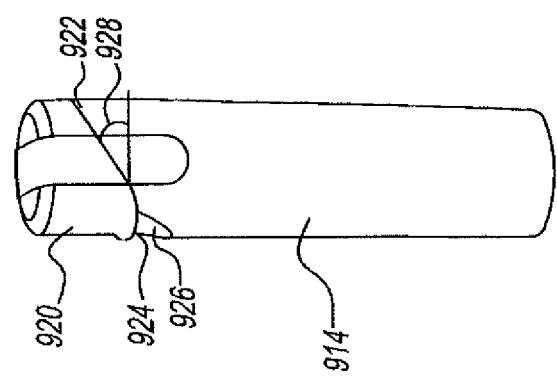

An alternative of the embodiment of FIGS. 12A-12C is shown in FIGS. 13A-13B. Tampon applicator package assembly 10 has a tampon applicator 918 that is placed in a cap 914 that has a flip top cap cover 920 connected to cap 914 with a hinge 922. Alternatively, cap 914 and flip top cap cover 920 can be connected through an at least partial mating engagement, instead of a hinge. In this instance, flip top cap cover 920 separates from cap 914 when the user pushes it open. To this end, flip top cap cover 920 is provided with a lip, groove, protrusion, projection or other Structure 924 that can be actuated by the finger of the user. Cap 914 has a mating lip, groove, recess, protrusion, projection, rib or other Structure 930. In some embodiments, cap 914 may have a concave portion and/or flip top cap cover 920 may have a convex portion. In operation, the user places her finger below lip 924 (or other structure) of flip top cap cover 920 and pushes it to open cap 914. The force to open flip top cap cover 920 can be from about 0.01 N to 200 N, preferably from about 0.1 N to 30 N, and more preferably from about 1 N to 10 N. The flip top cap cover opening angle 928 can be from about 1 to 99 degrees, and preferably from about 10 to 50 degrees, for the user to easily reach and grab the plunger end 928. In other embodiments, without limitation, FIG. 8A, the cap 914 and/or flip top cap cover 920 can have an angled feature to assist in at least partial separation and/or removal of the cap 914 and/or flip top cap cover 920, thereby at least partially exposing the contents of the cover 914. The location of the plunger end 928 can be positioned to enable the user to reach and pull plunger end 928 easily. The length of lip 924 (or other structure) is from about 0.001" to 0.5", and preferably from about 0.01 to 0.1 inches. The width of lip 924 (or other structure) is from about 0.01 to 2 inches, and preferably from about 0.1 to 1 inch. The height of lip 924 (or other structure) is from about 0.001 to 0.2 inches, and preferably from about 0.01 to 0.1 inches, so that the user can place her fingers below the lip easily. Preferably, flip top cap cover 920 remains connected to the cap 914 with hinge 922. Hinge 922 may be integrally molded with cap 914 and/or with flip top cap cover 920, or both. Then, the user pulls on plunger end portion 923 to move it away from cap 914. Structure, such as, for example, a protrusion or multiple protrusions, a rib or multiple ribs, placed on the inside wall of cap 914 (see, e.g., element 800 in FIG. 11A) maintain barrel (not shown in FIGS. 13A and 13B) in cap 914 as the plunger 918 is pulled. Once the plunger 918 is deployed, the user continues to pull on the plunger 918 to move the barrel past the Structures. After the applicator is completely out of cap 914, the pledget (not shown in FIGS. 13A and 13B) can be inserted for use. Thereafter, the used applicator (and/or other soiled feminine hygiene article, as the case may be) can be placed in cap 914 and flip top cap cover 920 is closed for clean and hygienic disposal. The force to close flip top cap cover 920 is from about 0.01 N to 200 N, preferably from about 0.1 N to 40 N, and more preferably from about 1 N to 10 N. The shape of flip top cap cover 920 and lip 924 can be any decorative shape, such as, for example, a flower or any other aesthetically designed/disguised shape or object, to enhance aesthetics. Alternatively or additionally, cap 914 and flip top cap cover 920 have mating Structures, such as lips 930 and 932, respectively, to provide a snap-fit, thus providing an audio (and visual) indication that flip top cap cover 920 is completely closed and secured. Again, it will be appreciated by one of ordinary skill in the art that all of the materials, manufacturing techniques, decoration techniques, etc. mentioned with respect to being applicable to the cap 914 and the cap cover apply as well to the flip-top cap cover 920.

Referring to FIG. 14A, tampon applicator package assembly 400 is modified from tampon applicator package assembly 10. Tampon applicator package assembly 400 is similar to tampon applicator package assembly 10; however, cap 414 and cap cover 452 entirely house the tampon applicator. Tampon applicator package assembly 400 has a tampon applicator (not shown), a cap 414 with a cap body 426, and a cap cover 452. Cap cover 452 has a tab 454 that can be grasped by the user. Cap cover 452 connects to cap 414, for example, by adhesive, so that the user can apply a great enough force, in a direction as shown by arrow G, to tab 454 to separate cap cover 452 from cap 414, thereby uncovering a cap opening and allowing access to the tampon applicator. Cap 414 can be integrally formed with plunger (not shown), with cap cover 452, and combinations thereof. Cap cover 452 can likewise be integrally formed with plunger (not shown).

Referring to FIG. 14B, a tampon applicator package assembly 500 is shown that is modified from tampon applicator package assembly 10. Tampon applicator package assembly 500 has a tampon applicator (not shown) and a cap 514 with a cap body 526. Tampon applicator package assembly 500 is similar to tampon applicator package assembly 10. However, cap 514 entirely houses the tampon applicator and has a cap cover 556 with perforations 560 around at least a portion of the periphery of the cap opening. Cap cover 556 has a tab 558 that can be grasped by the user. The user can apply a large enough force in a direction, as shown by arrow H, to tab 558 to separate cap cover 556 from cap 514 along perforations 560, thereby uncovering a cap opening to allow access to the tampon applicator. One skilled in the art understands tabs 454 and/or 558 can be any shape, size, in any position and/or configuration that facilitates opening, separating, removing caps 414 and/or 514, respectively, from cover 426 and/or 526, respectively. Cap 514 can be integrally formed with plunger (not shown), with cap cover 556, and combinations thereof. Cap cover 556 can likewise be integrally formed with plunger (not shown).

Referring to FIGS. 15A-15B, a tampon applicator package assembly 600 shown that is modified from tampon applicator package assembly 10. Tampon applicator package assembly 600 is similar to tampon applicator package assembly 10; however, cap 614 entirely houses the tampon applicator and has a separation 662 through cap wall 626 that extends from a top portion 620 through a bottom portion 664 to separate cap 614 into a first cap portion 666 and a second cap portion 668. Tampon applicator package assembly 600 has a tampon applicator (not shown) and a cap 614 having a cap wall 626. First cap portion 666 and second cap portion 668 are connected by hinges 670, similar to, such as, for example, an eyeglass case. Prior to use, first cap portion 666 and second cap portion 668 are connected by fasteners (not shown) and first cap portion 666 and second cap portion 668 are in a closed position as shown in FIG. 15B, to cover the tampon applicator. One skilled in the art understands fasteners (not shown) can comprise, without limitation, a latch, hook and loop, a pin, a snap, button, press-fit, snap-fit, detent, a spring-loaded hinge biasing the tampon package applicator assembly into either an open position or a closed position, or any other mechanism or material that allows attachment of two pieces to permit at least a partially open and/or closed position. Referring to FIG. 15A, first cap portion 666 and second cap portion 668 are rotated away from one another in a direction shown by arrow J (from the closed position shown in FIG. 15B to an open position as shown in FIG. 15A) to separate the fasteners and provide access to the tampon applicator. Alternatively, one of the first cap portion 666 and second cap portion 668 may be held stationary while a moment (or other rotational force or torque) is applied to the other. After the pledget is used, the tampon applicator can be placed in cap 614, and then first cap portion 666 and second cap portion 668 are rotated toward one another in the direction opposite that shown by arrow J, to cover the used tampon applicator for disposal.

Figure 16:
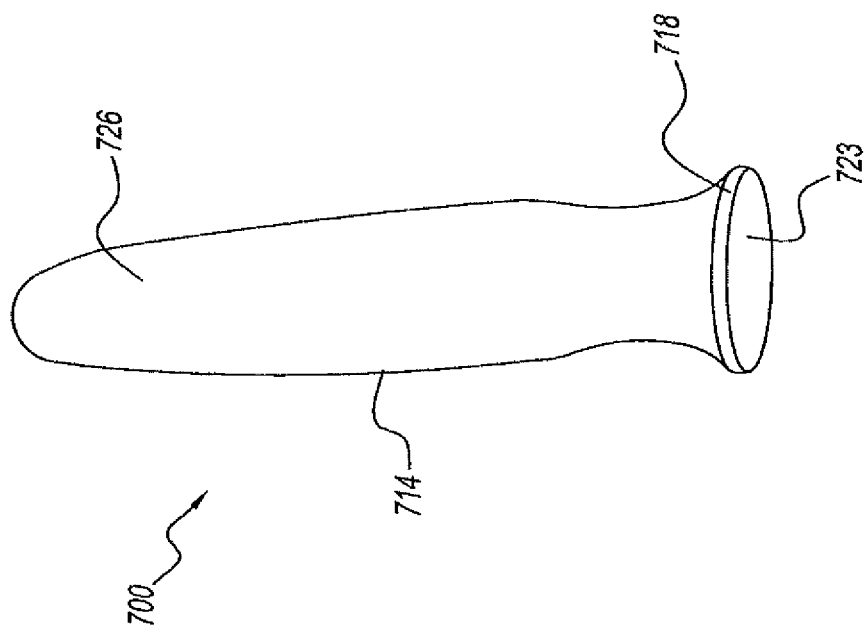
FIG. 16 is a side perspective view of another embodiment of a tampon applicator package assembly of the present disclosure with a tampon applicator having a plunger in a stored position and a cap connected to the tampon applicator.

Referring to FIG. 16, a tampon applicator package assembly 700 is shown that is modified from tampon applicator package assembly 10. Tampon applicator package assembly 700 is similar to tampon applicator package assembly 10 however; cap 714 is an elastic material that has the same shape and slightly larger size as the barrel inside tampon applicator package assembly 700. In some embodiments, tampon applicator package assembly 700 can have an illusory visual affect in order to obfuscate the tampon applicator package assembly 700. For instance, tampon applicator package assembly 700 can be holographic, or comprise any graphic, printing, texturing or pattern so that someone looking at the tampon applicator package assembly 700 would recognize an object other than a feminine hygiene device or other device used for insertion into the body. For instance, the illusory affect could lead someone looking at the tampon package assembly 700 to recognize an object of an at least partially dissimilar geometry or dimensioning. Tampon applicator package assembly 700 also has a tampon applicator (not shown in FIG. 16) disposed inside of cap 714. Cap 714 has a cap body 726. The tampon applicator has a barrel and a plunger 718 with an end portion 723. Cap 714 is placed around the barrel and the elastic material applies an inward force to maintain cap 714 on the barrel. The tampon applicator package assembly 700 of an elastic material may be manufactured to be biased in a size that permits ease of removal of the tampon applicator and/or replacement of a used product. For instance, tampon applicator package assembly 700 can comprise a hoop, ribs or any other feature positioned internally or externally that could assist in keeping the cap 714 at least partially open.

Figure 17B:
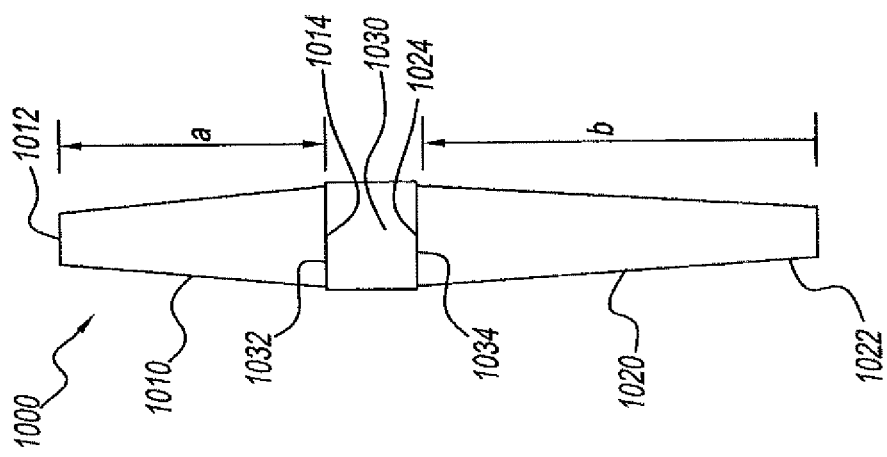
FIGS. 17A and 17B show alternative embodiments of a tampon applicator package assembly of the present disclosure.
Figure 17A:
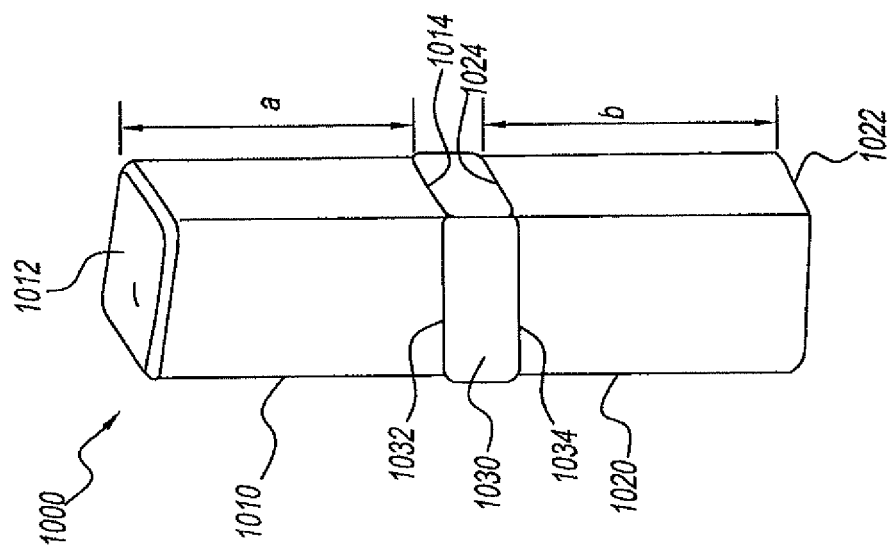

Referring to FIGS. 17A-17B, an alternative embodiment of a tampon applicator package assembly 1000 is shown. Tampon applicator package assembly 1000 is made into a container that looks like, such as, for example, a lipstick or mascara. The container has a first cap 1010 of length "a" that matingly engages with a second cap 1020 of length "b". The first cap 1010 length "a" is from about 0.1 to 5 inches, and preferably from about 0.5 to 2 inches, and second cap 1020 length "b" is from about 0.1 to 5 inches, and preferably from about 0.5 to 2 inches. The total length of first cap 1010 and second cap 1020 are from about 0.2 to 10 inches. The first cap has a closed end 1012 and an open end 1014, and likewise, the second cap has a closed end 1022 and an open end 1024. As shown throughout the present disclosure, one or both of the closed ends 1012 and 1022 can have an at least partial opening and a cap cover that at least partially, matingly engages the at least partial opening of the closed end so that at least partial seal is created. The cap lengths are chosen so that the tampon package assembly looks similar to a cosmetic object or any other object that may be found in a carrying vessel. The area where the two caps meet can be decorated with a ring 1030, or any other type of decoration, to give the impression of Personal Item in the user's carrying vessel. Ring 1030 has a first end and a second end. The first end of the ring can be adjacent an open end of the first cap 1010 or the open end of a second cap 1020, and the second end of the ring 1030 can be adjacent an open end of the second cap 1020 or the open end of the first cap 1010, respectively. When an end of ring 1030 is placed adjacent an opening of either the first cap 1010 and/or the second cap 1020, the ring and the first cap and/or second cap can matingly engage each other and form at least partial seal that encloses the tampon applicator in at least part of the first cap 1010, at least part of the second cap 1020, at least part of the ring 1030, or any combinations thereof. As with other embodiments according to the present disclosure, the attachment or closure between first cap 1010 and second cap 1020 can be via at least partial mating engagement, adhesive (whether on ring 1030 or separate from ring 1030), threads, or any combination of the foregoing. First cap 1010 and second cap 1020 can be any design or shape, such as square as shown in FIG. 17A or rectangular, and may be straight sided as shown in FIG. 17A or tapered as shown in FIG. 17B. In use, tampon applicator package assembly 1000 holds only a tampon applicator, and is used to dispose of the tampon applicator after use. Alternatively, either first cap 1010 or second cap 1020 holds the tampon applicator and the other cap has another and/or an alternative feminine hygiene product including, but not limited to, a wipe, lotion, and panty liner. Regardless of the size or placement of first cap 1010 and second cap 1020, when separated, the tampon applicator being placed in either of first cap 1010 or second cap 1020 is immediately exposed. As mentioned above, first cap 1010 or second cap 1020 may contain an alternative feminine hygiene product including, but not limited to, a wipe, lotion, and panty liner. In this configuration, the opening of the cap containing the alternative feminine hygiene product is preferably closed or sealed by, for example, a foil or other covering which, also preferably, is flexible (not shown). Such a covering may be similar to cover 452 shown in FIG. 14A or cover 556 shown in FIG. 14B.

Figure 18C:
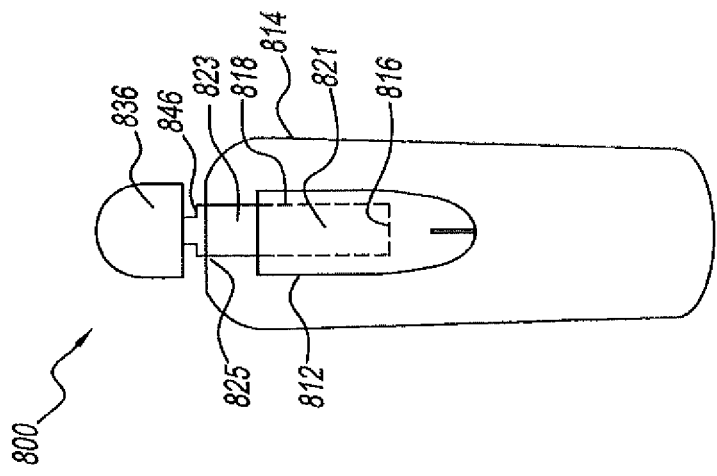
FIGS. 18A, 18B, and 18C show alternative embodiments of a tampon applicator package assembly of the present disclosure.
Figure 18B:
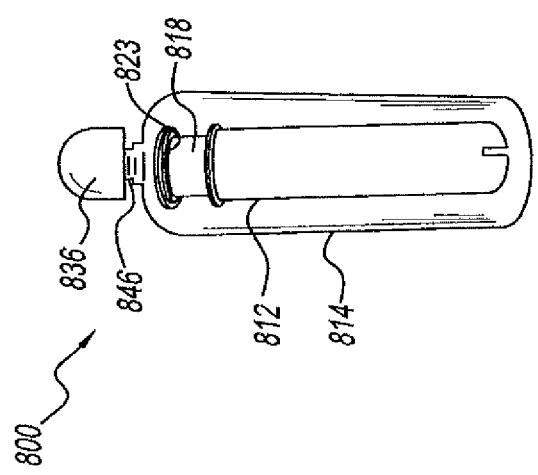
Figure 18A:
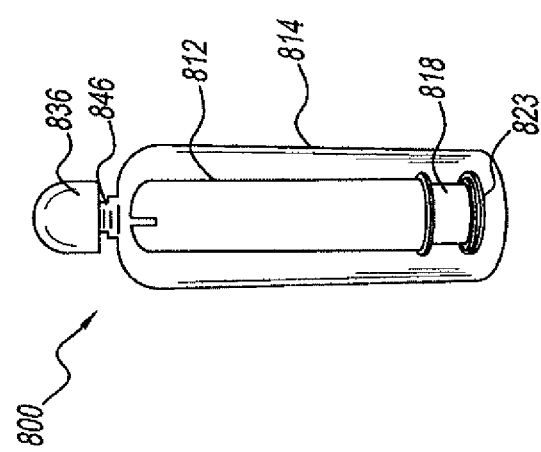

FIGS. 18A, 18B and 18C show additional embodiments of the tampon applicator package assembly 800. Tampon applicator package assembly 800 has a cap 814 and a cap cover 836. Cap 814 is sized, shaped and made from a material that would provide the appearance of, such as, for example, a food or liquid pouch. Tampon applicator 812 has a barrel 816 and a plunger 818 and can be oriented in any fashion in cap 814. In some embodiments, more than one tampon applicator 812 or other feminine hygiene devices can be contained in cap 814. In some embodiments, cap 814 can have a perforation or other means of facilitating opening of the cap 814. Plunger 818 has a telescoping portion 821 and an end portion 823. As shown in FIG. 18C, end portion 823 can be at least partially, matingly engage cap cover 836 so that when the user removes cap cover 836, the end portion 823 is accessible and ready for withdrawal from cap 814. Cap 814 can have Structures 825 that facilitate removing tampon applicator 812 completely from the pouch in a single action by the user as described herein in paras. [0061] and

[0062]. Cap cover 836 can have a cap cover protrusion 846 that at least partially engages end portion 823 and/or partially engages cap 814 so that tampon applicator package assembly 800 is sealed. Cap cover 836 can be integrally formed with cap 814 and/or end portion 823.

Figure 19:
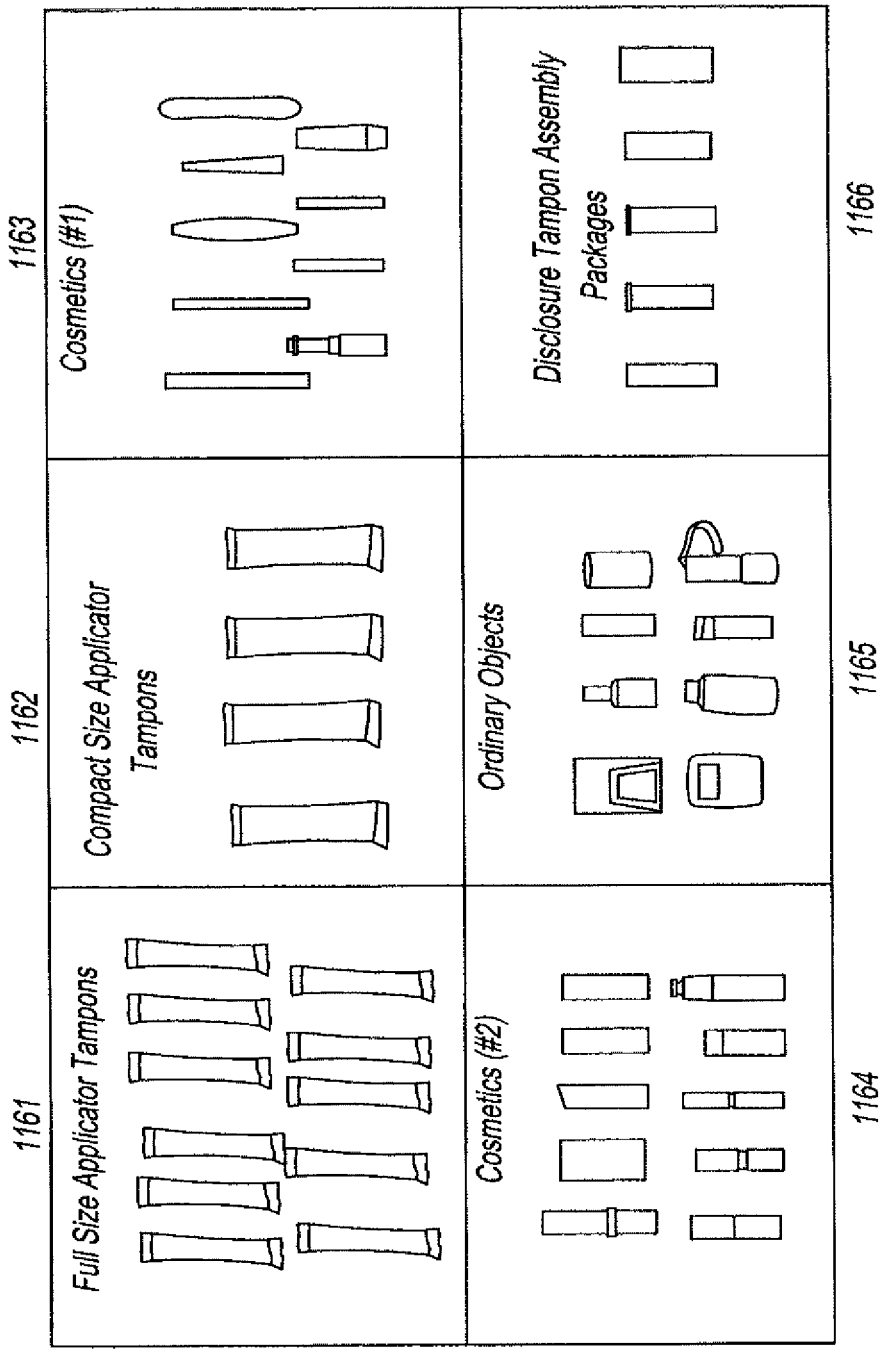
FIG. 19 shows photos of articles used for a consumer recognition survey for tampon packaging assemblies of the present disclosure.

FIG. 19 shows a series of products that were used for an online consumer recognition survey that will be discussed below. Full size applicator tampons 1161 show prior art regular tampon applicators. Compact size tampon applicators 1162 show prior art compact tampon applicators. Cosmetics (#1) 1163 shows prior art cosmetics such as, but not limited to, mascara. Cosmetics (#2) 1164 shows prior art cosmetics such as, but not limited to, nail polish. Ordinary Objects 1165 shows ordinary objects that might be found in a carrying vessel such as, but not limited to, a garage door opener, an umbrella, a flashlight, or a lighter. Disclosure Tampon Assembly Packages 1166 shows embodiments of the present disclosure's tampon applicator package assembly.

It will be appreciated by those of ordinary skill in the art that tampon applicator package assembly 10 may be provided with two cap covers, each independently sealing an open end of a cap. In embodiments, including but not limited to, with two caps and/or two covers, with two caps and one cover, with one cap and two covers, the caps and cap covers can be of any type as described in the present disclosure, and any combinations thereof. In this embodiment, the cap will be provided with two open ends, one disposed proximal to the plunger end of the tampon applicator ("bottom end") and one disposed proximal the pledget-containing end of the barrel ("top end"). A cap can have any of the cap and cap cover configurations hereinbefore described, such as a peelable cap cover or perforated cap cover at each open end of the cap, can have a flip top cap cover at each open end of the cap, or can have an at least partial mating engagement between cap and one or more of the cap covers at each open end of the cap. Of course, where the cap is provided with two open ends, each open end can be provided with another cap and/or cap cover. This configuration of tampon applicator package assembly 10 has a benefit of ease of manufacture. In this regard, the barrel can be inserted into the cap via the "top" opening, and the plunger/pledget combination can be inserted into the cap via the "bottom" opening. This "two" insertion assembly provides for easier insertion of the barrel because, in this instance, the barrel does not need to be pushed past any Structure (if present) disposed on the inner surface of the cap. Although not preferred, it is also possible to insert the complete tampon applicator including the barrel, the plunger and the pledget into the cap through the "top" opening.

Currently available tampon applicator wrappers tear easily during transportation. The present disclosure resolves this problem by eliminating the wrapper and replacing it with a cap and/or cap cover, including, but not limited to, caps 14, 114, 214, 314, 414, 514, 614, 914, 1010, and 1020. The cap includes but is not limited to, caps 14, 114, 214, 314, 414, 514, 614, 914, 1010, and 1020, is made from a material that has greater durability. For example, the cap of the present disclosure is fashioned so that it avoids puncturing, tearing and/or other damaging that renders the contents of the tampon applicator package assembly vulnerable to contamination and/or destruction. For purposes of the following paragraph, all caps will be referred to as cap 14. To evaluate the ruggedness or toughness of the tampon applicator package assemblies of the present disclosure, a variety of the assemblies were exposed to a "purse test". The purse test comprised placing a sampling of the tampon applicator package assemblies into a ladies purse along with other commonly-carried items including, but not limited to, one or more keys, sunglasses, wallet, pen, pencil, nail clipper, phone charger, cell phone, iPod®, coin, nail polish and mascara. The purses were then shaken in a Lab Line Orbital Environ Shaker for sixty (60) minutes at three hundred and twenty (320) rpm. At the conclusion of the purse test, six (6) of the nine (9) tampon applicator package assemblies had not damage at all, one (1) had a slight scratch on its bottom surface, and two (2) had minor hairline-like cracks in the cap. All of the adhesive layers were intact. Thus, the tampon applicator assembly package remained substantially intact after this test. Further, the purse test demonstrates that the tampon package applicator assembly does not tear and/or puncture and thus prevents the contents of the tampon package applicator assembly from becoming vulnerable to contamination and/or damage.

In sum, it has been found that another advantage of present tampon applicator package assemblies is that disposal of used tampon applicators is sanitary and discrete. For purposes of this paragraph, all embodiments of the disclosed tampon applicator assemblies will be referred to as tampon applicator package assembly 10. Traditional wrappers need to be torn to remove the applicator therefrom. It is usually difficult, if not impossible, to place the used tampon applicator back into the torn wrapper. In the present disclosure, cap 14 is one resilient piece, and it is very easy to place a used tampon applicator back in cap 14. Once discarded, only cap 14 can be seen, and cap 14 does not resemble a used tampon applicator. Furthermore, the soiled or discarded feminine hygiene product(s) is contained in cap 14, which enables a more hygienic disposal, thereby diminishing and/or preventing the opportunity for the used applicator or other soiled discarded feminine hygiene item from coming into contact with anything other object aside from cap 14. Also, tampon applicator package assembly 10 enables a design that prevents overall apprehension or embarrassment of the user that can result from the use of tampons. Thus, the small, discrete design ensures an embarrassment- or apprehension-free usage experience. Tampon applicator package assembly 10 resembles any Personal Item that the user might carry and, thus, enables a worry-free carrying, and/or use, and/or disposal experience, and combinations thereof. Also, the variability of shapes and designs for cap 14 enables a new, fun way to use tampons.

All embodiments of the tampon applicator package assembly referred to and described above can be sized and designed to fit a full-size tampon applicator and/or a compact tampon applicator, and/or other complementary products, or any combinations thereof.

Since one drawback sought to be overcome by the present disclosure is the visible appearance of present tampon assembly packages, a study was undertaken to ascertain the "discreteness" of the tampon applicator package assembly of the present disclosure versus other tampon packaging and common items present in a purse or pocketbook of a tampon user. The results of the recognition study are set forth below.

Tampon Discretion Survey

The study was undertaken to assess the recognizable features of applicator tampons in order to develop a disguising index. An internet-based survey evaluation was conducted among applicator tampon users, ages 13-49.

Test Method: Respondents were asked to participate in an internet-based survey questionnaire regarding their experiences in using tampons. Respondents were first screened according to the inclusion criteria then asked to answer questions regarding their perceptions of tampon usage and appearance. The survey took approximately 30 minutes to complete.

Respondent Inclusion Criteria: The following criteria were used for inclusion in the survey: (1) Gender—Females; (2) Number of participants N=300; (3) Age range—13-49 (25% 13-17; 25% 18-24; 25% 25-34; 25% 35-49); (4) Menstruates regularly; (5) Uses tampons as her main menstrual protection method; (6) Uses applicator tampons most often; and (7) Has used compact applicator tampons in the past 6 months.

Key Findings: Total Respondents: The results from the study show that among total respondents, both full-sized and compact-sized applicator tampons have recognizable features that are identifiable as tampon products. Both the full sized and compact sized tampon products achieved a 94% or greater percentage rating for "agreement" of resemblance to tampons by the respondents. The study also showed that the tampon package assemblies of the present disclosure are less identifiable as tampon products. The tampon applicator assembly packages according to the present disclosure achieved a "disagreement" for resemblance to tampons of 69% of the respondents. For reference, both the Cosmetic and Ordinary object images evaluated show high "disagreement" for resemblance to tampons of 89% or greater of the respondents. The Table below sets forth the actual percentages that were observed in the survey. The photo images used in the survey are set forth in FIG. 18.

SUMMARY TABLE

| "The products in the photo resemble tampons . . ." | | |
| --- | --- | --- |
|  | (Agree completely/ Somewhat | (Disagree completely/ Somewhat) |
| Full Size Applicator Image | 99 | 1 |
| Compact Size Applicator Image | 94 | 4 |
| Cosmetics Image #1 | 7 | 89 |
| Cosmetics Image #2 | 7 | 90 |
| Ordinary Objects | 1 | 97 |
| Disclosure Assemblies | 17 | 69 |

The measure of "discreteness" can also be quantified by weighting the responses and normalizing the weighted results. The first step is to assign a "weight" to each survey answer option with a number from 1 to 5. Thus, "agree completely" was weighted 5; "agree somewhat" was weighted 4; "neither agree nor disagree" was weighted 3; "disagree somewhat" was weighted 2; and "disagree completely" was weighted 1. At either end of the spectrum of weighted results, if an object is completely NOT-DISCRETE, then 100% of the respondents should answer "agree completely". To obtain a weighted index, there is then a normalization by the total population 100%=(100%×5)/(100%)=5; and if an object is completely DISCRETE, then 100% of the people should answer "disagree completely". To obtain a weighted index, there is then likewise a normalization by the total population 100%=(100%×1)/(100%)=1. Thus, the discretion index of a completely NOT-DISCRETE object is 5, while the discretion index of a completely DISCRETE object is 1.

Using the series of products that were used for an online consumer recognition survey and shown in FIG. 18, each object was determined to have the following Discretion Index value.

| Object in FIG. 18 | Discretion index |
|---|---|
| Full size applicator tampons | 4.93 |
| Compact size applicator tampons | 4.6 |
| Cosmetics #1 | 1.4 |
| Cosmetics #2 | 1.3 |
| Ordinary Objects | 1.12 |
| Disclosure Tampon Assembly Packages | 1.62 |

As can be seen, the tampon applicator assembly packages according to the present disclosure had a Discretion Index below 2, and on the order of cosmetics and ordinary objects found in a carrying vessel. Stated another way, the tampon applicator assembly packages according to the present disclosure had a Discretion Index of approximately one-third as great as compared to that of either full-size or compact applicator tampon applicator packages. Therefore, the tampon applicator assembly packages according to the present disclosure have a Discretion Index no greater than about 3, preferably no greater than about 2, more preferably no greater than about 1.5, and most preferably less than about 1.5.

As described above, a tampon applicator package assembly may be designed and manufactured to provide for a degree of discretion. Furthermore, a case associated with the tampon applicator package assembly may be strong, rigid, and durable. Such a feature may be contrasted with wrappers that may be subjected to wear over time.

Flexural rigidity can be defined as the resistance offered by an object while undergoing bending. Flexural rigidity, D, for a thin film/plate can be calculated as:

$$D = \frac{EI}{1-\mu^2} = \frac{Ebt^3}{12(1-\mu^2)}$$

where E is Young's modulus, I is second moment of inertia and $\mu$ is Poisson's ratio. Second moment of inertia, I, for a thin film may be calculated as:

$$I_{thin\,film} = bt^3$$

where b is the width of the film and t is the thickness of the film.

Conventional tampon wrappers may be made from similar materials (e.g., simple elastomeric polymers such as olefins). The Poisson's ratio, $\mu$, for these materials are similar and thus don't make an appreciable difference in the calculation of flexural rigidity, D.

The table below summarizes EI values, which represent a measure of the flexural rigidity for given geometries/configurations, for a sampling of existing tampon wrappers (regular absorbency only), as identified by wrapper names in use:

| Wrapper Name | width (mm) | thickness (mm) | I (mm⁴) | E (MPa) | EI (Nmm²) |
|---|---|---|---|---|---|
| Sport | 30.163 | 0.076 | 1.33E−02 | 22.3 | 0.298 |
| GG | 26.988 | 0.025 | 4.42E−04 | 67.8 | 0.030 |
| Pearl | 36.513 | 0.089 | 2.57E−02 | 14.8 | 0.380 |
| Radiant | 44.450 | 0.178 | 2.50E−01 | 26 | 6.496 |
| Sleek | 41.275 | 0.058 | 8.23E−03 | 16.3 | 0.134 |

Tampon applicator package assemblies in accordance with this disclosure replace a conventional wrapper with a cap (e.g., cap 14 in FIG. 1A). The flexural rigidity of this cap can be calculated from the flexural rigidity formulation for a hollow cylinder:

$$EI = E\pi \frac{(r_o^4 - r_i^4)}{4}$$

where $r_o$ is the outer radius and $r_i$ is the inner radius of the hollow cylinder. The EI values for some tampon applicator package assemblies in accordance with this disclosure are calculated and given in the table below for given assembly types:

| Assembly style | $r_o$ (mm) | $r_i$ (mm) | I (mm⁴) | E (MPa) | EI (Nmm²) |
|---|---|---|---|---|---|
| Flip top | 10.5 | 8.75 | 4.94E+03 | 187.6 | 9.27E+05 |
| Twist-off | 10.5 | 9.325 | 3.61E+03 | 187.6 | 6.77E+05 |

The values provided in the tables are illustrative. In some embodiments, EI values greater than or equal to $6.7 \times 10^5$ Nmm² or $9.2 \times 10^5$ Nmm² may be used.

The EI values for the case can be above 10 Nmm². For example, values above $1 \times 10$ Nmm² and above $1 \times 10^4$ Nmm² may be used in some embodiments.

As described herein, a personal care product (e.g., pledget 13 shown in FIG. 2) accommodated by one or more tampon applicator package assemblies may include a string (e.g., string 13A of FIG. 3D). Management of the string can prove challenging. For example, during assembly, the string must be pulled-through the plunger to ensure it is readily accessible for the consumer when the tampon applicator package assembly is opened and being prepared for deployment. For example, it may be necessary to keep the string from becoming tangled in order to promote efficiency or effectiveness in the deployment of the personal care product.

Figures 20A, 20B:
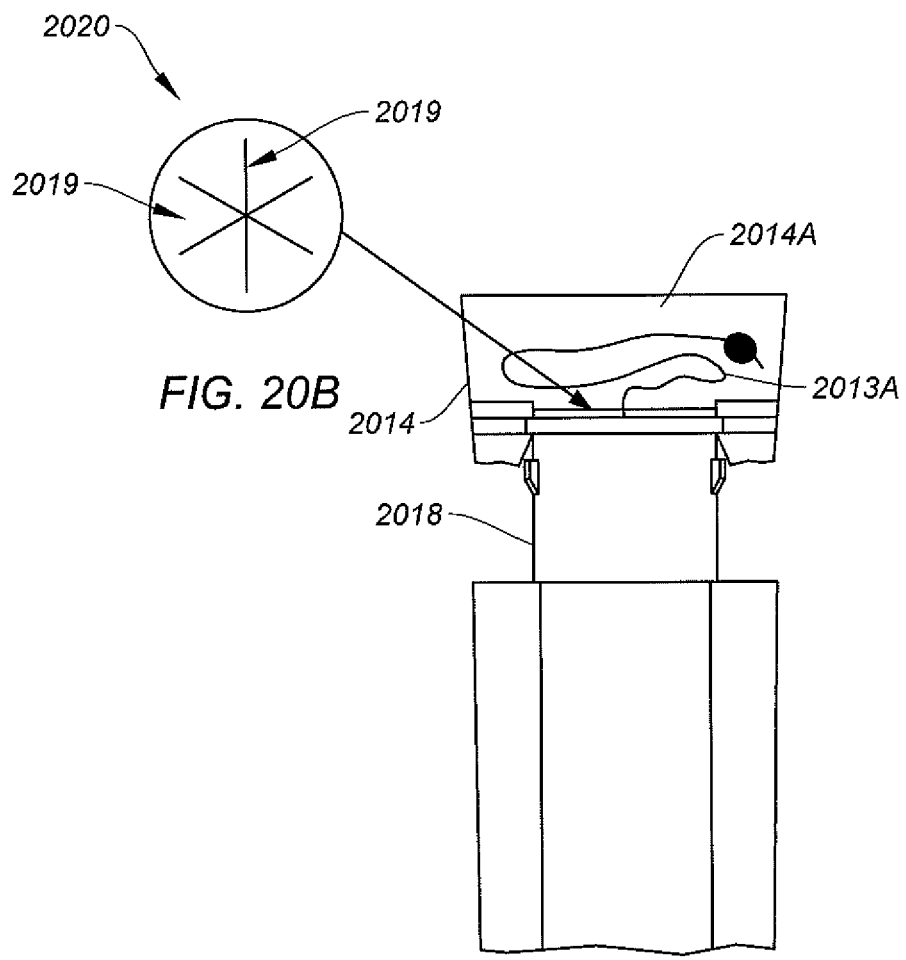
FIGS. 20A-20O illustrate various vies of tampon applicator package assemblies and components incorporating a slit-surface.
Figures 20C, 20D, 20E:
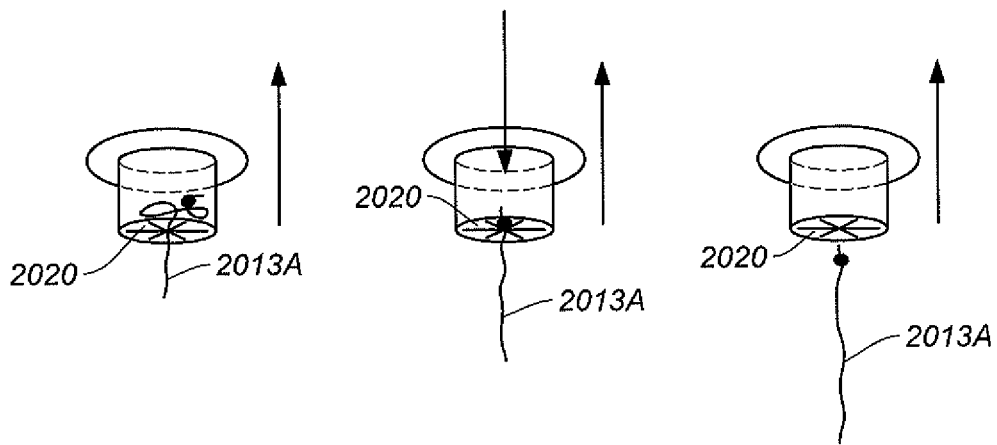
Figure 20F:
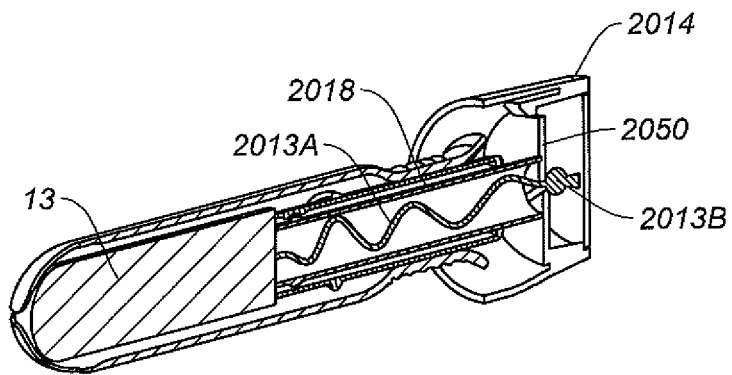
Figure 20G:
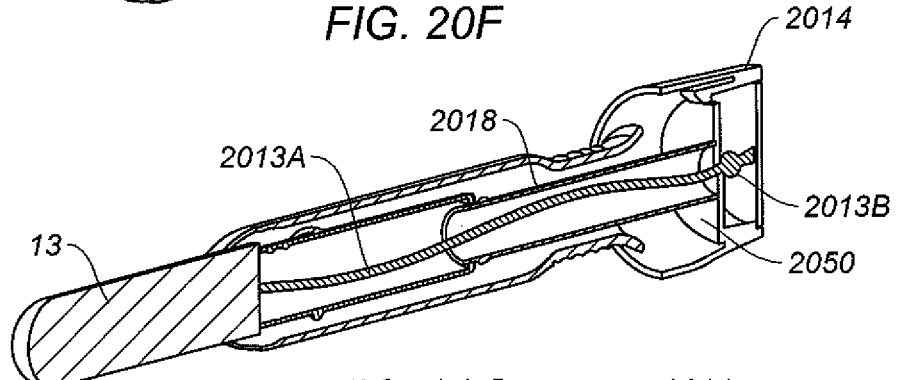
Figure 20H:
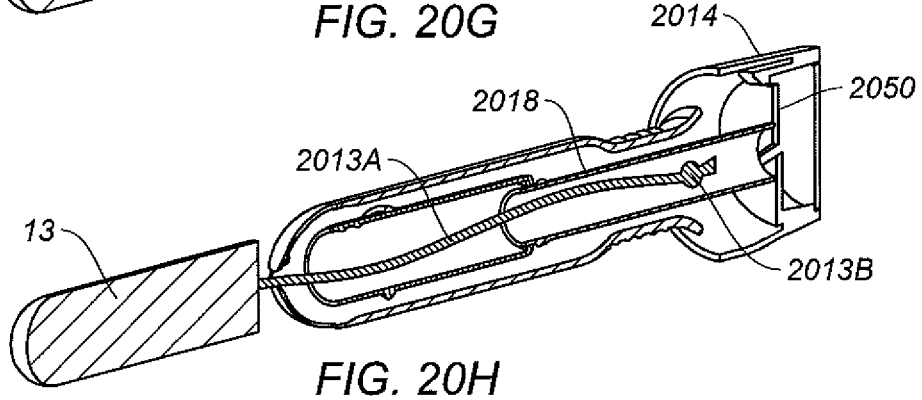
Figure 20I:
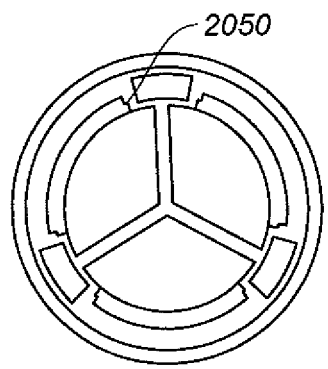
Figure 20J:
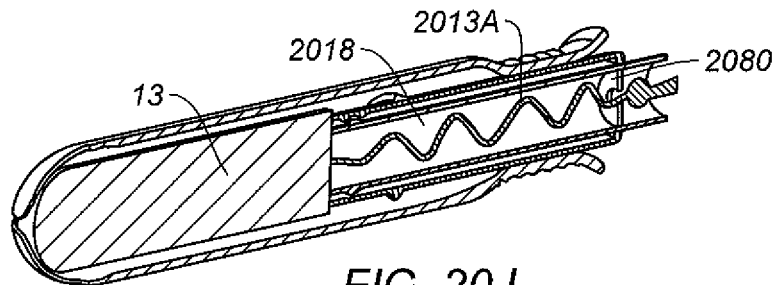
Figure 20K:
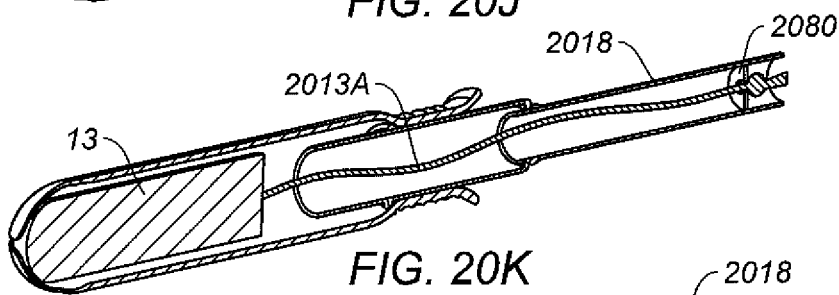
Figure 20L:
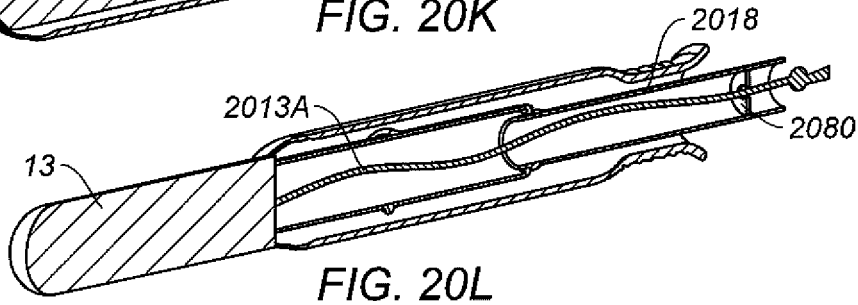
Figure 20M:
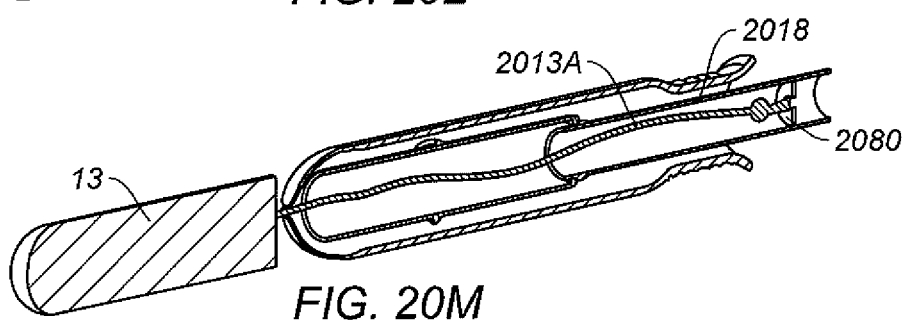

Referring to FIG. 20A, a cap 2014 (which may correspond to the cap 14) can be snapped onto an end portion of a plunger 2018 (which may correspond to the plunger 18) with friction fit, threads or any other technique of engagement. The cap 2014 may be made from one or more plastics; e.g., polyethylene, polypropylene, polybutylene, polystyrene, polyvinylchloride, polyacrylate, polymethacrylate, polyacrylonitrile, polyacrylamide, polyamide, nylon, polyimide, polyester, polycarbonate, polylactic acid, polyhydroxyalkanonate, ethylene vinyl acetate, polyurethane, silicone, thermoplastic starch, trans-polyisoprene, derivative thereof, copolymers thereof, mixtures thereof or any other suitable plastic material. Alternatively, the cap 2014 can be made from a non-polymer material such as paper, paperboard, cardboard, cellulosed (such as molded cellulose), metal, textile, wood or any combination thereof. Cap 2014 can have different coatings applied to it for ease of opening and decorating purposes. The material of cap 2014 can be biodegradable, compostable or flushable. The cap 2014 can be made using various manufacturing techniques including, but not limited to, injection molding, extrusion, blow forming, thermoforming, injection blow molding, rotational molding, transfer molding, comolding, overmolding, casting, calendaring, coating, compression molding, extrusion molding, laminating, pultrusion, slush molding, transfer molding, contact molding, metal forming processes and dipping and a combination thereof.

Figures 20N, 20O:
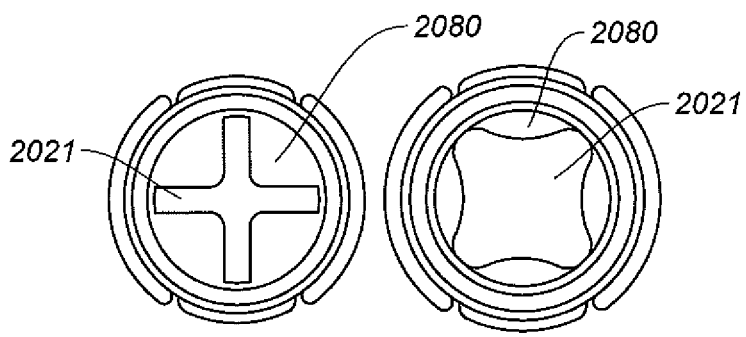

The cross-sectional shape of the cap 2014 can be circular, rectangular, triangle, star-shaped, flower-shaped or a combination thereof. The cap 2014 can have a built-in "slit-surface" structure 2020 having flaps 2017 separated by slits 2019. In some embodiments, structure 2020 resembles the top of a disposable coffee cup lid. Cap 2014 has a reservoir 2014A above structure 2020 to store a string 2013A when the tampon applicator package assembly is not in use. As shown in, for example, FIGS. 20O-20P, the string 2013A unwraps through a hole 2021 in the slit-surface 2020.

Referring to FIGS. 20F-20I, the slit-surface can be a separate part 2050 that can be snapped or attached to the cap 2014 in any way (ultrasonic bonding, hinge, etc.). Yet another embodiment includes a slit-surface 2080 built into the plunger 2018 as shown in FIGS. 20J-P. The location of the slit-surface 2080 can be anywhere along the length of the plunger 2018.

A slit-surface (e.g., slit-surfaces 2020, 2050, or 2080) preferably include one to ten flaps, and in some embodiments, two to five flaps. The flaps may be thin and/or flexible such that when the string 2013A goes through the hole 2021 in the middle of the slit-surface or through the slit 2017 between the flaps 2019, they bend and give way to the string 2013A. The size of the hole 2021 in the middle may be 1% to 150% of the string 2013A knot 2013B size; in some embodiments between 20% and 70%. There might be a gap between the flaps. The gap distance between the flaps may be 1% to 150% of the string 2013A knot 2013B size; in some embodiments between 20% and 70%.

In some embodiments, the cap 2014 has a hole 2021 (see FIGS. 20O-20P) to enable the string 2013A to be sucked through the plunger 2018 during assembly. The size of the hole 2021 may be between 1% and 99% of the cap 2014 diameter, in some embodiments between 20% and 80% of the cap 2014 diameter.

Figure 21A:
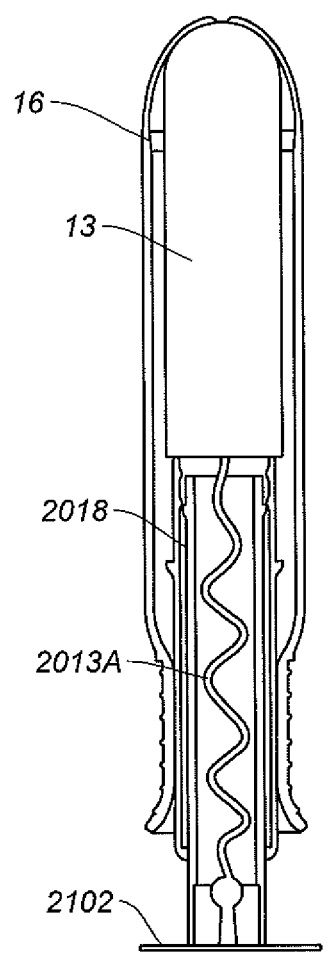
FIG. 21A-21B illustrates a tampon applicator package assemblies including a mechanism for retaining a string.
Figure 21B:
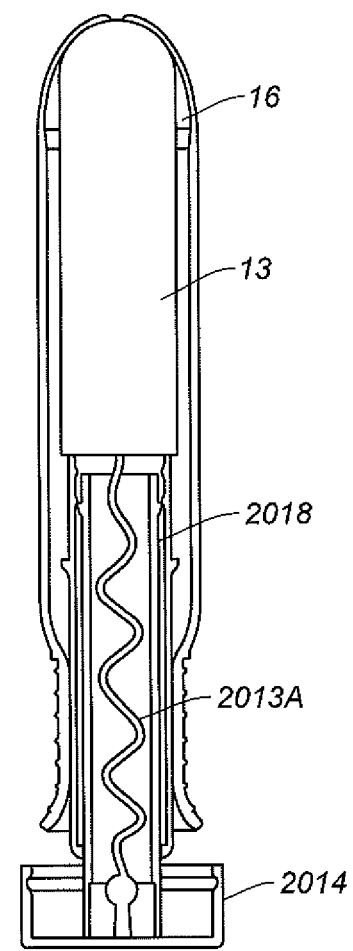

As the string 2013A is sucked through the plunger 2018, the string 2013A still needs to be enclosed within the plunger 2018 (e.g., the string 2013A may be precluded from dangling out of the plunger 2018 in some embodiments) since the cap 2014 may need to be attached to an end of the plunger 2018. FIGS. 21A-21B show an embodiment of how this can be accomplished. As the string 2013A is pulled through the plunger 2018 by a vacuum, a mechanism 2102 that would allow the vacuum/air to pass through but not the string 2013A can be placed at the end of plunger 2018. This mechanism 2102 can include a screen, sieve or any other technique that has or provides a certain pore diameter. The string 2013A can alternatively be sucked through using electrical charge/electrostatic forces such that the string 2013A can be pulled through the plunger 2018 but stopped before the string 2013A goes out of or exits the plunger 2018. This string assembly method can be applied to any of the embodiments described in this disclosure, particularly those that may require keeping the string 2013A enclosed in the plunger 2018 after the pledget 13 is inserted into the barrel 16. If the cap 2014 doesn't have a hole, the string 2013A is first sucked in then followed by the cap 2014 being snapped at an end of the plunger 2018. If the cap 2014 does have a hole 2021, then the cap 2014 can be snapped onto an end of the plunger 2018 first, then the string 2013A is sucked through the plunger 2018. Once the tampon applicator package assembly is assembled and the string 2013A is stored in the reservoir 2014A (see FIG. 20A), the hole 2021 can be covered with a label (e.g., such as sticky tab 31 in FIGS. 3C-3D) to prevent the string 2013A getting out. Alternatively, a separate piece of material can be attached to close the hole by using friction fit, threads, ultrasonic bonding, adhesives and any other joining methods available. During use, as the pledget 13 is ejected into the user's body, the string 2013A goes through the slit-surface (e.g., slit-surface 2020, 2050, or 2080) which helps the string 2013A unwrap and come out in a generally linear and/or tangle-free manner.

In some embodiments, the string 2013A can be sucked through the top (e.g., through the petals at the open end of the barrel 16) by a vacuum as shown via reference character 2202 in FIG. 22. The string 2013A would then be located substantially under the pledget 13. The cap 2014 can then be attached to an end of the plunger 2018. Alternatively, the plunger 2018 and the cap 2014 can be manufactured together such that they are one piece. The cap 2014 can have a hole or several holes to allow for a vacuum to be applied. Once the cap 2014 is attached to the plunger 2018, the string 2013A can be sucked through the plunger 2018 such that the string 2013A doesn't bunch up at the bottom of the pledget 13. The application of a vacuum to the cap is reflected in FIG. 22 via reference character 2204.

Figure 23:
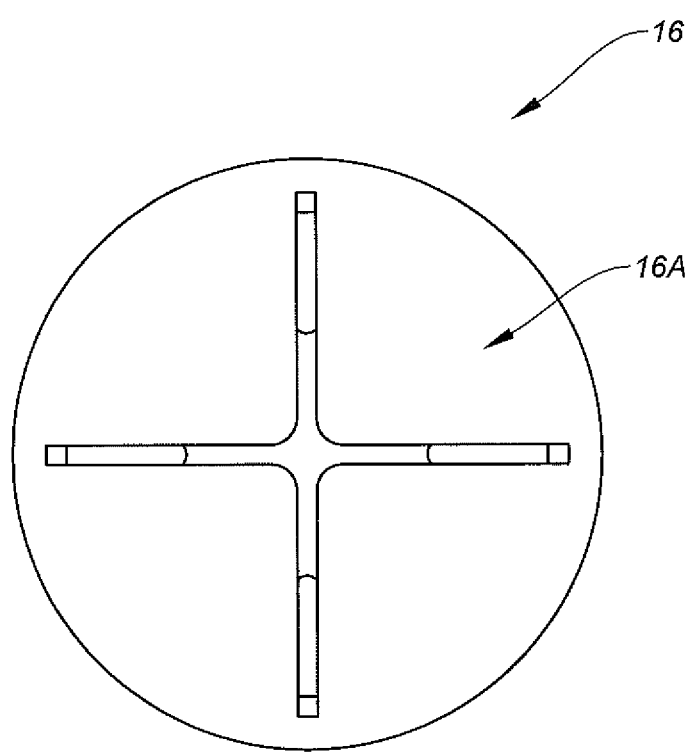
FIG. 23 illustrates a portion of a barrel including petals.

An embodiment of a portion of a barrel 16 is shown in FIG. 23. The petals 16A of the applicator can act like a slit-surface (e.g., slit-surfaces 2020, 2050, or 2080) as described above. As the pledget 13 is inserted and ejected into the user's body, the string 2013A will go through the petals 16A and unwrap as the string 2013A goes through. The petals 16A may be thin and/or flexible such that when the string 2013A goes through the hole 2021 in the middle or through the gap between the petals 16A, the petals 16A bend and give way to the string 2013A. The gap distance between the petals can be 1% to 150% of the string 2013A knot 2013B size; in some embodiments between 20% and 70%.

Figures 24A, 24B:
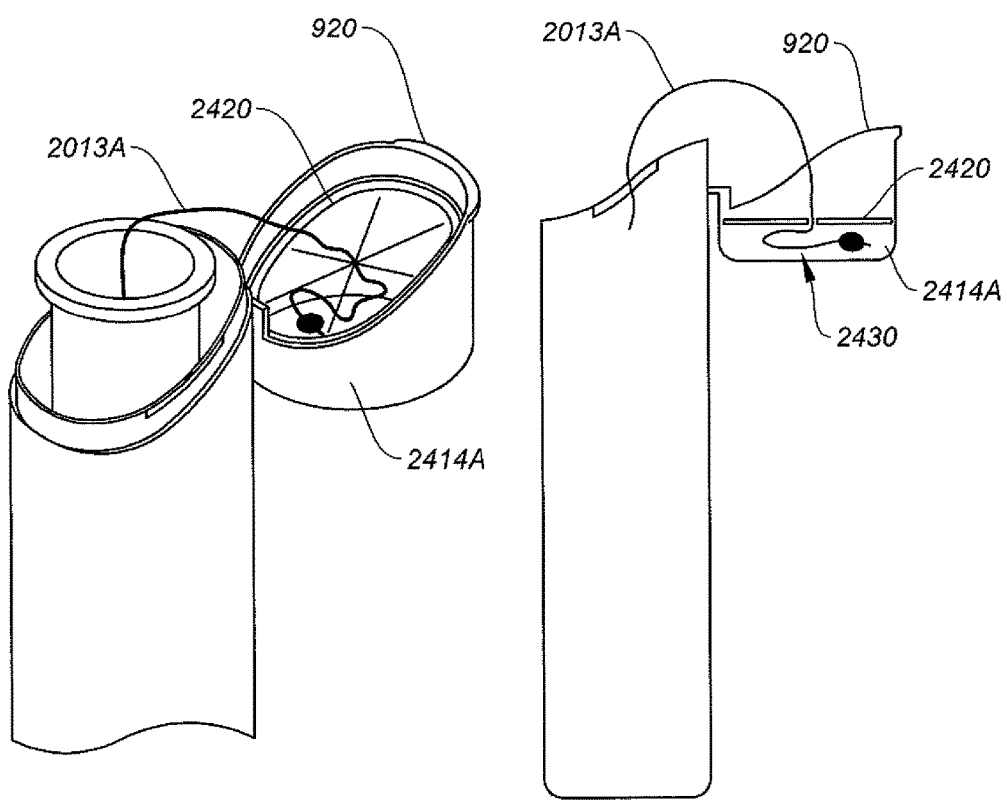
FIGS. 24A-B illustrate a tampon applicator package assemblies including a flip top cover configured to accommodate a slit-surface structure and a string reservoir.
Figure 25A:
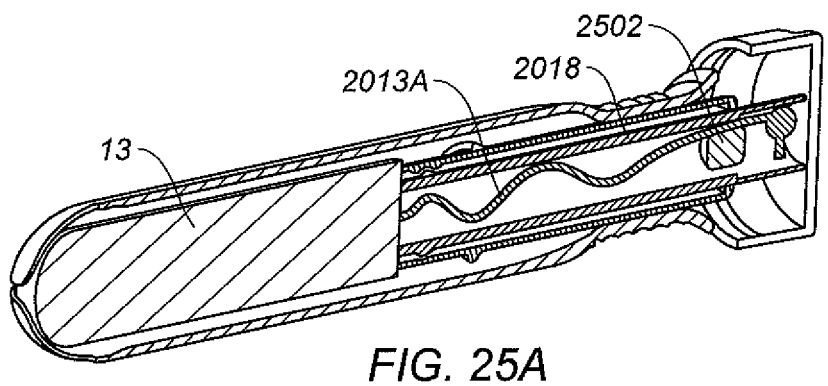
FIGS. 25A-D illustrate a tampon applicator package assemblies that include an obstruction for managing a string.
Figure 25B:
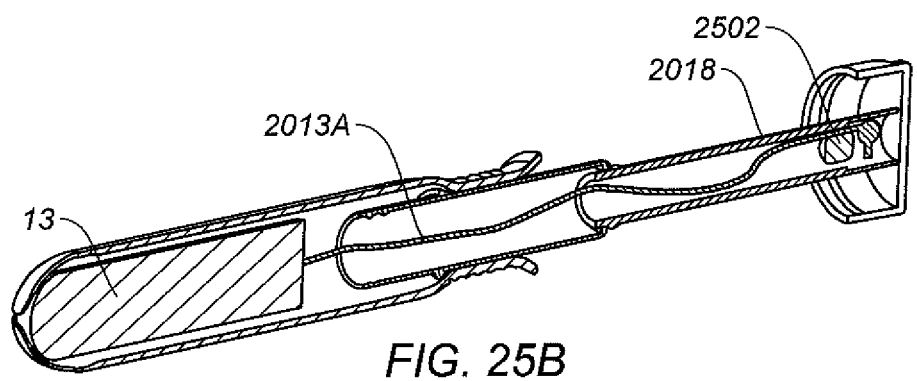
Figure 25C:
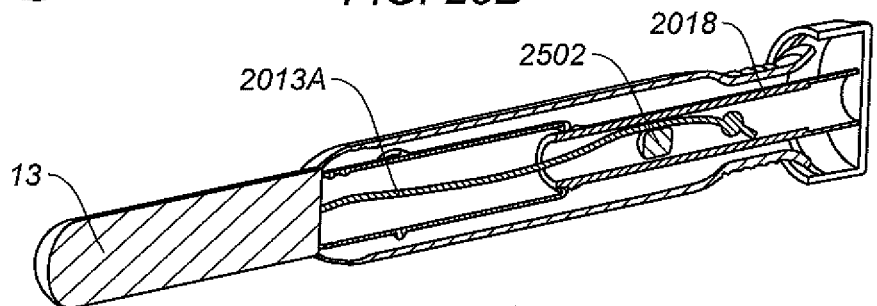
Figure 25D:
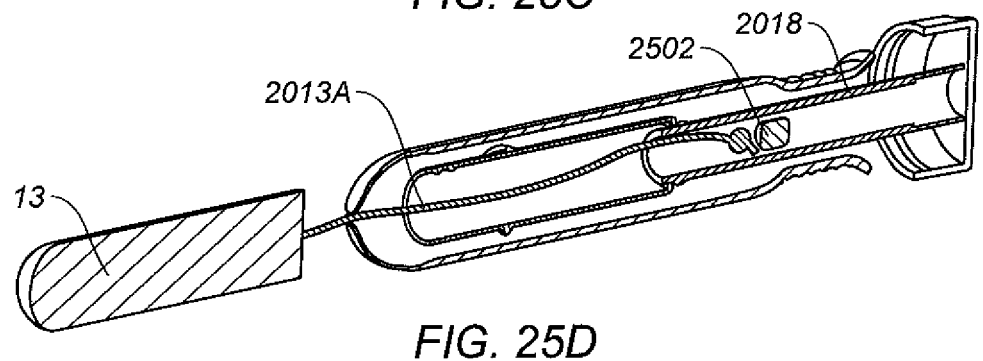
Figure 27A:
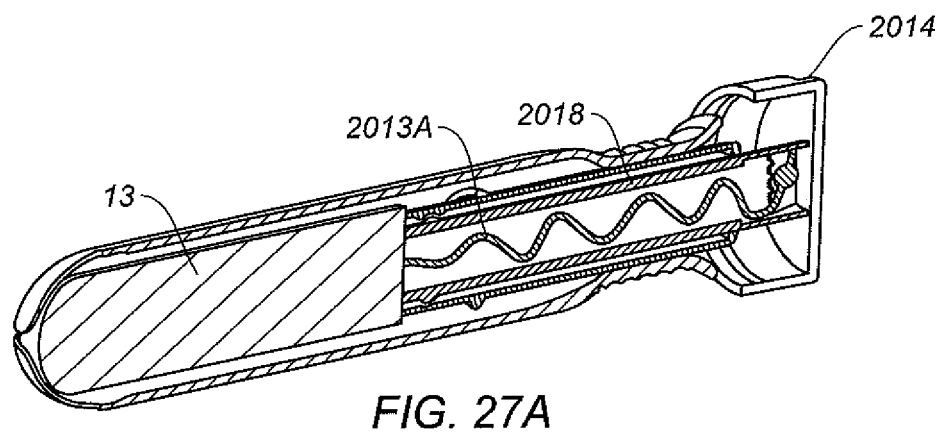
FIGS. 27A-D illustrate a tampon applicator package assemblies that include an a sticky tab for managing a string.
Figure 27B:
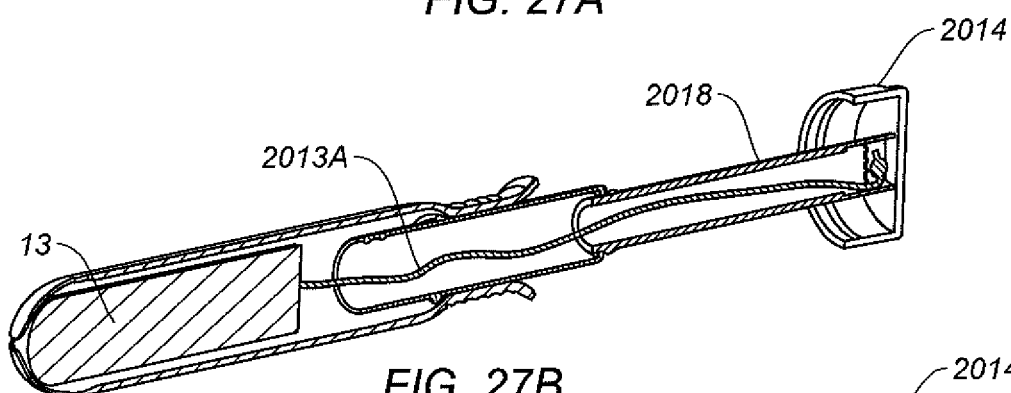
Figure 27C:
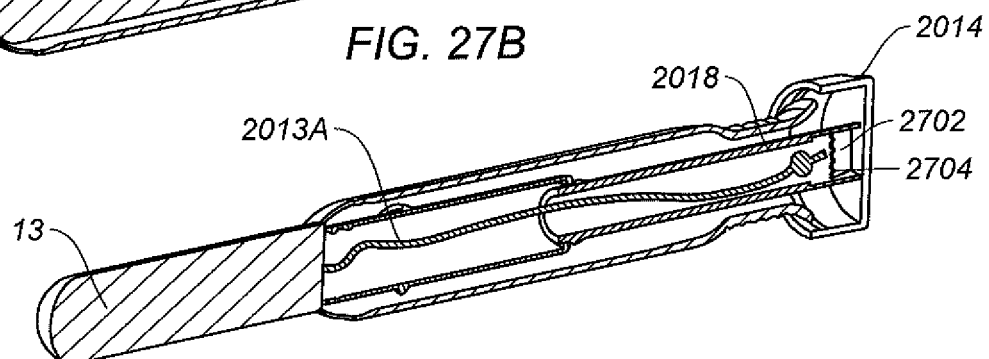
Figure 27D:
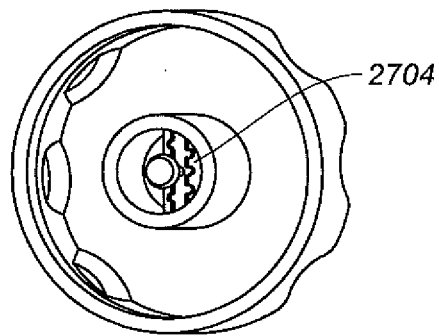
Figure 28A:
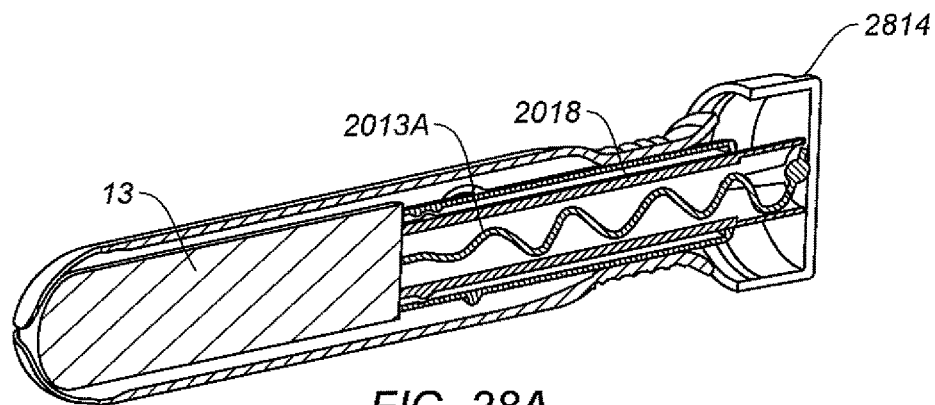
FIGS. 28A-D illustrate a tampon applicator package assemblies that include tabs for managing a string.
Figure 28B:
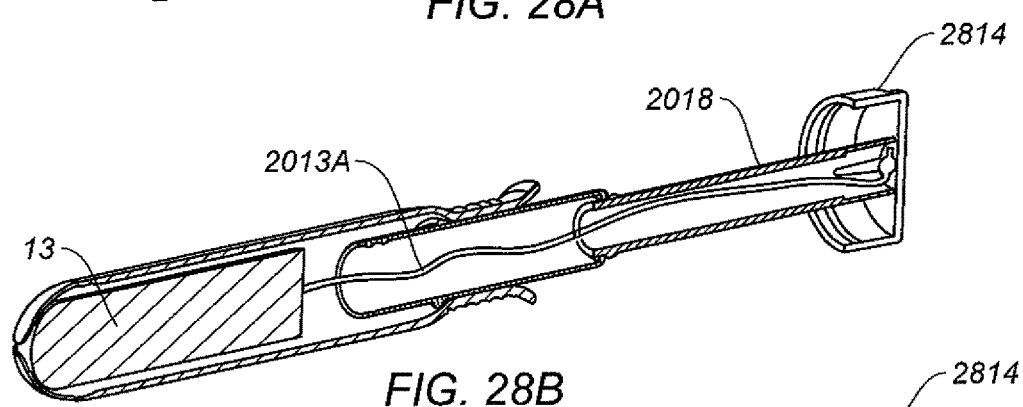
Figure 28C:
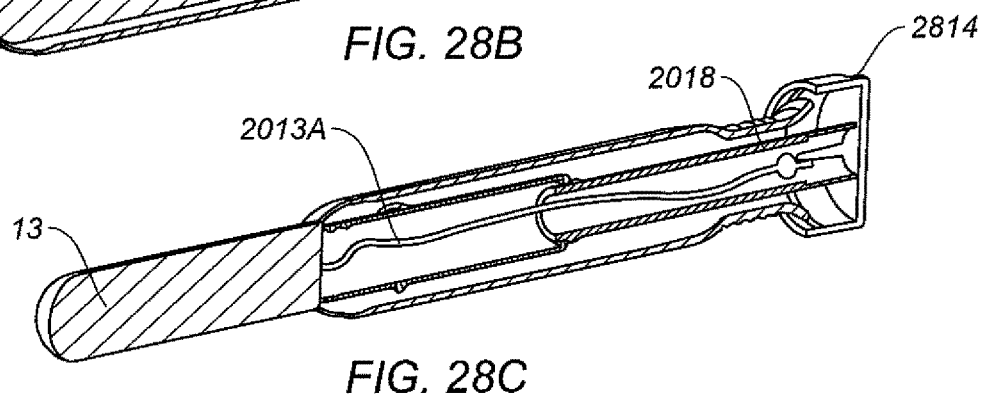
Figure 28D:
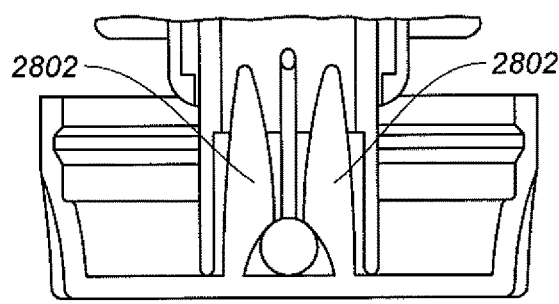

Referring to FIGS. 24A-B, a slit-surface structure 2420 and a string reservoir 2414A can be built into a flip top cover 920 as described above in connection with, e.g., FIGS. 13A-13B. Similar to above, the string goes through the hole in the middle of the slit surface. There might be a hole 2430 on the flip top cap 920 to enable the string 2013A to be sucked through the slit-surface 2420 during assembly so the string 2013A can be stored in the reservoir 2414A. Similarly, once the package is assembled and the string 2013A is stored in the reservoir 2414A, the hole 2430 can be covered with a label or a separate piece of material to prevent the string 2013A getting out. In this flap top embodiment, the string 2013A can be stored in other ways that don't require a slit-surface 2420 and reservoir 2414A. For example, the string 2013A can be wrapped around at lease a portion of plunger 18 at the end portion 23 (FIG. 1A) of the plunger 18. Alternatively, the string 2013A can be tucked in the flip top cap cover 920 (FIG. 13A) and stored until use. When the user opens the flip top cap 920, the string 2013A may be visible and readily available for the user. Yet another alternative is to lay the string 2013A along the length of the assembly, similar to how the string 2013A may be stored in conventional compact applicator tampon wrappers. As the user pulls the assembly out of the flip top cap 920, the string may come out alongside at least a portion of the tampon applicator.

Referring to FIGS. 25A-D, an "obstruction" 2502 (an object that would guide the string 2013A above, below or through it) can be placed in the plunger 2018 which provides slight resistance on the string 2013A during pledget 13 deployment. The obstruction 2502 can be stationary or mobile and remain inside of the plunger 2018 while the string 2013A slides past. The stationary obstruction 2502 can be an integral part of the plunger 2018 (e.g., made together) or attached later directly to the plunger 2018 anywhere along the length of the plunger 2018. The mobile obstruction 2502 can be inserted into the plunger 2018 at any stage during construction of the assembly.

In some embodiments, obstruction 2502 is a compliant material such that (a) during the assembly process, a vacuum can be applied to plunger 2018 and the string 2013A will be able to pass obstruction 2502 such that it is retained by obstruction 2502 at least within a portion of plunger 2018, and (b) during ejection of the pledget, the string 2013A is able to pass obstruction 2502 and exit the plunger 2018 as it is deployed.

The obstruction 2502 can be made from a "soft" material (such as cotton, rayon, paper, etc.) as well as a harder material (e.g., plastic such as polyethylene, polypropylene, etc.). The thickness and material of the obstruction 2502 can be designed such that the obstruction 2502 acts like a diaphragm with a hole that would allow the string 2013A to go through. The obstruction 2502 can fill 0.1% to 99% of the cross-sectional area of the plunger 2018; in some embodiments 50% to 99% if the obstruction 2502 is made from a "soft" material (as a soft obstruction 2502 would give way to the string 2013A) and 1% to 90% (e.g., 1% to 60%) if the obstruction 2502 is made from a "harder" material. The cross-sectional shape of the obstruction 2502 can be circular, rectangular, triangular or a combination thereof. The largest outer diameter of the obstruction 2502 can be between 0.1% and 150% of the string 2013A knot diameter; in some embodiments between 10% and 90%.

FIGS. 26A-F shows various embodiments for the obstruction 2502. The obstruction 2502 can be in the shape of a "channel" 2502A, "cross-fin" 2502B, "half-moon" 2502C, "throttle" 2502D, "wings" 2502E and "spiral" 2502F, or any combination thereof. As one skilled in the art would appreciate based on a review of this disclosure, the geometry of the obstruction 2502 is not limited to the geometries just described, but can include anything that will act as an obstruction and will guide the string 2013A therethrough. Any such obstructions 2502 can be built into the plunger 2018 or attached to the inside of the plunger 2018 and can be placed anywhere along the length of the plunger 2018. Also, there can be more than one obstruction 2502 along the length of the plunger 2018.

If the obstruction 2502 is in the shape of a channel (or channels) 2502A, the string 2013A can sit in the channel 2502A and can be guided through it during ejection. The number of channels 2502A may be between one and five, e.g., between one and two. The height of the channel 2502A can be 0.1% to 150% of the string 2013A knot 2013B diameter; in some embodiments between 50% and 120% of the string 2013A knot 2013B diameter. Alternatively, the obstruction 2502 can be shaped as cross-fins 2502B. The number of fins 2502B may be between one and ten; in some embodiments between one and four. The distance between the fins 2502B can be from 0.1% to 150%, e.g., from 10%-90% of the string 2013A knot 2013B diameter. If the obstruction 2502 is in the shape of a half-moon 2502C, the height of the moon 2502C can be from 0.1% to 150%, e.g., from 10%-90% of the string 2013A knot 2013B diameter. Alternatively, the obstruction 2502 can be in the shape of a throttle 2502D where the diameter of the plunger 2018 is smaller at a certain point or points along the length of the plunger 2018 that will act like a resistance point. The diameter of the throttle 2502D can be from 0.1% to 150%, e.g., from 10%-90% of the string 2013A knot 2013B diameter. If the shape of the obstruction 2502 is in the form of wings 2502E, the number of wings 2502E may be between one and ten, e.g., between one and four. The distance between the wings 2502D can be from 0.1% to 150%, e.g., from 10%-90% of the string 2013A knot 2013B diameter. The cross-sectional shape of the wings 2502E can be circular, rectangular, triangular, trapezoidal, and elliptical, or any combination thereof. Another alternative is to create spirals or grooves 2502F inside of the plunger 2018 through which the string 2013A may be guided. The size of the spiral or the grooves 2502F can be adjusted such that the string 2013A can freely move through without getting stuck.

FIGS. 27A-D shows an embodiment that may be used for string 2013A storage and handling. A sticky tab (e.g., adhesive label) 2702 may be applied to the inside of the cap 2014 which retains the string 2013A during pledget 13 deployment. When the string 2013A is fully extended, perforations 2704 in the sticky tab 2702 tear to allow the string 2013A to deploy correctly. The sticky tab 2702 sticks to the cap 2014 but is raised over the string 2013A and thus barely sticks to the string 2013A and is capable of letting the string 2013A go once the pledget 13 is ejected.

The shape of the label 2702 can be circular, rectangular, triangular, trapezoidal, and elliptical, or a combination thereof. The material of the sticky tab 2702 may be made from one or more plastics, paper, paperboard, cardboard, textile, or any combination thereof. The strength of the adhesive on the sticky tab 2702 can be adjusted such that the sticky tab sticks to the cap 2014 material strongly and doesn't lift but releases the string 2013A material which can be cotton, rayon, or a combination thereof. The perforations 2704 on the sticky tab 2702 can be designed such that the sticky tab 2702 tears at the perforation 2704 easily without any extra resistance to the user as she's inserting the product. The sticky tab 2702 can be attached to the string 2013A end which is then attached onto the cap 2014 which is snapped onto the plunger 2018. Alternatively, the sticky tab 2702 may be attached to the cap 2014 first followed by the string 2013A end being tucked under the label 2702. The cap 2014 then can be snapped onto the plunger 2018. Yet alternatively, the end of the string 2013A can be dipped into a light adhesive to attach to the cap 2014 directly which will eliminate this need for a separate sticky tab 2702.

The amount of adhesive can be adjusted such that the string 2013A is loosely attached to the cap 2014 when the product is not in use and easily separates from the cap 2014 when the pledget 13 is inserted into the user's body. Alternatively, the end of string 2013A can be electrostatically charged and attached to the cap 2014 directly using electrostatic forces. Just like the string 2013A end dipped in adhesive, this will eliminate the need for a separate label 2702. The electrostatic forces can be adjusted such that the string 2013A is loosely attached to the cap 2014 when the product is not in use and easily separates from the cap 2014 when the product is inserted into the user's body.

In some embodiments, and potentially in lieu of a use of the sticky tab 2702, hook and loop fasteners such as VEL-CRO can be applied to the inside of the cap 2014 which retains the string 2013A during pledget 13 deployment. The interaction between the VELCRO and the end of string 2013A may create a minimal, predetermined amount of resistance to hold the string 2013A in place during deployment but release the string 2013A once the pledget 13 is fully ejected. The shape of the VELCRO can be circular, rectangular, triangular, trapezoidal, and elliptical or a combination thereof. The size of the VELCRO applied can be adjusted to create any required forces. Just like the adhesive label 2702, the VELCRO can be attached to the string 2013A end which is then attached onto the cap 2014 which is snapped onto the plunger 2018. Alternatively, the VEL-CRO may be attached to the cap 2014 first followed by the string 2013A end being tucked under the VELCRO. The cap 2014 then can be snapped onto the plunger 2018.

FIGS. 28A-D illustrate an embodiment including a cap 2814 where the string 2013A end is held on the cap 2814 until the string 2013A is pulled during pledget 13 deployment/ejection. In particular, FIGS. 28A-D shows a "tab" embodiment where the end of string 2013A (above or below the knot) is held in place by an opening between tabs 2802. However, the tabs 2802 can be of any shape, such as circular, rectangular, triangular, trapezoidal, and elliptical or a combination thereof. The number of tabs 2802 may be between one and ten, e.g., between two and five. The distance between the tabs 2802 can be 0.1% to 150%, e.g., from 10%-90% of the string 2013A knot diameter. The larger opening between the tabs 2802 can be 0.1% to 150%, e.g., between 30%-110% of the string 2013A knot diameter. The tabs 2802 can be manufactured separately and attached to the cap 2814 by any chemical (adhesive etc.) or mechanical technique (living hinge etc.) or a combination thereof (ultrasonic bonding etc.). In some embodiments, the tabs 2802 may be manufactured together with the cap 2814. After the tabs 2802 are attached to the cap 2814, the string 2013A can be tucked in between in the tabs 2802 and the cap 2814 is snapped onto the plunger 2018. Alternatively, the string 2013A can be tucked in between the tabs 2802 which are then attached to the cap 2814 which is then snapped onto the plunger 2018. There may be a hole 2021 on the other side of the cap 2814 to allow for a vacuum to suck the string 2013A through the plunger 2018 during assembly. The hole 2021 size can be between 1% and 150% of the string 2013A knot 2013B size, e.g., between 20% and 70%. The hole 2021 can then be closed by using a sticky tab or attaching another part by ultrasonic welding or any other attachment techniques.

Figure 29C:
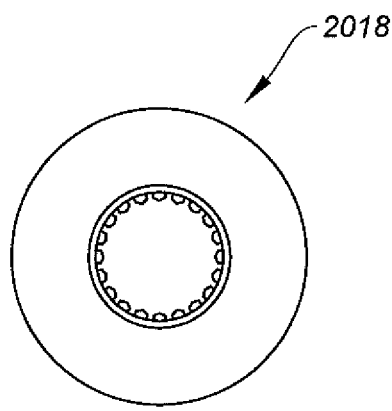
FIGS. 29A-D illustrate various designs and geometries for a plunger for managing a string.
Figure 29D:
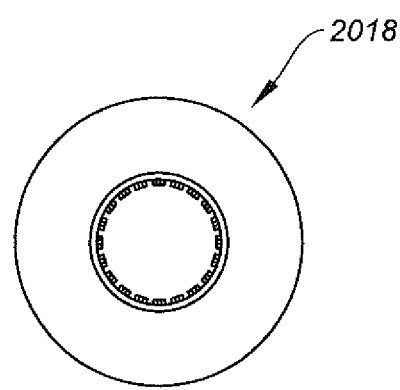
Figure 29A:
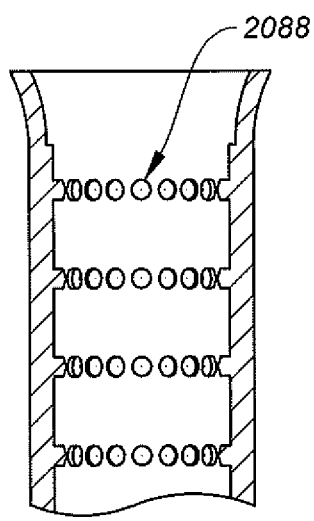
Figure 29B:
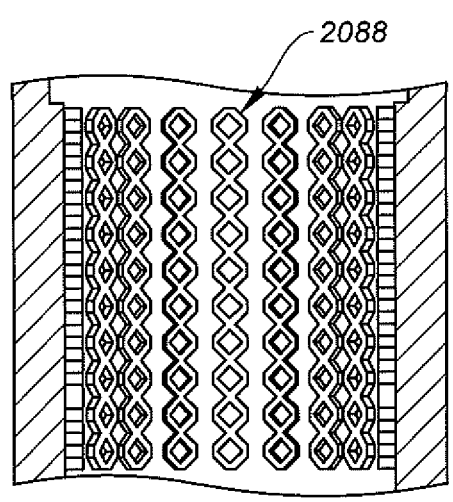

FIGS. 29A-D illustrates a use of a textured surface 2088 inside of the plunger 2018, such that a larger surface area is created that is in contact with the string 2013A. As the string 2013A (especially the string end) touches the textured surface 2088, the intermolecular forces can be large enough to hang onto the string 2013A in a sufficient, minimal amount such that a resistance is generated and the string 2013A untangles as the string 2013A travels through the plunger 2018. The intermolecular forces can be adjusted by adjusting the amount of texturing (the texture can be applied at a certain spot or all throughout the inner surface of the plunger 2018); the texture pattern (such as spikes or bumps as generally represented in FIGS. 29A and 29C, and diamonds as generally represented in FIGS. 29B and 29D, or any other pattern); the height of the pattern (the texture can be small, e.g., micron level or less, or large) and the material of the textured surface 2088 (the inside of the plunger 2018 can be made from a high friction material). If the inside of the plunger 2018 is made from a high friction material (such as a thermoplastic elastomer (TPE) or high durometer plastic), the material itself might be adequate enough to create the forces and no textured surface 2088 might be needed.

In some embodiments, the string 2013A material may include cotton, rayon, or a combination thereof which can "set-in" (wrinkle, tangle and take the shape of the position that they're in for an extended amount of time) as they're pretty flexible. Alternatively, a more "rigid" string 2013A material can be used that won't set-in like cotton and rayon and that will "bounce back" to its original shape right after the restriction (in this case being enclosed in the plunger 2018 for a while) is removed. This enables the string 2013A to not stay bunched up but untangle by itself and get back to its original shape right after the pledget 13 is ejected.

Conventional tampon strings may have a single knot towards the end of the string to enable an easier grasp point for the user. More than one knot can be placed on the string 2013A, such that it makes it more difficult for the string 2013A to set-in and helps the string 2013A to bounce back to its original shape upon insertion. The knot type can be changed to a bowline-like knot that will enable a big loop in the middle of the knot 2013B so that the string 2013A would untangle easier as it moves through the plunger 2018. The end of the string 2013A can be combed to increase the amount of interaction between the string 2013A and the sticky) tab (e.g., FIG. 27 as described above), string and the VELCRO as described above, and string and the texturing (e.g., FIG. 29 as described above).

Figures 30A, 30B, 30C, 30D:
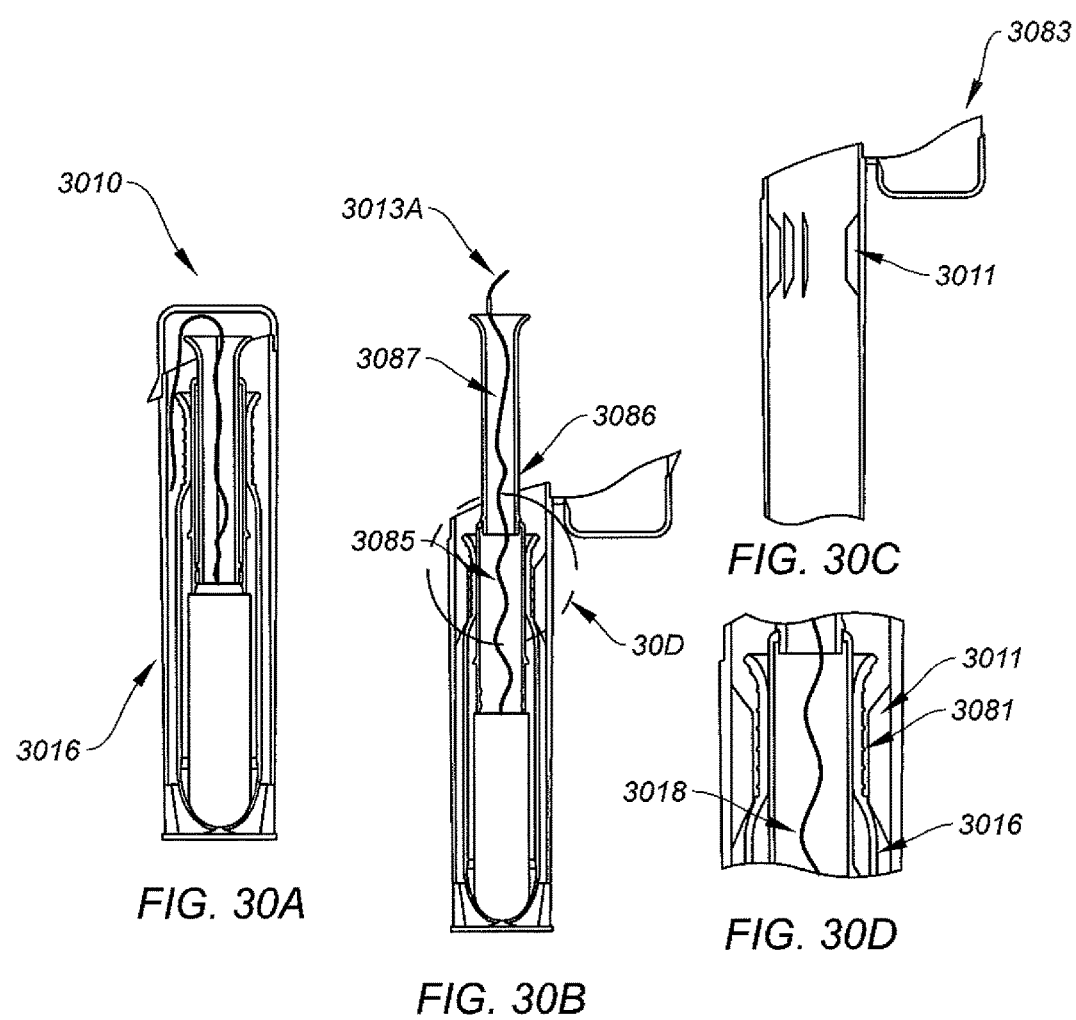
FIGS. 30A-D illustrate a tampon package applicator assembly in various stages of deployment having retention structures.

Referring now to FIGS. 30A-D, cap 3014 has retention structures 3011 that resist the force exerted on tampon applicator package assembly 3010 as the user draws the telescoping plunger 3018 rearward from the applicator barrel 3016. In some embodiments, telescoping plunger 3018 is a two-piece plunger having an outer plunger 3087 that engages barrel 3016 and inner plunger 3085 that engages outer plunger 3087. Inner plunger 3085 and outer plunger 3087 connect via a connection mechanism 3086, such as a detent mechanism, a flexible latch mechanism, a friction fit, and combinations thereof. In an initial state as shown in FIG. 30A, inner plunger 3085 is telescoped within outer plunger 3087 such that the tampon applicator package assembly is in a compact form. After opening the cap 3014 by moving the cap cover 3083 to reveal the tampon applicator (e.g., at least one of the plunger 3018 and the string 3013A). As the user draws the two-piece plunger rearward, a force of less than about 13 N is required to assemble the inner plunger 3085 and outer plunger 3087 in a fully-extended state. In some embodiments, a force of less than 8 N is required to assemble inner plunger 3085 and outer plunger 3087 in a fully-extended state. In further embodiments, a force of between about 3 N to about 7.5 N is required to assemble inner plunger 3085 and outer plunger 3087 in a fully-extended state. More preferably, the force required to assemble inner plunger 3085 and outer plunger 3087 in a fully-extended state is between about 4 N and about 6 N. The retention structures 3011 must cooperate with the applicator barrel 3016 (and in some embodiments, the grip region 3081) to ensure the applicator barrel 3016 is not advanced rearward out of the cap 3014 while the user is either (a) drawing the plunger 3018 rearward such that it is in a fully-extended state, or (b) assembling the inner plunger 3087 and outer plunger 3085 into a fully-extended state. In other words, the retention force (e.g., the force exerted by retention structures 3011 on the applicator barrel 3016) must be greater than the force to prepare the plunger in a fully-extended state. In some embodiments, the retention force is greater than about 13 N. In further embodiments, the retention force is greater than about 10 N. In further embodiments, the retention force is greater than about 8 N. Most preferably, the retention force is greater than the force to prepare the plunger in a fully-extended state, but is not difficult to achieve by the consumer. As such, in preferred embodiments, the retention force is between about 8 N and about 10 N.

Figures 31A, 31B:
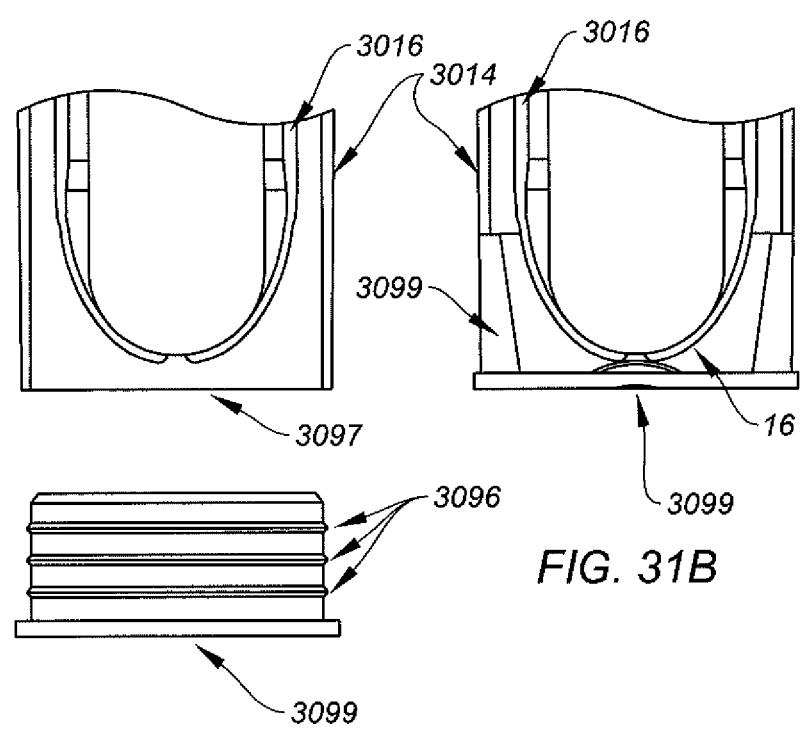
FIGS. 31A-B illustrate a tampon package applicator assembly.

FIGS. 31A and 31B show a further embodiment of the present disclosure that is advantageous from an assembly standpoint. FIG. 31A shows an exploded view of a plug 3099 and cap 3014 having retention structures 3099 in the form of ribs. FIG. 31B shows an assembled view of plug 3099 and cap 3014 having retention structures 3096. Retention structures 3096 must provide a sufficiently tight closure with cap 3014 while also mitigating the amount of interference with insertion end 16 the applicator 3016. During assembly, applicator 3016 is inserted via orifice 3097 and thereafter, plug is press-fit into orifice 3097 to sufficiently seal orifice 3097, thereby mitigating against any moisture and/or other foreign material from reaching the contents therein. Having such an assembly is advantageous as it allows assembly of the applicator 3016 into the barrel and thereby avoids further complications with keeping string 3018 in an orderly state, as described throughout the present disclosure.

Figures 32A, 32B:
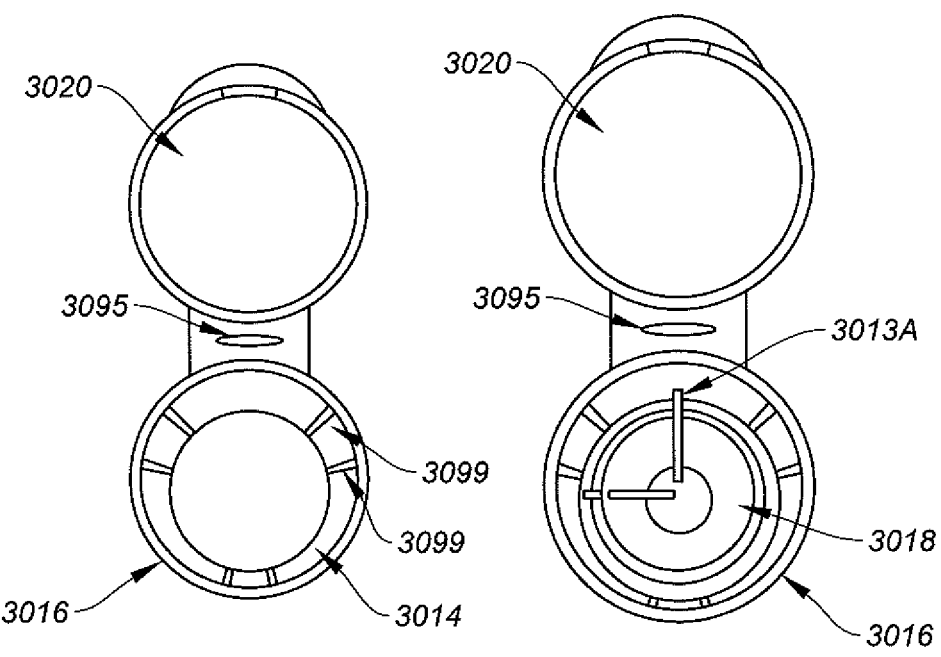
FIGS. 32A-B illustrate a tampon package applicator assembly having retention features.

FIGS. 32A-B show a further embodiment of a cap 3014 wherein the retention structures 3011 are eccentric such that the applicator 3016 is other than concentrically located within the cap 3014. Eccentric retention provides a larger space for the string 3013A and the knot 2013B and thereby reduces tangling during assembly and during removal of the applicator by the user during use. Eccentric retention further provides greater accessibility to the plunger 3018 as a larger gap is on one side of the applicator 3016 (e.g., the larger gap provides a larger space for the user to slide her finger adjacent the applicator and/or plunger 3018 to assist in extending the plunger 3018 and thereafter removing the applicator 3016 from cap 3014). Hinge 3095 is also advantageous in that it provides snap-action for the cap cover 3020 to open and close with respect to cap 3014. As the user opens cap cover 3020 and rotates it backward, hinge 3095 with is ovular recessed central portion acts as a spring and assists in deflecting cap cover 3020 away from the open end of cap 3014 and thereby providing access to the applicator 3014, plunger 3018 and/or string 3013A.

Figure 33B:
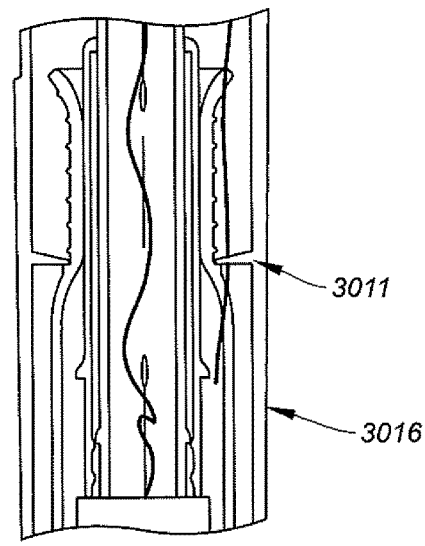
FIGS. 33A-C illustrate a tampon package applicator assembly having retention features.
Figure 33A:
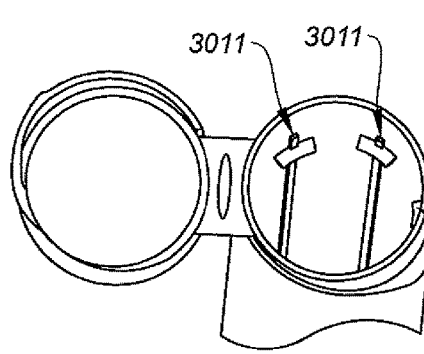
Figure 33C:
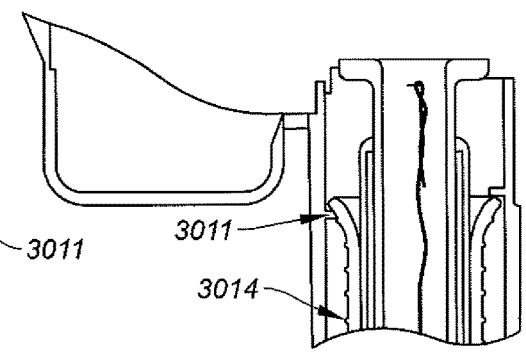

FIGS. 33A-C show a further embodiment where retention structures 3011 are flexible. These flexible retention structures 3011 shaped similar to tabs provide a sufficient retention force as described throughout the present disclosure. Furthermore, the flexible tabs 3011 are less likely to leave blemishes or marks on the applicator 3014 as it is removed from the cap 3016.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the scope thereof. Therefore, it is intended that the present disclosure not be limited to the particular embodiment(s) disclosed as the best mode contemplated, but that the disclosure will include all embodiments falling within the scope of the present disclosure.

It should also be noted that the terms "first", "second", "third", "upper", "lower", and the like may be used herein to modify various elements. These modifiers do not imply a spatial, sequential, or hierarchical order to the modified elements unless specifically stated.

What is claimed is:

1. A container for a personal care product comprising:
   a body forming a cavity for holding the personal care product; and
   a cap coupled to the body configured to enclose the personal care product within the container when the cap is in a first position and provide access to the personal care product when the cap is in a second position,
   wherein a product of Young's modulus and a second moment of inertia for the container is greater than $6.7 \times 10^5$ Nmm$^2$, and
   wherein the cap is configured to store at least a portion of a string associated with the personal care product.

2. The container of claim 1, wherein a material of the container comprises at least one of polyethylene or polypropylene.

3. The container of claim 1, wherein the container is formed via an application of a molding technique.

4. The container of claim 1, wherein the product of Young's modulus and the second moment of inertia for the container is greater than $9.2 \times 10^5$ Nmm$^2$.

5. The container of claim 1, wherein the cap is configured to receive the at least a portion of the string through a hole in a slit-surface associated with a plunger of the personal care product.

6. The container of claim 1, wherein the cap comprises at least one hole configured for application of a vacuum in order to thread a string associated with the personal care product through a plunger of the personal care product.

7. The container of claim 1, wherein said body has an inner wall having at least one retention structure.

8. The container of claim 7, wherein said at least one retention structure is at least one rib.

9. The container of claim 7, wherein said at least one retention structure is at least one flexible tab.

10. The container of claim 7, wherein said at least one retention structure includes multiple retention structures that are eccentrically positioned along said inner wall.

11. The container of claim 7, wherein said at least one retention structure exerts a retention force greater than about 8 N.

12. The container of claim 11, wherein said retention force is greater than about 10 N.

13. The container of claim 12, wherein said retention force is greater than about 13 N.

14. The container of claim 1, wherein said container further comprises an orifice at an end opposite the end of said cap, and a plug that is connectable to said orifice.

15. The container of claim 14, wherein said plug is press-fit into said orifice.

16. The container of claim 15, wherein said plug comprises at least one retention structure that engages said orifice and mitigates against moisture entering into said body.

* * * * *